United States Patent
Matsubara et al.

(10) Patent No.: US 9,335,317 B2
(45) Date of Patent: May 10, 2016

(54) STATUS MONITORING SYSTEM AND STATUS MONITORING METHOD FOR ROLLING DEVICE

(75) Inventors: Yukio Matsubara, Kuwana (JP); Noriaki Miwa, Kuwana (JP); Takakazu Kitagawa, Iwata (JP); Tomoya Sakaguchi, Kuwana (JP); Masayuki Kawakita, Kuwana (JP); Hisamitsu Maeda, Iwata (JP)

(73) Assignee: NTN CORPORATION, Osaka (JP)

( * ) Notice: Subject to any disclaimer, the term of this patent is extended or adjusted under 35 U.S.C. 154(b) by 270 days.

(21) Appl. No.: 14/002,878

(22) PCT Filed: Feb. 24, 2012

(86) PCT No.: PCT/JP2012/054592
§ 371 (c)(1),
(2), (4) Date: Sep. 18, 2013

(87) PCT Pub. No.: WO2012/117970
PCT Pub. Date: Sep. 7, 2012

(65) Prior Publication Data
US 2014/0007657 A1 Jan. 9, 2014

(30) Foreign Application Priority Data

Mar. 3, 2011 (JP) .................... 2011-045949
Mar. 3, 2011 (JP) .................... 2011-045950
Mar. 3, 2011 (JP) .................... 2011-045951
Mar. 3, 2011 (JP) .................... 2011-045952

(51) Int. Cl.
G01N 33/28 (2006.01)
G01M 13/04 (2006.01)
(Continued)

(52) U.S. Cl.
CPC ........... *G01N 33/2888* (2013.01); *G01M 13/04* (2013.01); *G01N 27/221* (2013.01); *F16C 19/52* (2013.01); *F16C 33/667* (2013.01)

(58) Field of Classification Search
CPC .. G01M 13/04; G01N 27/221; G01N 33/2888
USPC ........................................ 73/53.05
See application file for complete search history.

(56) References Cited

U.S. PATENT DOCUMENTS 4,315,421 A * 2/1982 Wilson .............. 72/42
4,498,305 A * 2/1985 Bzdula ............. 62/84
(Continued)

FOREIGN PATENT DOCUMENTS

CN 101784804 7/2010
EP 0141636 * 5/1985
(Continued)

OTHER PUBLICATIONS

EP 0141636.*
(Continued)

Primary Examiner — Lisa Caputo
Assistant Examiner — Tran M Tran

(57) ABSTRACT

A status monitoring system for accurately determining the contaminant water concentration in a lubricant oil used in a rolling device includes a contaminant water concentration monitoring device configured to monitor the contaminant water concentration in the lubricant oil. The contaminant water concentration monitoring device includes an electrostatic capacitance detector and an oil temperature measuring instrument, which are configured to detect the electrostatic capacitance and the oil temperature of the lubricant oil, respectively, and a water concentration calculation section configured to calculate the contaminant water concentration from the detected electrostatic capacitance and oil temperature in accordance with a predetermined rule.

14 Claims, 37 Drawing Sheets

(51) Int. Cl.
  *G01N 27/22* (2006.01)
  *F16C 33/66* (2006.01)
  *F16C 19/52* (2006.01)

(56) References Cited

U.S. PATENT DOCUMENTS

| | | | | |
|---|---|---|---|---|
| 4,517,547 | A * | 5/1985 | Gray et al. | 340/438 |
| 5,824,889 | A * | 10/1998 | Park et al. | 73/114.55 |
| 5,973,503 | A * | 10/1999 | Kuipers et al. | 324/698 |
| 6,196,057 | B1 * | 3/2001 | Discenzo | 73/54.01 |
| 6,746,610 | B2 * | 6/2004 | Manz et al. | 210/689 |
| 6,791,334 | B2 | 9/2004 | Horie et al. | |
| 6,911,830 | B2 * | 6/2005 | Heremans et al. | 324/698 |
| 7,006,953 | B2 * | 2/2006 | Takemura et al. | 703/2 |
| 7,370,514 | B2 * | 5/2008 | Halalay et al. | 73/53.05 |
| 7,835,875 | B2 * | 11/2010 | Halalay et al. | 702/50 |
| 8,118,953 | B2 * | 2/2012 | Iwamoto et al. | 148/659 |
| 8,359,811 | B2 | 1/2013 | Wilhelmy et al. | |
| 8,436,292 | B2 * | 5/2013 | Takahashi et al. | 250/227.25 |
| 8,534,128 | B2 * | 9/2013 | Murayama | 73/593 |
| 9,038,448 | B2 * | 5/2015 | Micali et al. | 73/114.77 |
| 2002/0113596 | A1 | 8/2002 | Horie et al. | |
| 2006/0169031 | A1 * | 8/2006 | Song et al. | 73/53.05 |
| 2010/0180664 | A1 | 7/2010 | Wilhelmy et al. | |

FOREIGN PATENT DOCUMENTS

| | | |
|---|---|---|
| JP | 58-127142 | 7/1983 |
| JP | 61-72667 | 5/1986 |
| JP | 62-137493 | 6/1987 |
| JP | 63-271124 | 11/1988 |
| JP | 3-118399 | 12/1991 |
| JP | 4-282018 | 10/1992 |
| JP | 7-12686 | 1/1995 |
| JP | 7-52479 | 11/1995 |
| JP | 10-253569 | 9/1998 |
| JP | 2000-9597 | 1/2001 |
| JP | 2002-181666 | 6/2002 |
| JP | 2002-277437 | 9/2002 |
| JP | 2004-44635 | 2/2004 |
| JP | 2006-138376 | 6/2006 |
| JP | 2006-258473 | 9/2006 |
| JP | 2007-10643 | 1/2007 |
| JP | 2007-310611 | 11/2007 |
| JP | 2008-286662 | 11/2008 |
| JP | 2010-5688 | 1/2010 |
| WO | WO 98/39631 | 9/1998 |

OTHER PUBLICATIONS

International Preliminary Report on Patentability issued on Sep. 12, 2013 in corresponding International Application No. PCT/JP2012/054592.

Japanese Office Action dated Jan. 6, 2015 in corresponding Japanese Patent Application No. 2011-045951.

Japanese Office Action dated Jan. 6, 2015 in corresponding Japanese Patent Application No. 2011-045952.

Chinese Office Action issued Jul. 30, 2015 in corresponding Chinese Patent Application No. 201280011533.9.

Extended European Search Report dated Mar. 4, 2015 in corresponding European Patent Application No. 12751866.0.

Mannebach, "Condition Monitoring for Hydraulic and Lubricating Fluids", SICFP'07, May 2007, Finland, pp. 317-326.

Day et al., "Setting Control Limits for Water Contamination in Hydraulic and Lubrication Systems", SICFP'07, May 2007, Finland, pp. 307-316.

Japanese Office Action dated Aug. 26, 2014 in corresponding Japanese Patent Application No. 2011-045949.

Japanese Office Action dated Aug. 26, 2014 in corresponding Japanese Patent Application No. 2011-045950.

Japanese Office Action dated Aug. 26, 2014 in corresponding Japanese Patent Application No. 2011-045951.

Japanese Office Action dated Aug. 26, 2014 in corresponding Japanese Patent Application No. 2011-045952.

L. Grunberg, "The Formation of Hydrogen Peroxide on Fresh Metal Surfaces," *Proc. Phys. Soc. LXVI, 3—B*, B66, 1953, pp. 153-161.

L. Grunberg et al., "The Acceleration of Pitting Failure by Water in the Lubricant," *Journal of the Institute of Petroleum*, vol. 44, No. 419, Nov. 1958, pp. 406-410.

L. Grunberg et al., "Hydrogen Penetration in Water-accelerated Fatigue of Rolling Surfaces," *Philosophical Magazine*, 8, 1963, pp. 1553-1568.

P. Schatzberg et al., "Effects of Water and Oxygen During Rolling Contact Lubrication," *Wear*, 12, 1968, pp. 331-342.

P. Schatzberg, "Inhibition of Water-Accelerated Rolling Contact Fatigue," *Journal of Lubrication Technology*, 231, Apr. 1971, pp. 231-235.

K. Tamada et al., "Occurrence of brittle flaking on bearings used for automotive electrical instruments and auxiliary devices," *Wear*, 199, 1996, pp. 245-252.

H. Tanimoto et al., "Observation of Hydrogen Permeation into Fresh Bearing Steel Surface by Thermal Desorption Spectrometry," *Japanese Society of Tribologists*, Proceedings of JAST Tribology Conference, Tokyo, May 2010, pp. 203-204.

Y. Matsubara et al., "A Novel Method to Evaluate the Influence of Hydrogen on Fatigue Properties of High Strength Steels," *Journal of ASTM International*, vol. 3, No. 2, Bearing Steel Technology, 2005, pp. 153-166.

H. Mikami et al., "Influence of Electrical Current on Bearing Flaking Life," *SAE International*, 2007, 2 cover pages and pp. 1-6.

T. Makino, Academic Dissertation, Kyoto University, 2000, pp. 134.

International Search Report mailed on Apr. 24, 2012 in corresponding International Application No. PCT/JP2012/054592.

* cited by examiner

WATER CONCENTRATION IN REGION ON THE OCEAN
OR WHERE TEMPERATURE CHANGE IS LARGE
(PREDICTED DATA)

WATER CONCENTRATION IN REGION ON LAND
OR WHERE TEMPERATURE CHANGE IS SMALL
(PREDICTED DATA)

RELATION BETWEEN CONTAMINANT WATER CONCENTRATION AND LIFE REDUCTION RATE IN PREPARATORY TEST (PREDICTED DATA)

RELATION BETWEEN CONTAMINANT WATER CONCENTRATION AND BEARING LIFE IN ACTUAL BEARING (PREDICTED DATA)

STATUS MONITORING SYSTEM AND STATUS MONITORING METHOD FOR ROLLING DEVICE

CROSS REFERENCE TO THE RELATED APPLICATION

This application is a U.S. national stage application of PCT/JP2012/054592, filed Feb. 24, 2012 and is based on and claims foreign priority benefit of Japanese patent applications No. 2011-045949, No. 2011-045950, No. 2011-045951 and No. 2011-045952, all filed Mar. 3, 2011, in the Japanese Intellectual Property Office, the entire disclosures of which are herein incorporated by reference as parts of this application.

BACKGROUND OF THE INVENTION

1. Field of the Invention

The present invention relates to a rolling device of an oil lubricated type and, more particularly, to a status monitoring system and a status monitoring device both associated with such rolling device of the particular type.

2. Description of Related Art

Some abnormality predications for bearing assemblies are currently available. In this respect, see, for example, the patent document 1 listed below. One of those abnormality predication includes measuring the degradation of a lubricant to thereby predicate the lifetime of the bearing assembly. Deterioration of the lubricant results in a reduction in thickness of an oil film at a contact portion within the bearing assembly, which leads to the bearing assembly susceptible to abrasion and/or surface damage. Accordingly, through the measurement of a deteriorated condition of the lubricant, reduction of the lifetime of the bearing assembly is monitored and predicated.

When rolling component part parts for use with rolling bearing assemblies and gears are used under a condition in which water may ingress (such as discussed in the non-patent documents 1 to 5 listed below) or under a condition in which they tend to be subjected to slide (such as discussed in the non-patent document 6 listed below), water or the lubricant is dissolved to generate hydrogen and, if the resultant hydrogen intrudes into a steel material, damages may arise quickly. Once a metal contact occurs at a contact surface between contact elements to such an extent as to allow a newly-formed metal surface to be exposed, generation of hydrogen as a result of decomposition of water and the lubricant and subsequent intrusion of hydrogen into the steel material will be accelerated. This is evidences by the experimental fact that consequent upon the temperature programmed hydrogen desorption analysis performed after a steel material used to form the rolling component part parts were subjected to abrasive wear with the use of a emery paper, while water and the lubricant had been supplied dropwise, diffusible hydrogen was palpably detected from the steel material used (such as discussed in the non-patent document 7 listed below). According to the analysis referred to above, a more amount of the diffusible hydrogen was detected when water, rather than the lubricant oil, was supplied dropwise. Accordingly, it may be regarded that when water is mixed in the lubricant for the rolling component part parts that are used under a condition in which a sliding motion takes place, hydrogen is further generated and is apt to intrude into the steel material. Since hydrogen is responsible to a considerable reduction in fatigue strength of the steel material (such as discussed in the patent document 8 listed below), the intrusion of hydrogen leads to a rapid damage even under the maximum contact surface pressure that is not so high.

PRIOR ART DOCUMENTS

Patent Documents

[Patent Document 1] JP Laid-open Patent Publication No. 2007-310611
[Patent Document 2] JP Laid-open Patent Publication No. 2006-138376

Non-Patent Documents

[Non-patent Document 1] L. Grunberg; Proc. Phys. Soc. (London), B66 (1953) 153-161
[Non-patent Document 2] L. Grunberg and D. Scott; J. Inst. Petrol., 44 (1958) 406-410
[Non-patent Document 3] L. Grunberg, D. T. Jamieson and D. Scott; Philosophical Magazine, 8 (1963) 1553-1568
[Non-patent Document 4] P. Schatzberg and I. M. Felsen; Wear, 12 (1968) 331-342
[Non-patent Document 5] P. Schatzberg; J. Lub. Tech., 231 (1971) 231-235
[Non-patent Document 6] K. Tamada and H. Tanaka; Wear, 199 (1996) 245-252
[Non-patent Document 7] H. Tanimoto, H. Tanaka and J. Sugimura; Proceedings of JAST Tribology Conference, (2010 Tokyo), 203-204
[Non-patent Document 8] Y. Matsubara and H. Hamada; Bearing Steel Technology, ASTM STP1465, J. M. Beswick Ed., (2005), 153-166
[Non-patent Document 9] H. Mikami and T. Kawamura; SAE Paper, (2007), No. 2007-01-0113
[Non-patent Document 10] T. Makino; Academic Dissertation (Kyoto University), (2000), pp 134

SUMMARY OF THE INVENTION

As discussed above, it may be said that when water admixes into the lubricant for use with rolling component part parts that is used under the condition involving the sliding motion, hydrogen is more generated and is apt to intrude into the steel material. The rolling component part parts appear to have a tendency of being increasingly used in the future under the condition susceptible to the generation of hydrogen. Accordingly, the need has been realized to monitor the contaminant water concentration in the lubricant oil (i.e., the concentration of water mixed into the lubricant oil) for the purpose of diagnosing whether the contaminant water concentration is high or low, so that the rapid damage originating from the hydrogen brittleness can be suppressed.

The patent document 2 referred to above is addressed to one of functions of a monitoring and diagnosing system in which the dielectric constant, which is in proportional relation with the electrostatic capacitance, as will be discussed later, is monitored to thereby monitor and diagnosis the extent to which the lubricant is oxidized. It has, however, been found the patent document 2 merely discloses a conception and is silent as to, for example, specific data. In addition, the patent document 2 is only limited to the diagnosis of the presence or absence of an abnormality in a rolling bearing assembly. The contaminant water concentration in the lubricant oil is unable to be determined only by the electrostatic capacitance and the temperature dependent characteristic must also be measured.

The reason for the intrusion of water into the lubricant oil used to lubricate a rolling device of an oil lubricated type will now be discussed. When it comes to the contaminant water concentration in the lubricant oil used in lubricating the rolling device of the oil lubricated type particularly where the rolling device is used outdoors, for example, in a wind power generating system, it appears that even though the lubricant oil seemingly stays reserved within a region that is macroscopically closed, the atmosphere is microscopically breathing outside of the device due to everyday change in temperature and/or everyday change in humidity. As a case in which a water component admixes into the lubricant oil used in the rolling device, such a mechanism as shown in FIG. 49 (oil bath lubrication) or FIG. 50 (circulating lubrication) may be through of. As shown in upper portions of the drawings of FIGS. 49 and 50, because the temperature inside the rolling device under operation becomes higher than the outside air temperature, a positive pressure develops within the rolling device with a portion of the inside air being discharged to the outside. On the other hand, when the temperature inside the rolling device lowers to a value lower than the outside air temperature as a result of the halt of the rolling device as shown in lower portions of the drawings of FIGS. 49 and 50, the outside air enters the rolling device. Where the outside air entering the rolling device is, of a high humidity, dew is developed inside the rolling device and the resultant water component subsequently admixes into the lubricant oil. As discussed above, it is suspected that even during the normal use the water component admixed into the lubricant oil. Where the rolling device is exposed to torrential rains and/or fierce weather as can be seen in a wind turbine generator or a construction machine and equipment, it appears that much water component may admix into the rolling device.

In view of the foregoing, the present invention has for its essential object to provide a status monitoring system and a status monitoring method both for monitoring the status of a rolling device of an oil lubricating type, which include, in a rolling device of an oil lubrication type, a function that can monitor and accurately determine the contaminant water concentration in the lubricant oil and has a capability of suppressing a premature damage of one or more rolling component parts originating from the hydrogen brittleness.

Means for Solving the Problems

In order to accomplish the foregoing object of the present invention, the status monitoring system for a rolling device herein provided in accordance with the present invention is a status monitoring system for monitoring the status of the rolling device, which includes a contaminant water concentration monitoring device to monitor a contaminant water concentration in a lubricant oil, the contaminant water concentration monitoring device including: an electrostatic capacitance detector to detect an electrostatic capacitance in the lubricant oil; an oil temperature measuring instrument to detect an oil temperature in the lubricant oil; and a water concentration calculation section to detect the contaminant water concentration in accordance with a predetermined rule from the electrostatic capacitance detected by the electrostatic capacitance detector and the oil temperature detected by the oil temperature measuring instrument.

According to the above described construction, since the provision is made of the electrostatic capacitance detector and the oil temperature measuring instrument for detecting the electrostatic capacitance and the oil temperature of the lubricant oil and the water concentration calculation section for detecting the contaminant water concentration from the detected electrostatic capacitance and the detected oil temperature, respectively, to that the contaminant water concentration may be determined from the electrostatic capacitance and the oil temperature, the contaminant water concentration can be accurately determined. For this reason, in the rolling device of the oil lubricating type, the contaminant water concentration in the lubricant oil is monitored and accurately determined and, also, it is possible to suppress the premature damage originating from the hydrogen brittleness of the rolling component part.

It is to be noted that in the specification hereby presented the term "rolling device" means any device including a component including an element capable of undergoing a rolling slide such as, for example, rolling bearings and gears. By way of example, in the case of a wind turbine generator, it includes a support device for a main shaft and a speed-increasing gear assembly. Any of the main shaft support device and the speed-increasing gear assembly makes use of rolling bearings of various types and they are lubricated by oil. Other than that, as the rolling device of the oil lubricating type includes the following machines and equipments. The oil lubrication, when scrutinized, includes a jet oiling, a circulating oiling, an oil mist lubrication, an air oil lubrication, a splash oiling, a hydraulic oil immersion and so on, which are broadly classified into an oil bath lubrication and a circulating oiling.

Gas turbine (Jet oiling)
Hydraulic pump (Hydraulic oil immersion)
Printing machine (Circulating oiling)
Twisting machine (Jet oiling or Circulating oiling)
Paper making machine (Circulating oiling)
Speed reducing machine for industrial machine (Circulating oiling)
Robotic speed reducing machine (Oil bath lubrication)
Aircraft engine (Jet oiling)
Various parts of Construction machine (Oil bath lubrication)
Roll neck in Iron and steel rolling machine (Oil mist lubrication)
Speed reducing machine for rolling machine (Circulating oiling)
Machine tool (Air oil lubrication)
Railway vehicle shaft and axle (Splash oiling)
Railway vehicle drive device (Oil bath lubrication)
Vertical milling tire roller
(Circulating oiling or Oil bath lubrication)
Speed reducing machine for Mill
(Circulating oiling or Oil bath lubrication)
Automobile speed reducing machine (Splash oiling)

The status monitoring system for the rolling device in accordance with the present invention may also include a lubricant oil reservoir capable of performing an oil bath lubrication or a circulating oiling mechanism capable of performing a circulating oiling. In this case, a measurement chamber for the electrostatic capacitance and the oil temperature may be provided inside or outside of a housing for the rolling device and the electrostatic capacitance detector and the oil temperature measuring instrument are installed within this measurement chamber.

Also, where a lubricant oil reservoir capable of performing the oil bath lubrication or the circulating oiling mechanism capable of performing the circulating oiling is employed, a measurement chamber for the electrostatic capacitance and the oil temperature may be provided inside or outside of a housing for the rolling device, in which measurement chamber the electrostatic capacitance detector and the oil temperature measuring instrument are installed within this measurement chamber. The provision of the measurement chamber for the electrostatic capacitance and the oil temperature within the rolling device makes it possible to define the measurement chamber with the utilization of a vacant space available in the housing and positioning of the measurement chamber allows the rolling device to become increased in size. If the measurement chamber for the electrostatic capacitance and the oil temperature is defined outside of the rolling device, it can be applied to the case in which there is no room for the measurement chamber to be defined within the housing of the rolling device and, also, a change in design of the existing rolling device can be minimized.

Where the measurement chamber referred to above is provided, a stirrer to stir the lubricant may be provided within the measurement chamber for the electrostatic capacitance and the oil temperature. When the lubricant oil is stirred, a mixed condition of the lubricant oil with water becomes good and the contaminant water concentration can be further accurately detected.

In the practice of the present invention, particularly where the measurement chamber referred to above is provided and the stirrer referred to above is also provided, the amount of the lubricant oil accumulated within the measurement chamber for measurement of the electrostatic capacitance and the oil temperature is preferably chosen to be equal to or smaller than 100 mL and the amount of variation is preferably chosen to be within ±5 mL.

Also, a unit to facilitate a discharge of water, having a specific gravity higher than the lubricant oil, and an additive from the measurement chamber of the rolling device and the electrostatic capacitance and the oil temperature, may be provided.

In the practice of the present invention, as hereinabove described, the use is preferred of an abnormality diagnostic section to compare the contaminant water concentration, calculated by the water concentration calculation section, with a threshold value and to determine the occurrence of an abnormality in the event that the contaminant water concentration is higher than the threshold value. The provision of the abnormality diagnostic section enables an abnormality diagnosis in the event that the contaminant water concentration is higher than the threshold value, and, therefore, the premature damage originating from hydrogen brittleness of the rolling component part can be assuredly suppressed. The threshold value referred to above may be determined in the following manner and set.

A method of setting the above mentioned threshold value in the abnormality diagnostic section may include determining a threshold value for the contaminant water concentration, which has been determined by means of a rolling slide fatigue test that is performed by injecting water into the lubricant oil, monitoring the contaminant water concentration by measuring the electrostatic capacitance and the oil temperature, feeding it back so as to control the amount of water injected so enable the contaminant water concentration to be maintained within a constant range; and setting the threshold value so determined to the abnormality diagnostic section as a threshold value. It is to be noted that the threshold value determined by means of this test is preferably of a value that attains a contaminant water concentration which is arbitrarily chosen as proper in determination. This equally applies to any of the various tests hereinafter referred to.

Also, the threshold value for the contaminant water concentration may be determined through a rolling slide fatigue life test in which a slide is caused in a contact surface by means of a motion mechanism between elements that contact with each other, which threshold value, so determined, is then to set in the abnormality diagnostic section as a threshold value.

The threshold value for the contaminant water concentration may be determined through a rolling slide fatigue life test in which a slide is forcibly caused in a contact surface between elements that contact with each other, which threshold value, so determined, is then set in the abnormality diagnostic section as a threshold value.

The threshold value for the contaminant water concentration may be determined through a rolling slide fatigue life test in which a one direction rotation is made at a constant rotational speed before an damage occurs, which threshold value, so determined, is then set in the abnormality diagnostic section as a threshold value.

The threshold value for the contaminant water concentration may be determined through a rolling slide fatigue life test in which an operation under acceleration and deceleration is carried out by the time an damage occurs, which threshold value, so determined, is then set in the abnormality diagnostic section as a threshold value.

The threshold value for the contaminant water concentration may be determined through a rolling slide fatigue life test in which a rocking motion is carried out by the time an damage occurs, which threshold value, so determined, is then set in the abnormality diagnostic section as a threshold value.

The threshold value for the contaminant water concentration may be determined through a rolling slide fatigue life test of a mechanism for directly connecting a main shaft of a servomotor and a spindle of a testing portion in order to eliminate an overlapping vibration component as soon as possible so that an damage from a rocking motion can be accurately detected with a vibration, which the threshold value, so determined, is then set in the abnormality diagnostic section as a threshold value.

The threshold value for the contaminant water concentration may be determined through a rolling slide fatigue life test in which a motor and a spindle of a testing portion are insulated with the use of a rolling element, made of a ceramic material, for a support bearing assembly for the spindle in order to facilitate an abrasion of an object to be damaged by supplying an electric current between contact elements with the to-be-damaged object being on a positive pole side, which threshold value, so determined, is then set in the abnormality diagnostic section as a threshold value.

The threshold value for the contaminant water concentration may be determined through a rolling slide fatigue life testing device capable of performing accelerating and decelerating operation and a rocking motion in addition to the one direction rotation at the constant rotational speed, which threshold value, so determined, is then set in the abnormality diagnostic section as a threshold value.

In the status monitoring system of the present invention, a vibration sensor to monitor a vibration of a bearing assembly forming the rolling device and a vibration abnormality diagnostic section to determine the occurrence of an abnormality in the bearing assembly with the use of an output of the vibration sensor may be further provided.

Since the status monitoring system is provided with the vibration sensor for monitoring the vibration of the bearing assembly forming the rolling device and the vibration abnormality diagnostic section which determines the occurrence of an abnormality in the bearing assembly with the use of an output of the vibration sensor so that the detection of the contaminant water concentration and the abnormality diagnosis relaying on the vibration detection are concurrently used, the abnormality diagnosis of the bearing assembly can be performed comprehensively.

The vibration abnormality diagnostic section may include a first calculation block, a second calculation block, an envelope processing block and a diagnostic block. The first calculation block is configured to calculate an effective value of the vibration waveform measured with the use of the vibration sensor. The envelope processing block is configured to generate an envelope waveform of the vibration waveform by performing an envelope process on the vibration waveform measured with the use of the vibration sensor. The second calculation block is configured to calculate an effective value of an alternating current component of the envelope waveform generated by the envelope processing block. The diagnostic block is configured to diagnose the occurrence of the abnormality in the rolling bearing assembly on the basis of the effective value of the vibration waveform, measured by the first calculation block, and the effective value of the alternating current component of the envelope waveform calculated by the second calculation block.

In one embodiment of the present invention, a rotation sensor may be provided to detect the rotational speed of a shaft, which is supported by a rolling bearing assembly, or the rolling bearing assembly, in which case the vibration abnormality diagnostic section further includes a modified vibration degree calculation block and a modified modulation degree calculation block. The modified vibration degree calculation block is configured to calculate a modified vibration degree which is the effective value of the vibration waveform calculated by the first calculation block normalized with the rotational speed. The modified modulation degree calculation block is configured to calculate a modified modulation degree which is the effective value of the alternating current component of the envelope waveform calculated by the second calculation block normalized with the rotational speed. And, the diagnostic block is configured to diagnose the occurrence of the abnormality in the rolling bearing assembly on the basis of a chronological change of the modified vibration degree and the modified modulation degree.

In another embodiment of the present invention, the status monitoring system may further include a displacement measuring instrument to detect a relative displacement between inner and outer rings, both employed in a bearing assembly forming the rolling device, and an displacement abnormality diagnostic section which determines the occurrence of an abnormality in the bearing assembly with the use of an output of the displacement measuring instrument. And, the abnormality diagnostic section makes use of a detection value of the displacement sensor to diagnose the occurrence of the abnormality in the rolling bearing assembly.

In a further embodiment of the present invention, the status monitoring system may further include an AE sensor to detect an acoustic emission wave generated from the rolling bearing assembly. And, the abnormality diagnostic section is configured to diagnosis the occurrence of the abnormality in the rolling bearing with the use of a detection value of the AE sensor.

In a still further embodiment of the present invention, the status monitoring system may further include a sensor configured to detect the amount of abrasion powder or any other impurities contained in the lubricant oil. And, the abnormality diagnostic section is configured to determine the occurrence of an abnormality in the lubricant oil with the use of an output of this sensor.

The status monitoring system in accordance with another aspect of the present invention makes use of the vibration monitoring system referred to above and makes use, in the abnormality diagnosis of the contaminant water concentration, of a threshold value which is determined through a rolling slide fatigue life test, in which the contaminant water concentration is monitored by charging water into a lubricant oil by means of a water injector and measuring the electrostatic capacitance and the oil temperature and a appropriate amount of water, that is determined from the contaminant water concentration obtained from a result of this measurement, is fed back to the water injector to thereby control the amount of water charged so as to maintain the contaminant water concentration at a value within a constant range. It is to be noted that the threshold value determined by this test has to be of a value that attains a contaminant water concentration which is arbitrarily chosen as proper in determination. It is also to be noted that the term "appropriate amount of water" referred to above has to be the amount determined by the use of a relation formula and/or table in which the relation between the contaminant water concentration and the amount of water to be supplied is suitably defined. This equally applies to any of the various tests hereinafter referred to.

In place of the water being charged, the threshold value for the contaminant water concentration may be determined through a rolling slide fatigue life test, in which a slide is caused by a motion mechanism between elements that contact with each other, and such threshold value so determined being used in abnormality diagnosis as a threshold value; or the threshold value for the contaminant water concentration may be determined through a rolling slide fatigue life test, in which a slide is forcibly caused to occur between elements that contact with each other, and such threshold value so determined being used in abnormality diagnosis as a threshold value; or the threshold value for the contaminant water concentration may be determined through a rolling slide fatigue life test in which operation under acceleration and deceleration is carried out by the time an damage occurs, and such threshold value so determined being used in abnormality diagnosis as a threshold value.

Also, in place of the water being charged, in place of the water being charged, the threshold value for the contaminant water concentration may be determined through a rolling slide fatigue life test, in which a motor and a spindle of a testing portion are insulated with the use of a rolling element, made of a ceramic material, for a support bearing assembly for the spindle in order to facilitate an abrasion of an object to be damaged by supplying an electric current between contact elements with the to-be-damaged object being on a positive pole side, and such threshold value so determined being used in the abnormality diagnosis as a threshold value. The phenomenon has been well known in which, in the event that the electric current is supplied between the contact elements with the object to be damaged held on the positive pole side, the abrasion of such to-be-damaged object is facilitated. Accordingly, the threshold value for the contaminant water concentration may be determined by a test, similar to that described above, with the use of the rolling element made of the ceramic material used in the support bearing for the spindle and also of the insulated structure between the motor and the spindle of the testing portion.

In the status monitoring system of the present invention, a life reduction rate monitoring section may be further provided, which is configured to determine a life reduction rate of the rolling component part of the rolling device from the contaminant water concentration, which has been detected by the water concentration calculation section, with the use of a relation between the contaminant water concentration and the life reduction rate of the rolling component part included in the rolling device.

The hydrogen brittleness of the rolling component part in, for example, the bearing assembly or the like has its probability of occurrence that increase as the water in the lubricant oil increases. Accordingly, if the relation between the contaminant water concentration and the life reduction rate of the rolling component part is determined beforehand and is then set in the life reduction rate monitoring section, the life reduction rate of the rolling component part in, for example, the bearing assembly can be determined with the use of the above described relation and the contaminant water concentration in the lubricant oil that has been so detected. The detection of the contaminant water concentration is carried out by detecting the electrostatic capacitance and the oil temperature in the lubricant oil and detecting, with the water concentration calculation section, in accordance with a predetermined rule from the detected electrostatic capacitance and oil temperature in the lubricant oil. Since the contaminant water concentration and the electrostatic capacitance and the oil temperature have a certain relation with each other, such relation has to be determined beforehand and is then set in the water concentration calculation section. It is to be noted that the term "beforehand" referred to above is intended to mean the timing before the monitoring is performed by the status monitoring device for the rolling component part. Thus, the life reduction rate originating from the hydrogen brittleness of the rolling component part in, for example, the bearing assembly can be determined.

In this status monitoring system, there may be also provided a remaining life estimation section configured to estimate a remaining life of the rolling component part with the use of the life reduction rate, outputted by the life reduction rate monitoring section, and a predetermined remaining life estimation formula. Since there is a close relationship between the life reduction rate and the remaining life, the remaining life can be estimated if the life reduction rate is determined, and, for example, it is possible to predicate the timing of occurrence of the exfoliation in the bearing assembly as originating from the hydrogen brittleness. Accordingly, when preparation for the maintenance is beforehand made in anticipation of the occurrence of the abnormality, the length of time of halt in operation subsequent to the occurrence of the abnormality can be shortened. That effect is marked particularly in the case of the wind turbine generator.

The status monitoring method in accordance with a further aspect of the present invention includes a water concentration monitoring step of detecting the contaminant water concentration in an oil in accordance with a predetermined rule from an electrostatic capacitance and oil temperature in a lubricant oil, used to lubricate a rolling component part, the electrostatic capacitance and oil temperature being detected with the use of a status monitoring system as described in claim 28; and a life reduction rate calculating step of calculating a life reduction rate of the rolling component part in the rolling device from the contaminant water concentration which has been detected during the execution of the water concentration monitoring step with the use of a relation between a predetermined contaminant water concentration and the life reduction rate of the rolling component part. According to this method, in a manner similar to that described in connection with the status monitoring device for the rolling component part in accordance with the present invention, the life reduction rate exhibited because of the hydrogen brittleness of the rolling component part of the bearing assembly or the like can be determined.

Also, the status monitoring method in accordance with this further aspect of the present invention can determine the relation between the contaminant water concentration and the life reduction rate of the rolling component part with the use of the status monitoring system including the life reduction rate monitoring section in accordance with any one of the following processes (A) to (G):

(A) By means of a rolling slide fatigue test on a steel material, which test is performed by injecting water into the lubricant oil, which is used to lubricate a test piece made of the steel material, by means of a water injector, the contaminant water concentration is monitored by measuring an electrostatic capacitance and an oil temperature, and feeding an appropriate amount of water, obtained from the contaminant water concentration obtained as a result of measurement, back to the water injector so as to control the amount of water injected so as to maintain the contaminant water concentration within a constant range, and a relation of the life reduction rate relative to the contaminant water concentration is determined and the relation, so determined, is then set in a life reduction rate monitoring section as a relation between the predetermined contaminant water concentration and the life reduction rate of the rolling component part. It is to be noted that the relation between the contaminant water concentration and the life reduction rate of the rolling component part, which has been so determined, may be set in the life reduction rate monitoring section as it stands, but it may be set in the life reduction rate monitoring section with a suitable modification applied thereto. Hereinafter, this equally applied to each of the following tests.

(B) A relation of a life reduction rate relative to a contaminant water concentration is determined by means of a rolling fatigue life test of a steel material in which a slide is caused by a motion mechanism between elements, that contact with each other, to occur in a contact surface, and the relation, so determined, is then set in the life reduction rate monitoring section as a relation between the predetermined contaminant water concentration and the life reduction rate of the rolling component part.

(C) A relation of a life reduction rate relative to a contaminant water concentration is determined by means of a rolling fatigue life test of a steel material in which a slide is forcibly caused between elements, that contact with each other, to occur in a contact surface, and the relation, so determined, is then set in the life reduction rate monitoring section as a relation between the predetermined contaminant water concentration and the life reduction rate of the rolling component part.

(D) A relation of a life reduction rate relative to a contaminant water concentration is determined by means of a rolling fatigue life test of a steel material in which an operation under acceleration and deceleration is continued until the time an damage occur, and the relation, so determined, is then set in the life reduction rate monitoring section as a relation between the predetermined contaminant water concentration and the life reduction rate of the rolling component part.

(E) A relation of a life reduction rate relative to a contaminant water concentration is determined by means of a rolling fatigue life test of a steel material in which a rocking operation is continued until the occurrence of an damage occur, and the relation, so determined, is then set in the life reduction rate monitoring section as a relation between the predetermined contaminant water concentration and the life reduction rate of the rolling component part.

(F) A relation of a life reduction rate relative to a contaminant water concentration is determined by means of a rolling fatigue life test of a steel material performed by a mechanism in which, in order to accurately detect through an vibration an damage under a rocking motion, a main shaft of a servomotor and a spindle of a testing portion utilizing a test piece made of a steel material are connected directly with each other to thereby preferably remove an overlapping vibration component, and the relation, so determined, is then set in the life reduction rate monitoring section as a relation between the predetermined contaminant water concentration and the life reduction rate of the rolling component part.

(G) A relation of a life reduction rate relative to a contaminant water concentration is determined by means of a rolling fatigue life test, in which utilizing the fact that an abrasion of an object to be damaged is facilitated by supplying an electric current between contact elements with the to-be-damaged object held in a positive pole side and using a rolling element made of a ceramic material in a support bearing assembly for a spindle, an insulating structure is formed between a motor and a spindle of a testing portion, and the relation, so determined, is then set in the life reduction rate monitoring section as a relation between the predetermined contaminant water concentration and the life reduction rate of the rolling component part.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
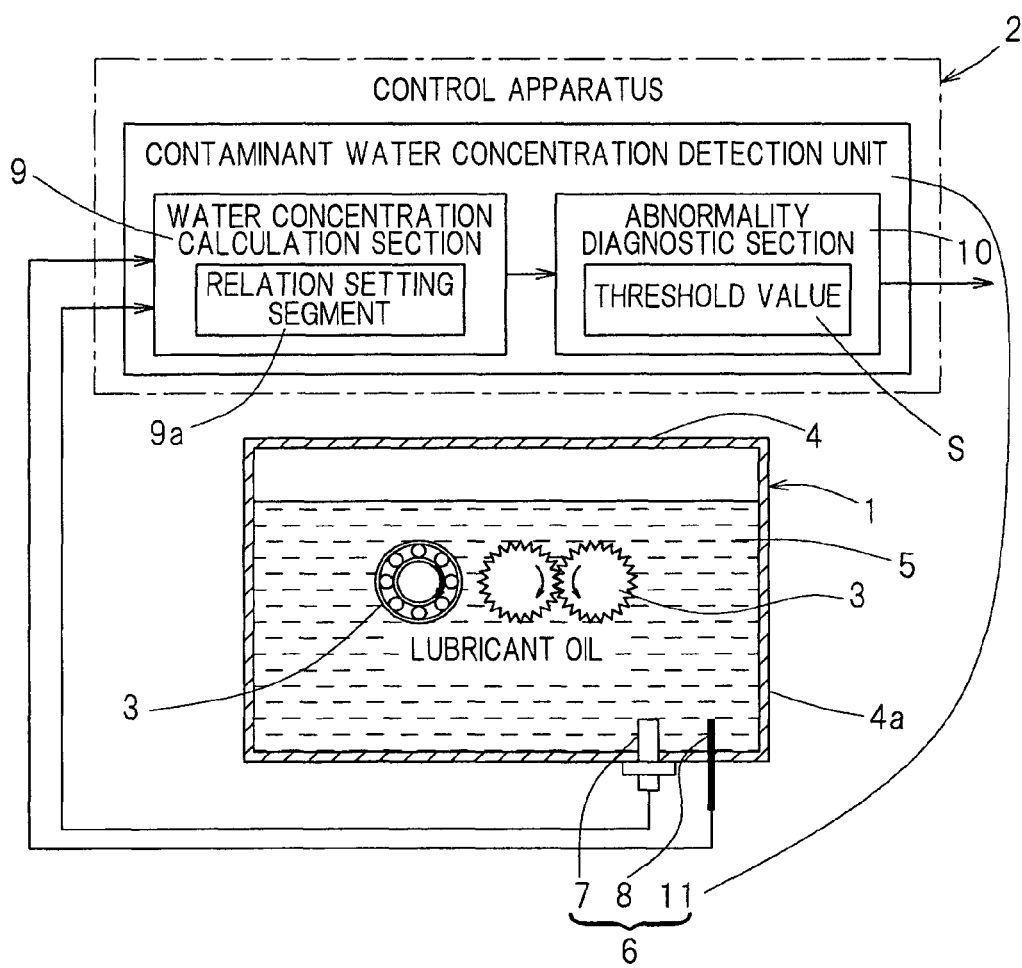
FIG. 1 is a block diagram showing a conceptual construction of a status monitoring system for a rolling device in accordance with a first embodiment of the present invention.

A status monitoring system for a rolling device, which is designed in accordance with a first embodiment of the present invention, will now be described with particular reference to FIG. 1. FIG. 1 illustrates a conceptual construction of the status monitoring system for the rolling device. The illustrated status monitoring system for the rolling device includes a rolling device 1 and a control apparatus 2 for controlling the rolling device 1. The rolling device 1 refers to portions of the status monitoring system excluding the control apparatus 2. The rolling device 1 stands for a device comprised of component parts including a contact element such as, for example, a rolling bearing assembly or a gear of a kind that undergoes a rolling slide and may be a speed reducing machine, a speed-increasing gear assembly or any other machines of various kinds, but is comprised of, for example, any one of various devices enumerated hereinbefore under the heading of "Means for Solving the Problems".

In the illustrated embodiment, the rolling device 1 has a plurality of rolling component parts 3 built in a housing 4 thereof, in which plurality of rolling component parts include a rolling bearing assembly and/or gears. It is to be noted that the term "rolling component part" referred to in this specification should be understood as meaning a component part including a contact element that undergoes a rolling slide. The lubricating system is an oil bath lubrication system, which is one of oil lubricating systems, and, hence, a portion of the housing 4 is rendered to be a lubricant oil reservoir 4a in which a lubricant oil 5 is reserved so that the whole of or some of the rolling component parts 3, defined above, can be immersed.

In the rolling device 1 of the construction described above, there is provided a contaminant water concentration monitoring device 6 for monitoring the contaminant water concentration in the lubricant oil 5 within the lubricant oil reservoir 4a. This contaminant water concentration monitoring device 6 includes an electrostatic capacitance detector 7 for detecting the electrostatic capacitance in the lubricant oil 5, an oil temperature measuring instrument 8 for detecting the oil temperature, and a contaminant water concentration detection unit 11. The contaminant water concentration detection unit 11 referred to above includes a water concentration calculation section 9 for detecting the contaminant water concentration in accordance with a predetermined rule from the electrostatic capacitance and the oil temperature, which have been detected respectively by the electrostatic capacitance detector 7 and the oil temperature detecting unit 8, and an abnormality diagnostic section 10 configured to compare the contaminant water concentration, which has been calculated by the water concentration calculation section 9, with a threshold value S and then to determine the occurrence of an abnormality in the event that it is greater than the threshold value S. It is, however, to be noted that the abnormality diagnostic section 10 may not be necessarily employed. The electrostatic capacitance detector 7 referred to above may be of any type provided that the electrostatic capacitance of a liquid, in which it is immersed, can be detected and may be employed in the form of a capacitance meter of any kind. The oil temperature measuring instrument 8 referred to above is employed in the form of a thermocouple or the like. The electrostatic capacitance detector 7 and the oil temperature measuring instrument 8 may be in the form of an electrostatic capacitance oil temperature unit 7A of one piece structure in which they are integrated together.

The water concentration calculation section 9 and the abnormality diagnostic section 10, that is, the contaminant water concentration detection unit 11 is comprised of a computer such as, for example, a microcomputer or a personal computer or the like, and a program therefor, or dedicated electronic circuits. For example, it is provided as a part of the control apparatus 2 of a computer type for controlling the rolling device 1 or provided as a device independent from the control apparatus 2.

The water concentration calculation section 9 has a relation setting segment 9a, in which relations between the electrostatic capacitance and the oil temperature and the contaminant water concentration are set in the form of computing formulas and/or tables and calculates the contaminant water concentration with the use of a rule stored in the relation setting segment 9a, that is, a predetermined rule.

According to the status monitoring system for the rolling device of the construction described above, the electrostatic capacitance in the lubricant oil 5 and the oil temperature of the lubricant oil 5 are detected by the electrostatic capacitance detector 7 and the oil temperature measuring instrument 8, respectively, and, from the electrostatic capacitance and the oil temperature both so detected, the contaminant water concentration is detected by the water concentration calculation section 9. As described above, since arrangement has been made to determine the contaminant water concentration from the electrostatic capacitance and the oil temperature, the contaminant water concentration can be accurately determined. Accordingly, in the rolling device 1 of the oil lubrication type, the contaminant water concentration in the lubricant oil 5 can be monitored and then accurately determined and, therefore, the premature damage of the rolling component parts that originates from hydrogen brittleness can be suppressed. Also, since the abnormality diagnostic section 10 is provided so that, in the event of the contaminant water concentration exceeding the threshold value S, the occurrence of the abnormality may be determined, the premature damage of the rolling component parts 3 that originates from hydrogen brittleness can be further assuredly suppressed. The reason that the contaminant water concentration can be accurately detected from the electrostatic capacitance and the oil temperature will be discussed in detail later in connection with a method of setting the threshold value S.

Figure 2:
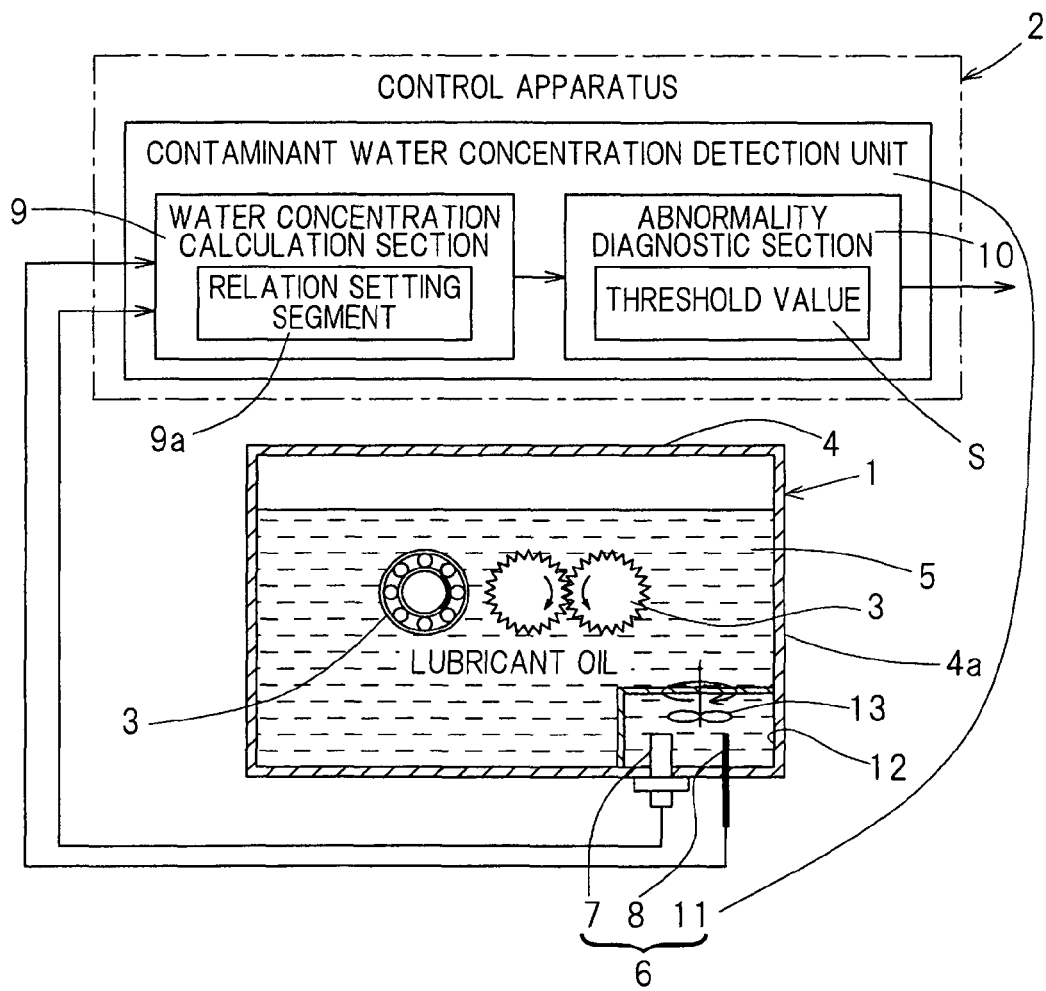
FIG. 2 is a block diagram showing a conceptual construction of the status monitoring system for the rolling device in accordance with a second embodiment of the present invention.

Although in the practice of the foregoing embodiment, it has been described that the electrostatic capacitance and the oil temperature of the lubricant oil 5 within the lubricant oil reservoir 4a in the housing 4 are measured, a measurement chamber 12 communicated with the lubricant oil reservoir 4a may be provided in a portion of the housing 4 so that the electrostatic capacitance detector 7 and the oil temperature measuring instrument 8 may measure the electrostatic capacitance and the oil temperature within the measurement chamber 12, respectively, such as shown in connection with a second embodiment shown in FIG. 2. In such case, a stirrer 13 for stirring the lubricant oil 5 within the measurement chamber 12 may be employed. The measurement chamber 12 may be in the form of a partitioned chamber formed with partitions provided within the measurement chamber 12. If the measurement chamber 12 is provided within the housing 4, an undesirable increase in size of the rolling device, which would result from the provision of the measurement chamber 12, can be avoided. The stirrer 13 is made up of, for example, a rotary blade for stirring purpose and a motor for driving the rotary blade. Where the measurement chamber 12 is provided and the stirrer 13 is provided, it is preferred that the amount of the lubricant oil to be reserved within the measurement chamber 12 is equal to or smaller than 100 mL and, simultaneously, the amount of variation is set to a value within ±5 mL. Other structural features in the second embodiment of the present invention shown in FIG. 2 than those described above are similar to those shown in and described in connection with the first embodiment shown in FIG. 1.

The provision of the measurement chamber 12 makes it possible to measure the electrostatic capacitance and the oil temperature in a stable fashion. Also, the provision of the stirrer 13 makes it possible to facilitate the mixing of the lubricant oil and water together, which leads to a stable measurement of the electrostatic capacitance and the oil temperature.

While the description will be made later together with a rolling slide fatigue life test, if the lubricant oil and the water are not satisfactorily mixed together, the value of the electrostatic capacitance will become unstable as the contaminant water concentration increases. This equally applies to the monitoring of the contaminant water concentration in the lubricant oil used in the rolling device of any of the oil bath circulating type and the oil lubrication type. While the rolling slide fatigue life test in which the condition of mixing of the lubricant oil and the water is deliberately made good, it can be easily imagined that since the case may arise in which the rolling device is stopped, the condition of mixing of the lubricant oil and the water is not good. It may happen that the lubricant oil and the water are separated from each other. For this reason, even in the rolling device 1, it is desirable that a mechanism for well mixing the lubricant oil and the water is preferably provided so that the electrostatic capacitance can be measured as accurately as possible. For this reason, the stirrer 13 is preferably provided to perform the stirring.

Although not shown, the stirrer 13 may be provided in a corner portion or the like within the lubricant oil reservoir 4a without the measurement chamber 12 being provided. However, in order to render the mixing condition of the lubricant oil and the water to good, it is preferred to employ the measurement chamber 12 is provided by partitioning. Unless the partitioning be made, it may be suspected difficult to render the mixing condition of the lubricant oil and the water to be good. However, if the mixing condition of the lubricant oil and the water is not good, a rather high electrostatic capacitance value will be measured and, therefore, the contaminant water concentration will be increased, that is, it is possible to monitor on safer side. If the lubricant oil and the water are separated from each other, it may be expected that a rather further high electrostatic capacitance value may be measured. In such case, it is to be noted that it will become an excessively safer monitoring and there is the possibility that the number of maintenance servicing and the cost will become excessive.

Figure 3:
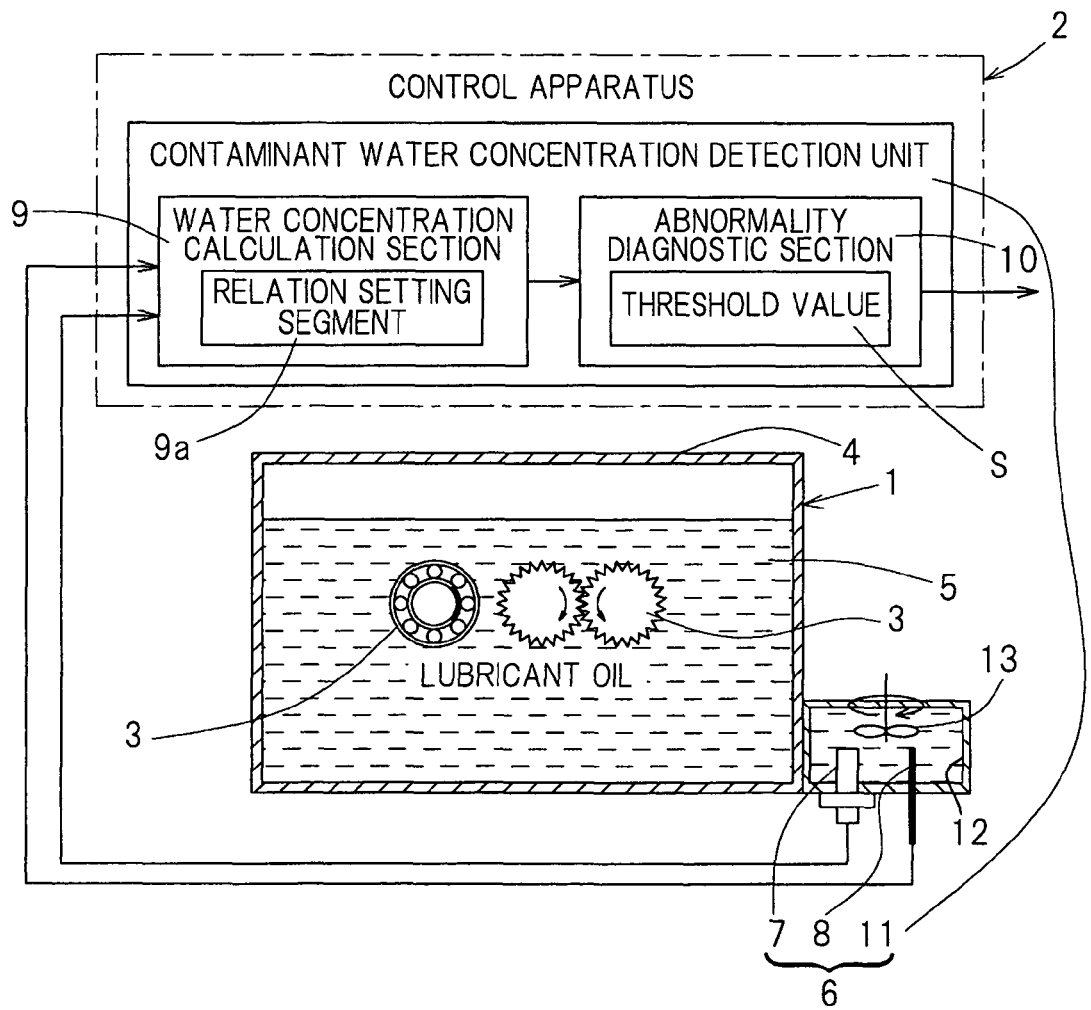
FIG. 3 is a block diagram showing a conceptual construction of the status monitoring system for the rolling device in accordance with a third embodiment of the present invention.

The measurement chamber 12 may be disposed outside of the housing 4 as shown in connection with a third embodiment shown in FIG. 3. In this case, the measurement chamber 12 may be provided either in a fashion adjoining the housing 4 as shown or in a fashion separated from the housing 4. Where it is separated, the measurement chamber 12 and the lubricant oil reservoir 4a in the housing 4 are communicated with a communicating tube (not shown). If the measurement chamber 12 is provided outside of the housing 4, the measurement by the electrostatic capacitance detector 7 and the oil temperature measuring instrument 8 can be accomplished even though there is no proper space within the housing 4 where the measurement chamber 12, the electrostatic capacitance detector 7 and the oil temperature measuring instrument 8 are installed. It is to be noted that other structural features and effects of the third embodiment shown in FIG. 3 than those described above are similar to those shown in and described in connection with the first embodiment shown in FIG. 1.

Figure 4:
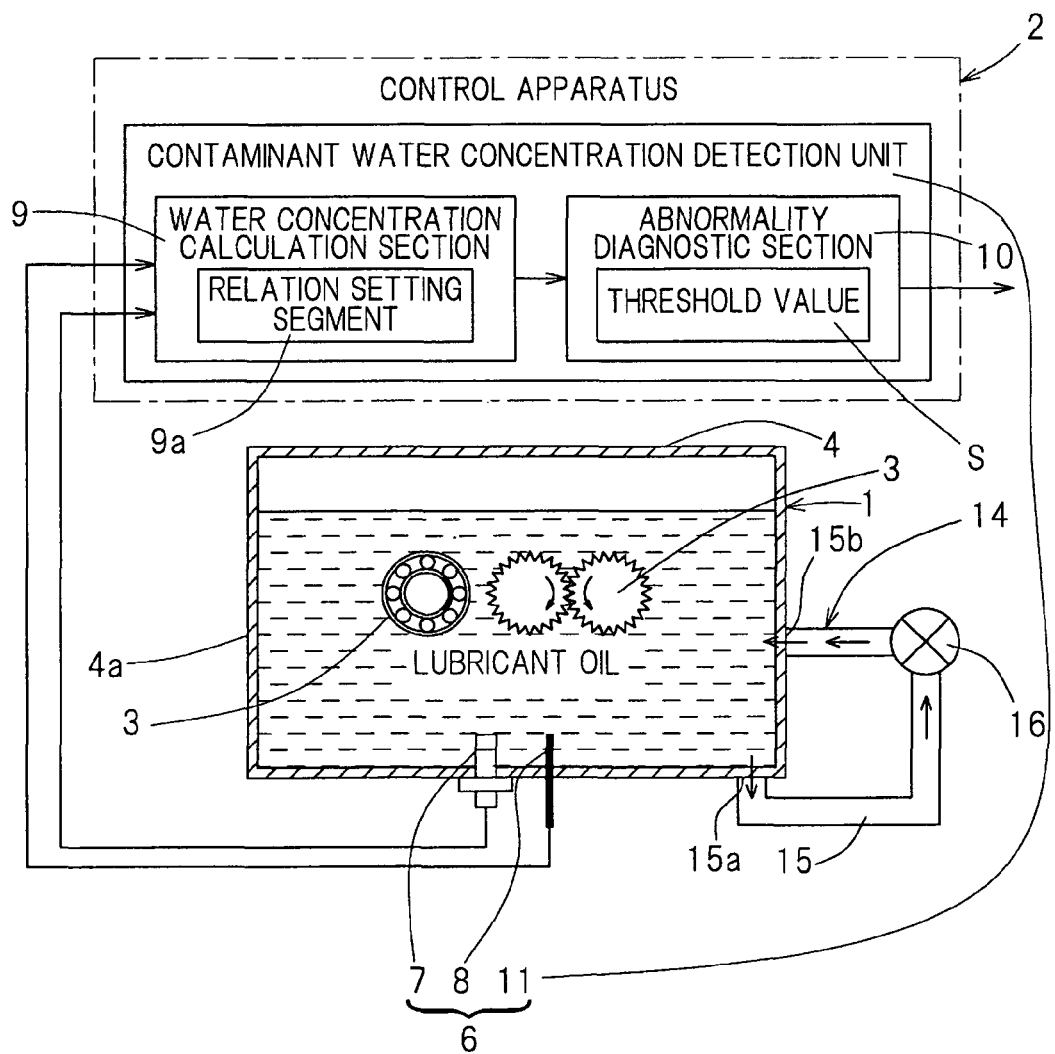
FIG. 4 is a block diagram showing a conceptual construction of the status monitoring system for the rolling device in accordance with a fourth embodiment of the present invention.

A fourth embodiment shown in FIG. 4 is an example of a circulating oiling type, that is, an example in which a circulating oiling mechanism 14 for performing a circulating oiling for the lubricant oil reservoir 4a in the housing 4 is provided. The circulating oiling mechanism 14 includes an oil circulating passage 15 such as, for example, a tube, having its opposite ends communicated with the lubricant oil reservoir 4a, and a pump 16 for circulating the lubricant oil 5 through the oil circulating passage 15. The oil circulating passage 15 is communicated with a discharge port 15a defined at a bottom of the lubricant oil reservoir 4a, and an oil supply port 15b defined at an intermediate heightwise position or an upper portion of the lubricant oil reservoir 4a. Other structural features and effects of the fourth embodiment than those described above are similar to those shown in and described in connection with the first embodiment shown in FIG. 1.

Figure 5:
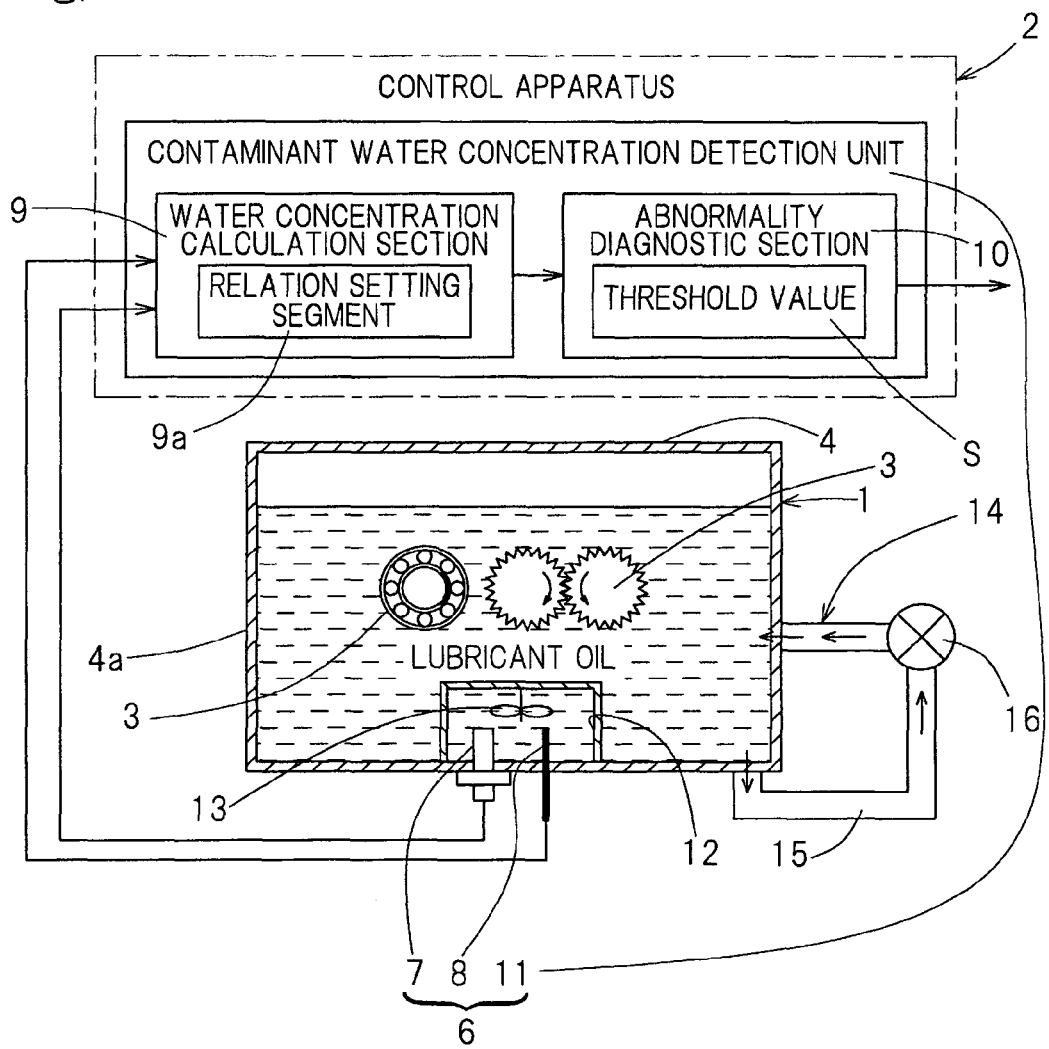
FIG. 5 is a block diagram showing a conceptual construction of the status monitoring system for the rolling device in accordance with a fifth embodiment of the present invention.

A fifth embodiment shown in FIG. 5 is an example in which, in the circulating oiling type, the measurement chamber 12 communicated with the lubricant oil reservoir 4a is provided in an inner portion of the housing 4 and the electrostatic capacitance detector 7 and the oil temperature measuring instrument 8 are so arranged as to measure, respectively, the electrostatic capacitance and the oil temperature within the measurement chamber 12. Even in this case, the stirrer 13 for stirring the lubricant oil 5 within the measurement chamber 12 may be provided. Other structural features and effects of the fifth embodiment shown in FIG. 5 than those described above are similar to those shown in and described in connection with the fourth embodiment shown in FIG. 4.

Figure 6:
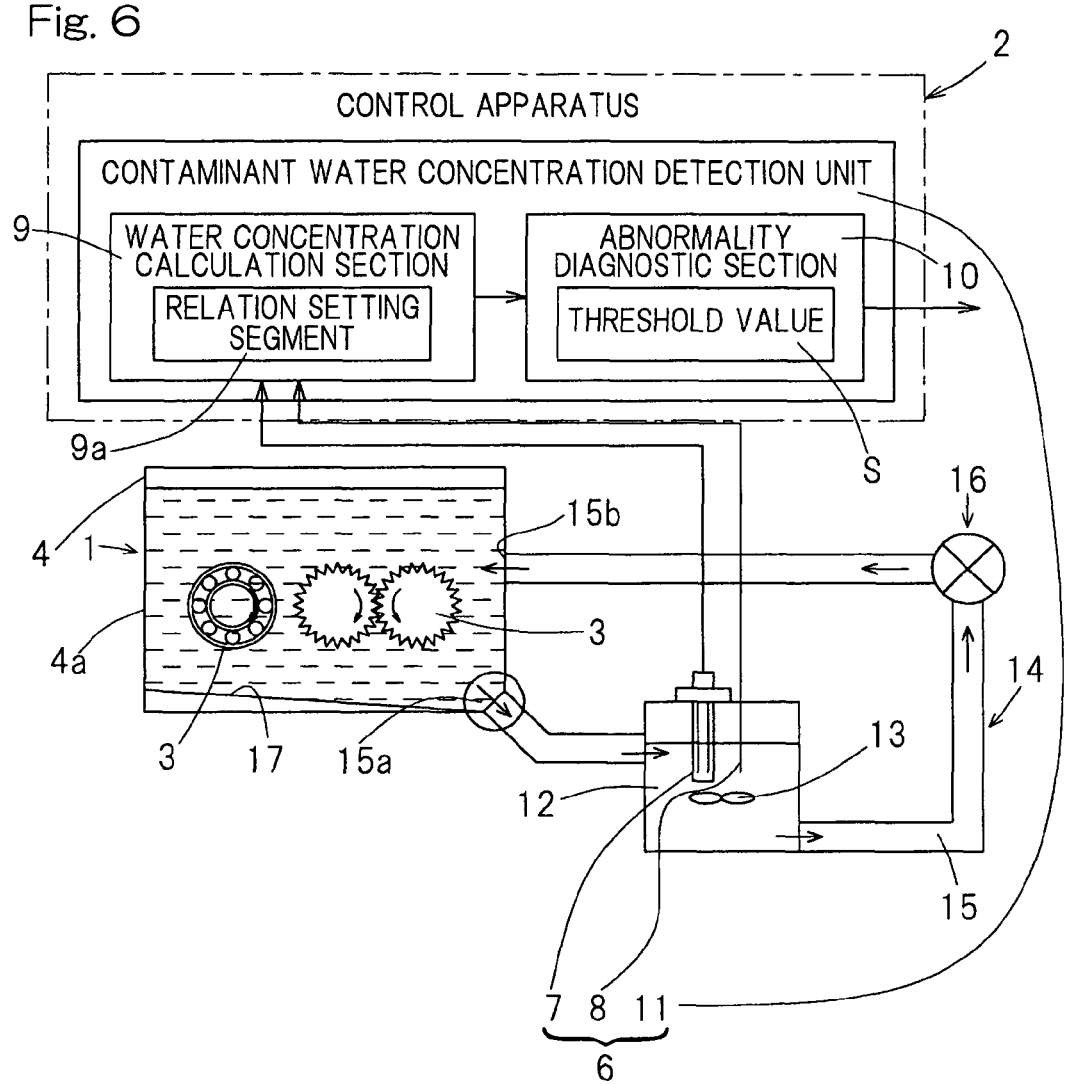
FIG. 6 is a block diagram showing a conceptual construction of the status monitoring system for the rolling device in accordance with a sixth embodiment of the present invention.

A sixth embodiment shown in FIG. 6 is an example in which in the circulating oiling type the measurement chamber 12 is provided outside of the housing 4. The measurement chamber 12 is provided on the oil circulating passage 15. In this measurement chamber 12, the electrostatic capacitance detector 7 and the oil temperature detecting unit 8 for measuring the electrostatic capacitance and the oil temperature of the lubricant oil therein are provided and the stirrer 13 for stirring the lubricant oil 5 within the measurement chamber 12 is also provided. The provision of the stirrer 13 this way is effective to stably accurately measure the electrostatic capacitance and to determine accurately the contaminant water concentration.

Also, in this sixth embodiment, an inclined groove is provided at the bottom of the lubricant oil reservoir 4a. One end of a bottom surface of the inclined groove 17 on a lower side is formed as the discharge port 15a for the lubricant oil and while the lubricant oil 5 is regularly pumped into the measurement chamber 12, which serves as a reserve tank equipped with the stirrer 13, by means of a pump 16 so that the electrostatic capacitance and the oil temperature may be measured there to monitor the contaminant water concentration. By so doing, even though water having a specific gravity higher than that of the lubricant oil is separated, the water can be captured into the measurement chamber 12 and the contaminant water concentration on a high side can therefore be measured. In other words, monitoring on safer side can be accomplished. In this sixth embodiment, other structural features and effects than those described above are similar to those shown in and described in connection with the first embodiment shown in FIG. 1.

Figure 7:
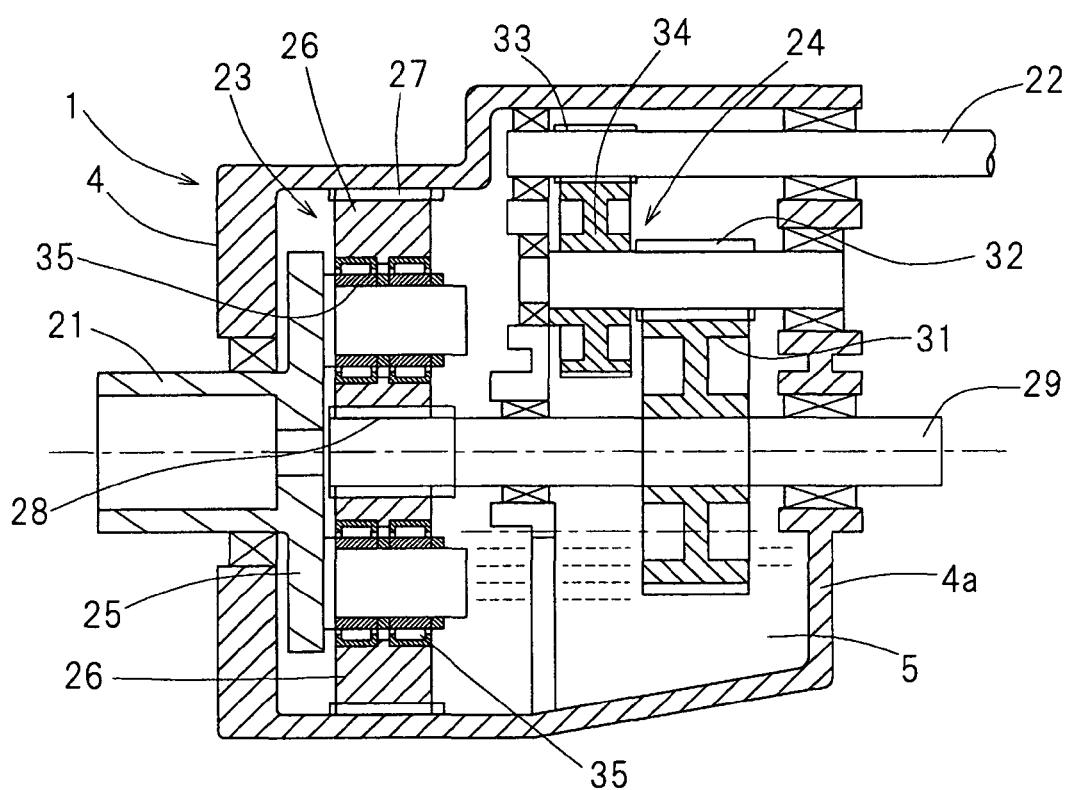
FIG. 7 is a longitudinal sectional view showing one example which will be a specific example of the rolling device.

FIG. 7 illustrates one specific example of the rolling device 1. The rolling device 1 shown therein is a speed-increasing gear assembly employed in a wind turbine generator. This rolling device 1 is of a type including a planetary gear mechanism 23, which forms a primary speed-increasing gear assembly, and a secondary speed-increasing gear assembly 24 both provided between an input shaft 21 and an output shaft 22. The planetary gear mechanism 23 is of a structure in which a planetary gear 26 is mounted on a carrier 25, which is integral with the input shaft 21, the planetary gear 26 is meshed with an internal ring gear 27 and a sun gear 28 and a shaft integral with the sun gear 28 is rendered to be an intermediate output shaft 29. The secondary speed-increasing gear assembly 24 is comprised of a gear train for transmitting a rotation of the intermediate output shaft 29 to the output shaft 22 through a plurality of gears 31, 32, 33 and 34. The planetary gear 26 referred to above, as well as various rolling component parts which will become a bearing assembly 35 for supporting the planetary gear 26, the ring gear 27 and the gear 31 of the secondary speed-increasing gear assembly 24, is immersed into the lubricant oil 5 within the lubricant oil reservoir 4a in the housing 4 as shown in FIG. 1. The lubricant oil reservoir 4a is circulated by a circulating oiling mechanism (not shown) comprised of a pump and a tubing. It is, however, to be noted that the circulating oiling mechanism may not be necessarily provided and alternatively it may be an oil bath circulating type.

In the status monitoring system for the rolling device, which is designed in accordance with any one of the foregoing embodiments, a testing method for determining the proper threshold value S that is to be set in the abnormality diagnostic section 10 will be described in detail. One example of a testing apparatus used to practice this testing method is shown in a conceptual diagram in FIG. 8. This rolling slide fatigue life testing apparatus is made up of a testing apparatus main body 140, a testing equipment main body control apparatus 141 for controlling the testing apparatus main body 140, and a water concentration calculation section 142. The testing apparatus main body 140 includes a test oil bath 101 in which a lubricant oil 5A is filled in such a fashion that a rolling component part simulation product 3, which is an object to be tested, is immersed, a simulated rolling component part drive device 120 for actuating the rolling component part simulation product 3 within the test oil bath 101, a syringe pump 104 which is a water injector for injecting water into the lubricant oil within the test oil bath 101, an electrostatic capacitance meter 105 which is an electrostatic capacitance measuring instrument for measuring the electrostatic capacitance of the lubricant oil 5A within the test oil bath 101, and a thermocouple 106 which is an oil temperature measuring instrument for measuring the oil temperature of the lubricant oil 5A within the test oil bath 101.

The rolling component part simulation product 3 is a rolling component part, in which an object to be tested made of a material for a rolling component part made of a steel material is included as a constituent element, which component is simulated for testing purpose. In the example as shown, the rolling component part simulation product 3 is the one that simulates a thrust bearing assembly which is one kind of rolling component parts, and includes a plurality of rolling elements 3c in the form of balls interposed between an inner ring 3a and an outer ring 3b with the outer ring 3b constituting the object to be tested. The outer ring 3b of the rolling component part simulation product, which is the object to be tested, is of a cylindrical shape having an end face defining a rolling surface. Also, this rolling component part simulation product 3 has the rolling elements 3c of a larger size as compared with those in the thrust bearing assembly which is an actual rolling component part. In the actual thrust bearing assembly, which forms an object to be simulated, since the rolling elements are too small and application of even a slight load results in a marked increase of the maximum surface pressure of a contact surface, in the rolling component part simulation product the rolling elements 3c were made in larger size. The inner ring 3a is employed in the form of a specially made inner ring having a groove in which such larger rolling elements 3 can roll.

The water concentration calculation section 142 is capable of calculating the contaminant water concentration in the previously described lubricant oil in accordance with the predetermined rule from the electrostatic capacitance, measured by the electrostatic capacitance meter 105, and the oil temperature measured by the thermocouple 106. The water concentration calculation section 142 has a relation setting segment 143 in which relations between the electrostatic capacitance and the oil temperature and the mixed water concentration are set by computing formulas and/or tables, and calculates the contaminant water concentration based on the electrostatic capacitance and the oil temperature both inputted with the use of a rule defined in the relation setting segment 143.

The testing equipment main body control apparatus 141 includes a rolling component part simulation product control section 144 for controlling the rolling component part simulation product drive device 120, a pump control section 145 for controlling the syringe pump 104, and a control section (not shown) for controlling the testing apparatus main body 140 and other drive portions. The testing equipment main body control apparatus 141 is a computer type sequencer or a numerical control apparatus and is comprised of a computer such as, for example, a personal computer or the like and a program executed thereby.

The water concentration calculation section 142 is comprised of a computer such as, for example, a personal computer or the like and a program executed thereby. The water concentration calculation section 142 may be employed in the form of either a computer forming the testing equipment main body control apparatus 141 or a computer independent from the testing equipment main body control apparatus 141.

This rolling slide fatigue life testing method is carried out in the following manner with the use of the testing apparatus of the construction described hereinabove. The rolling component part simulation product 3, which is the object to be tested, is immersed into the lubricant oil 5A accommodated within the test oil bath 101 and is actuated to perform a testing of a rolling slide fatigue life of the outer ring 3b, which is the object to be tested forming the rolling component part simulation product 3. In the instance now under discussion, with the use of the syringe pump 104, water as a source of hydrogen is injected into the lubricant oil 5A, and the contaminant water concentration in the lubricant oil 5A is measured with the use of the water concentration calculation section 142 based on the electrostatic capacitance of the lubricant oil 5A, which is measured by the electrostatic capacitance meter 105, and the oil temperature, which is measured by the thermocouple 106.

In the testing apparatus shown therein, as a mechanism for supplying the lubricant oil 5A into the test oil bath 101, an oil bath lubricating mechanism is employed and the contaminant water concentration in the lubricant oil 5A within the test oil bath 101 is measured. The term "oil bath lubricating mechanism" refers to a mechanism for lubricating, while the lubricant oil is accumulated within the test oil bath 101, the rolling component part simulation product with the lubricant oil so accumulated therein. The measured contaminant water concentration is fed back to the syringe pump 104 to change the amount of water injected so that the contaminant water concentration can be controlled. In other words, the pump control section 145 referred to above causes the injection rate by the syringe pump 104 to be changed so that the contaminant water concentration may fall within a predetermined range in accordance with a predetermined rule in dependence on the contaminant water concentration outputted by the water concentration calculation section.

Also, an electric current is supplied by an electric conduction device 147 so as to flow between contact elements (specifically, a pair of the raceway rings 3a and 3b) of the rolling component part simulation product 3 to measure the metal contact interval. A main shaft 107 of a servomotor 107A in the rolling component part simulation product drive device 120 and a spindle 108 for actuating the rolling component part simulation product 3 when connected with the inner ring 3a, which will become a constituent element of the rolling component part simulation product 3, are connected directly with each other to perform a rocking motion. The spindle 108 may have the rolling component part simulation product as one of the constituent elements. The main shaft 107 of the servomotor and the spindle 108 are connected with each other by means of an insulation coupling 132. Support bearings for the spindle 108 utilize ceramic rolling element bearings 133.

Figure 8:
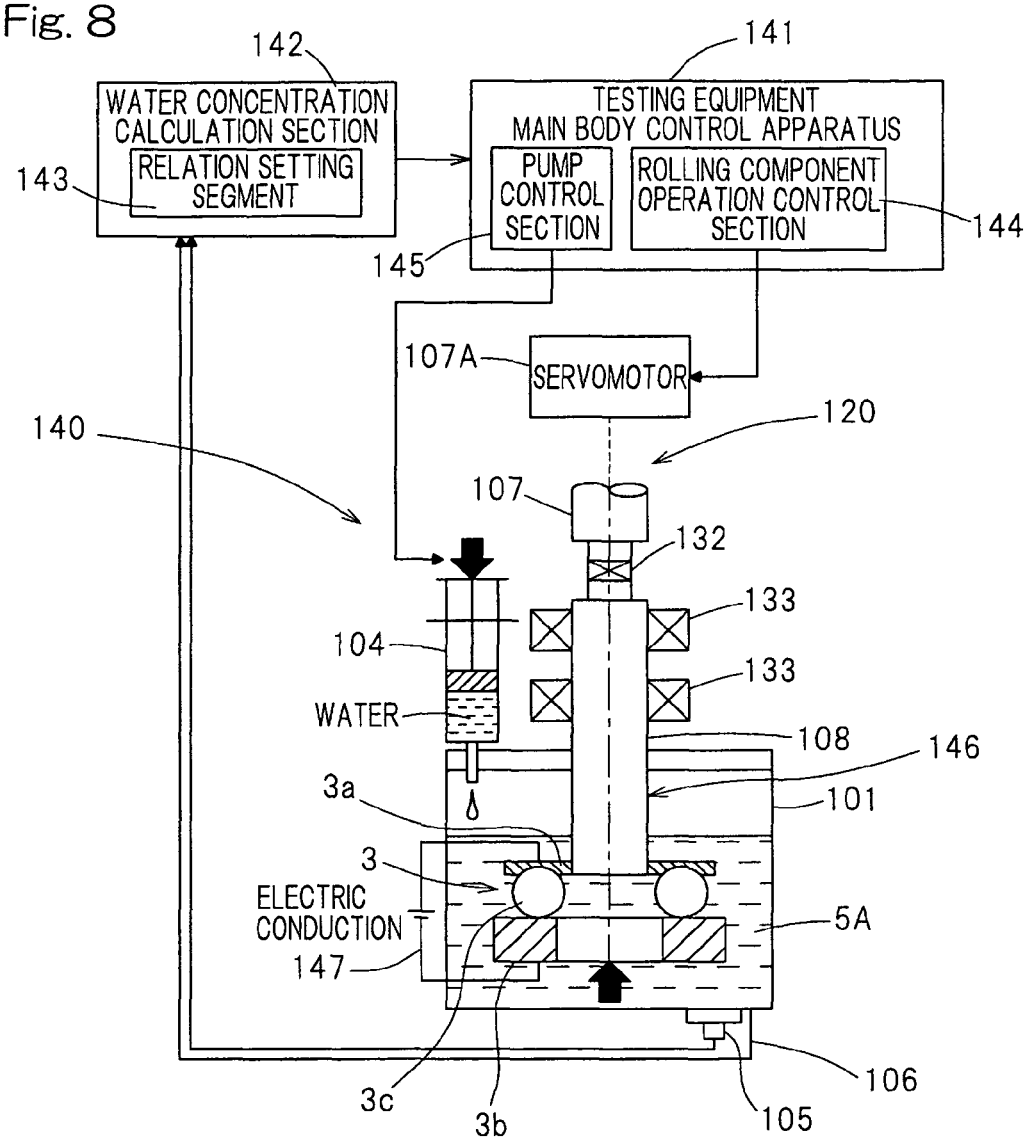
FIG. 8 is a conceptual diagram showing one example of a testing apparatus used in the practice of a rolling and sliding fatigue life testing method for determining a proper threshold value determined by an abnormality diagnostic threshold value setting method that utilizes the status monitoring system for the rolling device in accordance with any one of the foregoing embodiments.

As hereinbefore described, the rolling component part simulation product 3 is rendered to be a component simulating a thrust ball bearing assembly in the instance as shown in FIG. 8 and the outer ring 3b, which will form the object to be tested, is fixedly placed on a support table (not shown) or the like and the inner ring 3a is fixed to the spindle 108.

With the spindle 108 referred to above and the ceramic rolling element bearings 133, a head portion 146 of the rolling element simulated body drive device 120 is formed. The head portion 146 is represented by a mechanism sections that actuate one or a set of rolling component part simulated bodies 3. In the illustrated embodiment only one head portion 146 is employed, but a plurality of head portions 146 may be employed to enable a plurality of rolling component part simulated bodies 3 to be tested simultaneously.

In the meantime, in the anti-hydrogen brittleness evaluation in the rolling slide fatigue life test, it is not possible to control the inversion concentration of diffusible hydrogen in the steel material. Also, it is a accelerated test conducted under severe conditions and does not simulate actual operation conditions. Regarding the anti-hydrogen brittleness evaluation of the steel material, the evaluation with the inversion concentration of the diffusible hydrogen being controlled is made available. In contrast thereto, the anti-hydrogen brittleness evaluation such as, for example, the type of lubricant oil, additives to the lubricant oil, a surface treatment applied to a contact surface of the contact element and others need be evaluated through the rolling slide fatigue life test in which, as is the case with this embodiment, the inversion concentration of the diffusible hydrogen cannot be controlled. Accordingly, by means of the rolling slide fatigue life test which simulates the actual machine as faithfully as possible with disturbances as minimized as possible, the rolling slide fatigue life testing method in accordance with this embodiment is effective in efficiently initiating the premature damage originating from the hydrogen brittleness so that antidote elements appropriate to conditions of use may be assessed. It is to be noted that, from the standpoint of acquiring the understanding from users, it is desirable to perform the anti-hydrogen brittleness evaluation of the steel material through the rolling slide fatigue life test.

Considering the conditions of use of various rolling component parts that lead to the premature damage originating from the hydrogen brittleness, the rolling slide fatigue life test having the following functions (1) to (5) is desirable. It is, however, to be noted that in order to avoid influences on head portions 146 in the testing apparatus, although in FIG. 8, the oil bath lubrication mechanism is employed for each of the head portions, a circulating oiling mechanism may be employed. Regardless of whether the oil bath lubrication mechanism is employed or whether the circulating oiling mechanism is employed, tests can be conducted with different conditions for each of the head portions provided that it is provided in each of the head portions.

(1) Water as a source of hydrogen is injected into the lubricant oil 5A.

(2) The contaminant water concentration in the lubricant oil 5A is monitored based on the electrostatic capacitance and the oil temperature.

(3) The contaminant water concentration monitored as in (2) above is fed back and the contaminant water concentration is controlled by changing the amount of water injected.

(4) In addition to a constant rotational speed and one direction rotation operation, an accelerated and decelerated operation and a rocking motion can be accomplished.

(5) An electric conduction can be accomplished.

Regarding the function (1) above, although there is a method of regularly replacing a lubricant oil containing water mixed therein, it is not good in efficiency because of an increased number of works required, the incapability of performing the replacing on holidays and others. For this reason, as shown in FIG. 8, it is desirable to inject the water by means of the syringe pump 104 or a tube pump. The syringe pump 104 is better suited for a microinjection. In the testing apparatus of FIG. 8 which utilizes the oil bath lubrication mechanism in the head portion 146, the site of injection of water is the test oil bath 101, while the test oil bath 101 or a circulating oiling portion of the circulating oiling mechanism is chosen where the circulating oiling mechanism is used in the head portion 146.

Where the function (2) above is employed, it should be noted that the saturated water concentration of the lubricant oil of a mineral oil type with no additive employed is at most 200 weight ppm. While the contaminant water concentration can be measured based on the electrostatic capacitance and the oil temperature, the electrostatic capacitance meter 105 for measuring the electrostatic capacitance is broadly classified into the following two types. One of them is a type that can measure to a value equal to or lower than the saturated water concentration and the remaining type is a type that can measure to a value in excess of the saturated water concentration and even when water becomes clouded. While the former type is more generally used, the latter includes a type capable of measuring the contaminant water concentration in excess of 10% or higher. As hereinabove described, the saturated water concentration of the lubricant oil of the mineral oil type is at most 200 weight ppm. According to the rolling slide fatigue life test, in which the water mixed oil of 200 weight ppm in concentration is regularly replaced, it is reported that no influence of water is found. Although the saturated water concentration of the mineral oil type that is free from any additive is minute, the saturated water concentration will become markedly high with the lubricant oil of a synthesized oil type and, even with the mineral oil based lubricant oil depending on the type of an additive used. The electrostatic capacitance meter capable of only measuring the contaminant water concentration of a value lower than the saturated water concentration can be used to measure the saturated water concentration in the lubricant oil 5A. If the relation between the contaminant water concentration and the rolling slide fatigue life is determined, there is the possibility that the saturated water concentration peculiar to the lubricant oil may be one of indications of the anti-hydrogen brittleness.

With respect to the function (3) above, even when water of a constant concentration admixes in the lubricant oil 5A and the rolling slide life test is conducted as a macroscopically closed system, the contaminant water concentration markedly decreases after a lapse of about three hours. Even where water is continuously injected into the lubricant oil 5A at a constant flow, it can be easily imagined that the contaminant water concentration will change. While water is injected as the source of hydrogen because of the requirement for the function (1) above, for that purpose it is desirable that the contaminant water concentration monitored by the electrostatic capacitance and the oil temperature as required by the function (2) above is fed back so that the amount of the water injected can be changed to enable the contaminant water concentration to be maintained within the predetermined range.

Figure 9:
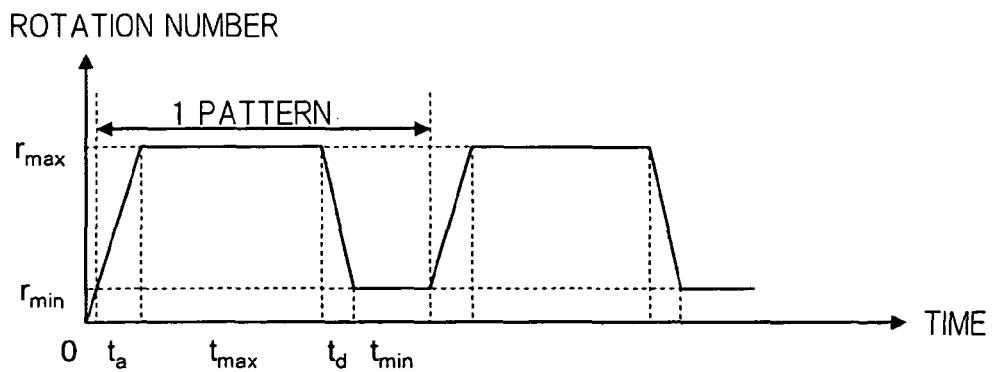
FIG. 9 is a pattern diagram showing an example of a minimum pattern setting for acceleration and deceleration taking in the practice of the above testing method.

When it comes to the function (4) above, the actual rolling component part 3 is not used at a constant rotational speed under one direction rotation. Because of it, it is desirable that other than the constant rotational speed and one direction rotation, it can undergo an accelerated and decelerated operation and a rocking motion. As for the accelerated and decelerated operation, there is the necessity that it can be set at least to such a pattern as shown in FIG. 9. That is to say, six parameters including the acceleration $(r_{max}-r_{min})/t_a$, a high speed rotational number $r_{max}$, the retention time $t_{max}$ at the high speed rotational number, the deceleration $(r_{max}-r_{min})/t_d$, a low speed rotational number $r_{min}$ and the retention time $t_{min}$ at the low speed rotational number can be arbitrarily set and, taking it as one pattern, acceleration and deceleration are repeated. In the rocking motion, unlike the case with the rotation, vibration does not change markedly even though damage occurs. In the rocking motion caused by a crank mechanism, since the vibration thereof is superposed, it is difficult to detect through the vibration when the damage occurs. In order to enable the damage to be accurately detected based on the vibration, there is the necessity that the rocking motion is effected by directly connecting the main shaft 107 of the servomotor with the spindle 108 of the testing mechanism, which includes the rolling component part simulation product 3 as one of the constituent components, and then effecting the rocking motion, so that a superposed vibration component can be preferably eliminated. Also, there is the necessity to increase the rigidity of the spindle 108 and others of the testing mechanism as high as possible. For a condition of the rocking motion, it is desirable that the angle and the frequency of rocking can be arbitrarily set.

It is to be noted that if the main shaft 107 of the servomotor and the spindle 108 of the testing mechanism are directly connected with each other, it is difficult to give off a change in speed expressed by a waveform of a trigonometric function such as exhibited by the crank mechanism. In order to enable it, it is recommended to control an amplifier for the servomotor by means of a program for the sequencer.

The purpose of use of the function (5) above lies in the following two points. One of them is to measure the metal contact interval of the contact surface with a weak electric current supplied so as to flow between the contact elements of the rolling component part simulation product 3. The other of them is to frictionally wear a positive pole side with a large electric current of about 1 A supplied between the contact elements. By the utilization of this phenomenon and by placing the test piece on the positive pole side, a newly-formed metal surface can be intentionally caused to appear in the contact portion of the test piece to facilitate generation and inversion of hydrogen. This is also addressed in the non-patent document 9 listed hereinbefore.

In the rolling slide fatigue life testing method that utilizes the testing apparatus shown in FIG. 8 all of the functions (1) to (5) above are satisfied and, on the assumption that the rolling component part simulation product 3 undergoes the rocking operation, a mechanism is employed in which the main shaft 107 of the servomotor 107A and the spindle 108 of the testing mechanism are directly connected with each other. It is to be noted that where no rocking operation is necessary, it is rather preferred that rather than the servomotor, which is expensive and has a rated rotational number of 3,000 rpm at most, an inexpensive induction motor or the like is used to drive the spindle 108 of the testing mechanism through a belt drive system. In this case, when a pulley mechanism is provided in a drive transmitting system, through which the drive of the servomotor 107A is transmitted to the spindle 108, and the pulley ratio is changed, the rotational speed of the spindle 108 of the testing mechanism can be increased and, therefore, it is effective in increasing the speed difference in accelerated and decelerated operation. It is however to be noted that where the circulating oiling mechanism is employed in the head portion 146, the use is desirable of a tube pump or the like, which has a relatively high oiling speed. In this case, in order to the amount of the lubricant oil in the test oil bath 101 at a level as constant as possible, it is desirable that the amounts of the lubricant oil inflowing and outflowing be as constant as possible.

Although in the conceptual diagram of FIG. 8 showing the testing device, the rolling component part simulation product 3 has been shown and described as employed in the form of a thrust bearing type, since even in the case of the thrust bearing type the direction of rotation of steel balls and the direction of revolution of the steel balls are different from each other, a slide occurs in the contact surfaces of the test piece and the steel balls in the rolling component part simulation product 3. Also, in order to apply the slide to the contact surface positively, a motion mechanism of the contact elements may be devised. Where a gear member is to be evaluated as a rolling component part simulation product 3, a further large slide occurs in a gear wheel and, therefore, designing is needed to allow the large slide to act on the contact surface by means of, for example, forcibly changing the difference in peripheral velocity of the test piece and an object that contact the test piece.

Figure 10:
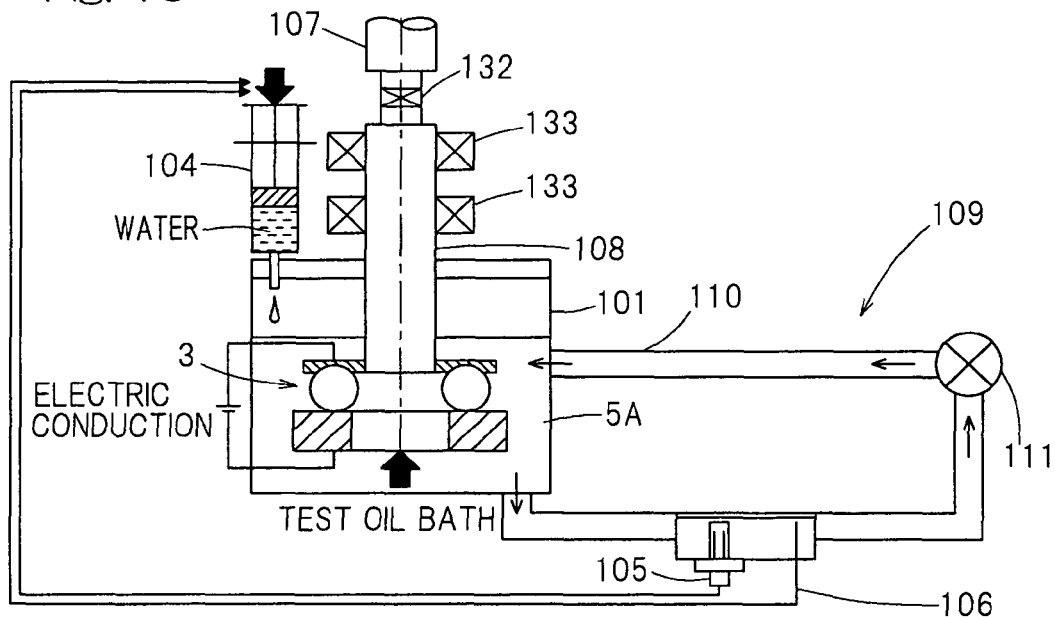
FIG. 10 is a conceptual diagram showing schematically another example of the testing apparatus.
Figure 11:
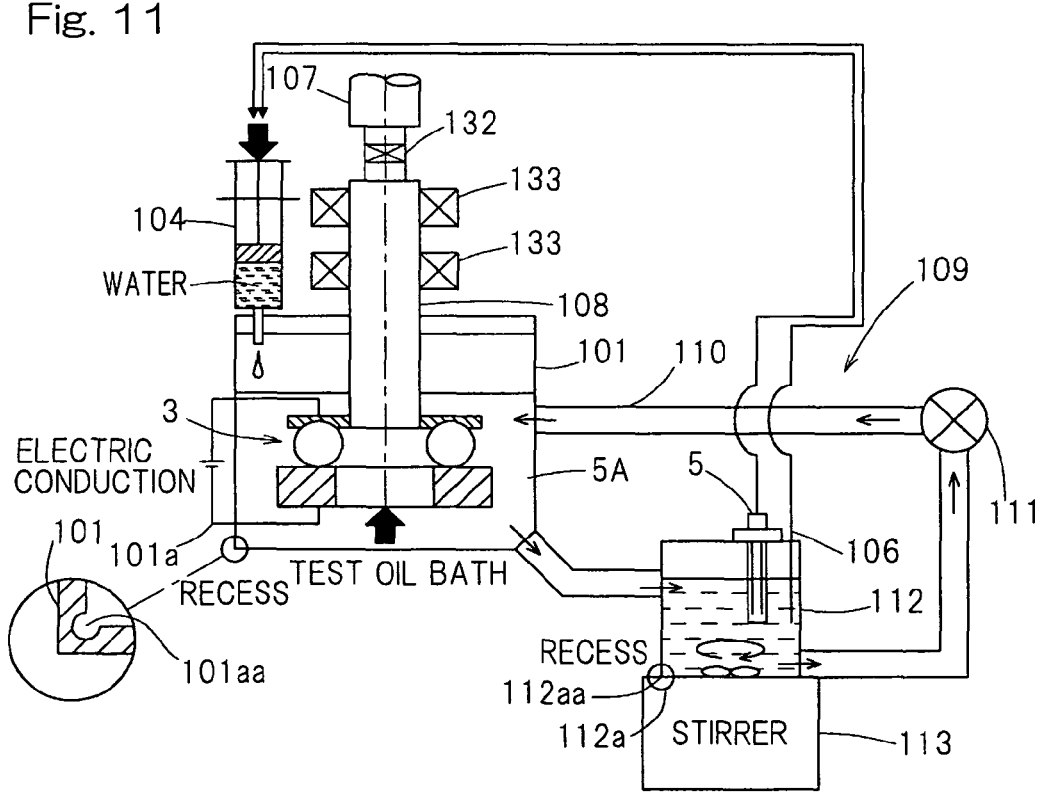
FIG. 11 is a conceptual diagram showing schematically a different example of the testing apparatus.

FIGS. 10 and 11 are conceptual diagrams showing respective examples of the testing device used in the practice of this rolling slide fatigue life testing method. In the case of the testing device shown in FIG. 10, as a mechanism for supplying the lubricant oil 5A into the test oil bath 101, a circulating oiling mechanism 109 is employed. The circulating oiling mechanism 109 employed in this example shown in FIG. 10 includes a circulation pump 111 arranged on a circulating passage 110, an electrostatic capacitance meter 105 and a thermocouple 106. Even in this case, the electrostatic capacitance meter 105 and the thermocouple 106 may be provided in the test oil bath 101.

Here, if the condition of mixing of the water with the lubricant oil 5A is not good, the value of the electrostatic capacitance becomes unstable as the contaminant water concentration increases. Because of it, it is preferred that the electrostatic capacitance is measured while the lubricant oil 5A and the water are in a condition well mixed together. In view of this, in the testing device shown in FIG. 11, the testing device shown in and described with reference to FIG. 10 is modified in such a manner that a reserve tank 112 is provided between a discharge port of the lubricant oil 5A in the test oil bath 101 and the circulation pump 111 so that, while the lubricant oil 5A is accumulated within the reserve tank 112, the lubricant oil 5A can be stirred by a magnetic stirrer 113 and the electrostatic capacitance and the oil temperature can then be measured. The thermocouple 106 is provided in the reserve tank 112. In order for the lubricant oil 5A and the water to be sufficiently mixed together, the capacity of the reserve tank 112 may be reduced to increase a stirring effect. To give an indication, the amount of the lubricant oil is preferably equal to or smaller than 100 mL. What is more preferable is that arrangement should be made to facilitate a discharge of the water, which has a specific gravity higher than the lubricant oil 5A, from the test oil bath 101 and the reserve tank 112. For this purpose, in the testing device shown in FIG. 11, the discharge port of the lubricant oil 5A in each of the test oil bath 101 and the reserve tank 112 is rendered to be a bottom corner portion 101a or 112a (shown by the circle as enlarged in FIG. 11).

Also, it is preferred that the interior of each of the test oil bath 101 and the reserve tank 112 be rendered to be of a cylindrical shape and that a groove shaped recess 101aa or 112aa be provided on an exterior angle side as a so-called recess so as to extend the entire circumference of such bottom corner portion 101a or 112a. By so designing, even an additive having a specific gravity higher than the water can become easily circulated.

While in the testing method utilizing the testing device shown in any one of FIGS. 8, 10 and 11 water has been shown and described as injected into the test oil bath 101 with the use of the syringe pump 104, specific examples of the rolling slide fatigue life testing method which is conducted by regularly replacing the water mixed oil within the test oil bath 101 will be described hereinafter.

Figure 12A:
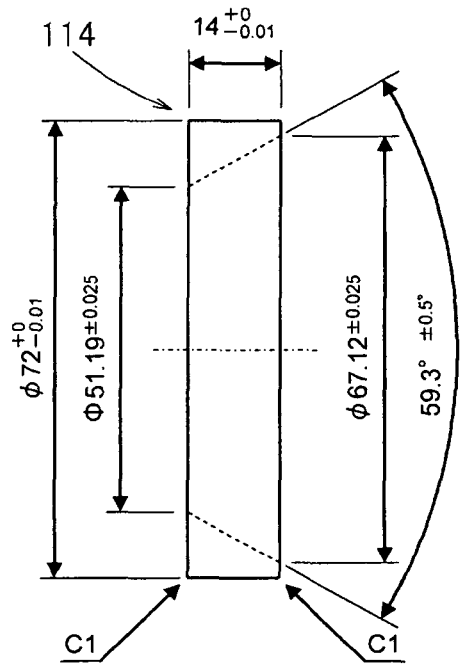
FIG. 12A is a front elevational view showing one example of a test piece forming a rolling component part simulation product that is used in the practice of the above testing method.

Using a bearing steel SUJ2, a tapered outer ring test piece 114 shown in FIG. 12A (finished by grinding after a heat treatment, the surface roughness Rq of an inner diametric raceway surface being Rq≈0.03 μm) was prepared. The heat treatment is carried out by heating the test piece under an atmosphere of RX gas at 850° C. for 50 minutes and then quenched, followed by tempering at 180° C. for 120 minutes. The test was conducted on a rolling component part simulation product 3 comprised of the tapered outer ring test piece 114 combined with an inner ring 115 (a standard quenched and tempered product of SUJ2) of an angular ball bearing 7306B, thirteen steel balls 116 (standard quenched and tempered products of SUJ2) and a retainer 117. The tapered outer ring test piece 114 was tapered in shape because, when rotated in contact with the steel balls 116 at a contact angle, the steel balls 116 would spin to slide on a surface of contact with the outer ring test piece 114. If the slide occurs, the frequency of occurrence of the premature damage originating from the hydrogen brittleness will become high.

Figure 12B:
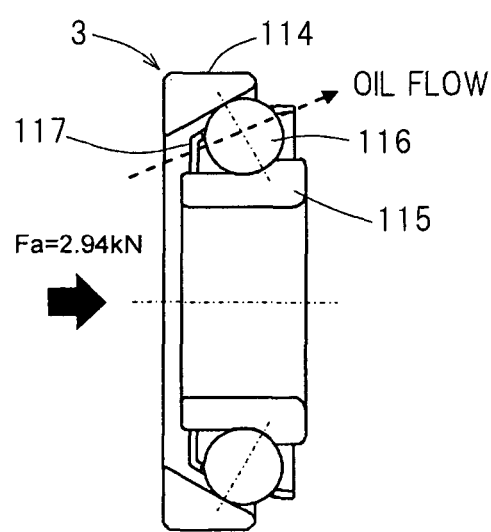
FIG. 12B is a longitudinal sectional view showing the rolling component part simulation product having the test piece incorporated therein.
Figure 13:
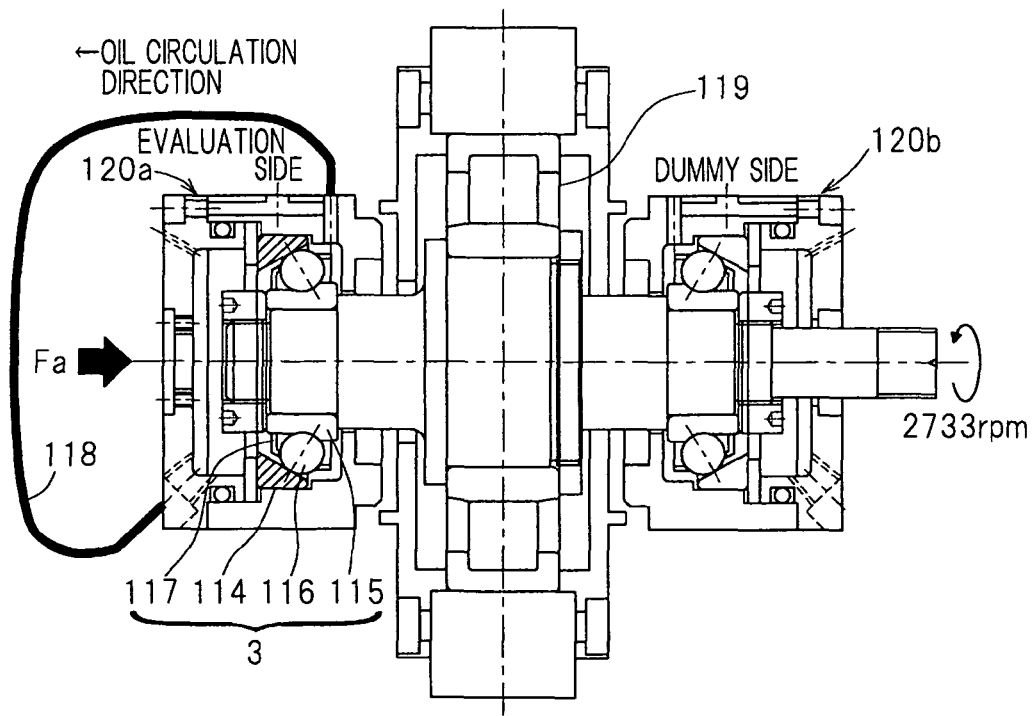
FIG. 13 is a longitudinal sectional view showing a testing apparatus used to test the test piece of the rolling component part simulation product shown in FIGS. 12A and 12B.

FIG. 13 illustrates schematically the testing device used in the practice of the testing method according to this specific example. In this figure, a mechanism section shown on a left side thereof represents an evaluation side portion 120a and a mechanism section on a right side is a dummy side portion 120b. In this figure, the outer ring test piece 114 of the tapered shape, which is an object to be damaged, is shown by the hatching. Only an axial load Fa=2.94 kN was applied and the inner ring 115 was rotated at 2,733 min$^{-1}$. An additive free turbine oil of VG100 (having a density of 0.887 g/cm$^3$ and a kinetic viscosity of 100.9 mm$^2$/s @ 40° C. and 11.68 mm$^2$/s @ 100° C.) was used for the lubricant oil and 200 weight ppm, of 5 wt % purified water was mixed in such lubricant oil. On the evaluation side 60 mL of a water mixed oil was charged an inlet (a lower side) and an outlet (an upper side) for the lubricant oil was connected together by means of a tube 118 to form a closed system. Since a flow of the lubricant oil occurs by a pumping action in a direction shown by the arrow in FIG. 12B, the water mixed oil is circulated and stirred. The test was continued for 20 hours and, unless any damage occurred during the testing hours, it was replaced with a newly prepared water mixed oil. The 20 hour test and the replacement of the water mixed oil were repeated until the damage occurred. The detection of the damage was carried with the use of a vibration gauge. It is to be noted that a cylindrical roller bearing 119 at the center of the testing device shown in FIG. 13 is used to apply the radial load and has no concern with the test in any way whatsoever.

The maximum contact surface pressure between the outer ring test piece 114 and the steel ball 116, which was obtained by means of a elastic Hertzian contact calculation when only the axial load Fa=2.94 IN was applied was found to be 3 GPa. In the elastic Hertzian contact calculation, the Yong's modulus E and the Poisson's ratio v were E=204 GPa and v=0.3 which were respective actually measured values of the SUJ2 standard quenched and tempered product. An oil film parameter between the outer ring test piece 114 of the tapered shape and the steel ball 116 in the elasto-hydrodynamic lubrication calculation in disregard for the water admixture was about 3. It is, however, to be noted that the surface roughness of the steel ball 116 was fixed constantly at an actually measured value of Rq=0.0178 μm. The calculated life L10h of the tapered outer ring test piece 114 itself was 2,611 hours when calculated having been converted into a two cylinder model. The method of determining the calculated life L10h is disclosed in the non-patent document 10 referred to previously. It is to be noted that influences resulting from a slide have been disregarded.

Figure 14:
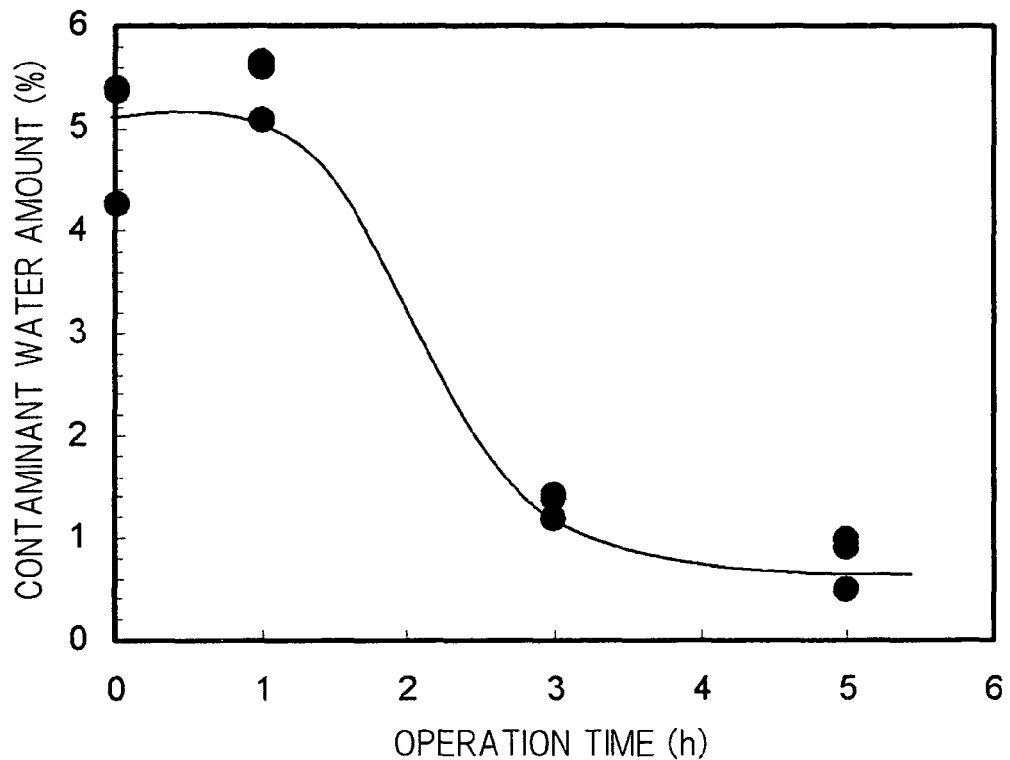
FIG. 14 is a chart showing a change in amount of mixed water measured by the test referred to above.

During the test in which the initial contaminant water concentration was 5 wt %, a small amount of the lubricant oil was regularly sampled and the chronological change was examined by measuring the contaminant water concentration by means of a coulometric titration. As a result, as shown in the chart of FIG. 14, the contaminant water concentration has been found markedly decreasing after a lapse of about 3 hours. In spite of the closed system as discussed above, it is macroscopic and it is impossible to eliminate any gap completely. It is suspected that a water component has evaporated through a minute gap that is not noticeable. The result of this rolling slide fatigue test is such as shown in the following Table 1.

TABLE 1

Result of Rolling Slide Fatigue Life Test with Regularly Replaced Water mixed Oil

| Mixed Water Amt. | Exfoliation Life (ascending order) | | | | | Remarks |
|---|---|---|---|---|---|---|
| 200 wt. ppm | 1000 | 1000 | 1000 | 1000 | 1000 | All terminated |
| 5 wt. % | 24.5 | 63.5 | 80.1 | 112.4 | 148.9 | Exfoliation occurred in all test pieces |

In the case of 5 wt. % in admixed water amount: $L_{10}$ = 23.0 h, $L_{50}$ = 79.3 h, e = 1.52

In the case of the water mixed oil of 200 wt.ppm, no damage occurred in all of the five test pieces up to 1,000 hours and the test was then terminated. On the other hand, in the case of the water mixed oil of 5 wt. %, the premature damage occurred in all five test pieces in the order of 1/100 of the calculated life. The form of damage in the test piece was an internally originated exfoliation with the starting point lying on a surface layer. It is to be noted that although the maximum contact surface pressure of 3 GPa acts even on the SUJ2 steel ball 116, no exfoliation was occurred. It is suspected that it is because the steel ball 116 is large in effective load volume as compared with the tapered outer ring test piece 114. With the water mixed in a quantity about equal to the upper limit of the saturated water concentration of the lubricant oil used on this occasion, it can be said that there was no influence brought about by the water on the life. On the other hand, where a large amount of water mixes, it may be suspected that hydrogen generates and, consequent upon intrusion into the steel material, an internally originated exfoliation occurred distinctly prematurely. In Table 1 above, the life when the 5 wt. % water mixed oil was regularly replaced was applied to the two parameter Weibull distribution to determine L10, L50 and e (Weibull slope).

A specific example of the rolling slide fatigue life testing method, in which a small amount of water was injected at a constant flow into the lubricant oil 5A within the test oil bath 101 as is the case with the testing device shown in any one of FIGS. 8, 10 and 11 will now be described.

Using the test piece 114, which is the same as that used in the previously described testing method and shown in FIGS. 12A and 12B, and the testing device shown in FIG. 13, and also using the same load condition and the rotational speed, 60 mL of the same lubricant oil (with no water mixed) was charged and the inlet (the lower side) and the outlet (the upper side) for the lubricant oil was connected together by means of the tube 118 to form the closed system. Simultaneous with the start of the test, a continuous injection of a purified water was initiated halfway from the tube 118 by means of the syringe pump 104 shown in FIG. 8. The speed of injection of the pure water was chosen to be 0.5 mL/h. In this case, the chronological change of the contaminant water concentration was not measured, but from the result shown in the chart of FIG. 14, it can be suspected that even in this case the contaminant water concentration underwent a change. The result of this rolling slide fatigue life test is such as shown in the following Table 2.

TABLE 2

Result of Rolling Slide Fatigue Life Test with Water Charged in a Small Amount at Constant Flow

| Water Injection Rate | Exfoliation Life (ascending order) | | | | | Remarks |
|---|---|---|---|---|---|---|
| 0.5 mL/h | 38.6 | 39.2 | 49.6 | 49.9 | 80.5 | 80.7 All test pieces exfoliated |

$L_{10}$ = 32.9 h, $L_{50}$ = 55.9 h, e = 3.55

Even in this case, the premature damage of a life similar to that exhibited when the 5 wt. % water mixed oil was regularly replaced in the previously described testing method, occurred in all of the six test pieces. The form of damage was similarly an internally originated exfoliation with the starting point lying on a surface layer. Also, even in this case, although the maximum contact surface pressure of 3 GPa acts even on the SUJ2 steel ball 16, no exfoliation was occurred. In Table 2 above, L10, L50 and e (Weibull slope) determined by applying the life to the two parameter Weibull distribution are also shown.

In the description that follows, a specific example of measurement, in which the saturated water concentration and the contaminant water concentration in the lubricant oil were determined with the use of the electrostatic capacitance meter 105, will be described. As hereinbefore described, the contaminant water concentration in the lubricant oil can be measured based on the electrostatic capacitance and the temperature, and the electrostatic capacitance meter 105 used to measure it can be broadly classified into two types: One of them is a type merely capable of measuring a value below the saturated water concentration and the other is a type capable of measuring a value in excess of the saturated water concentration and even when water becomes clouded.

Figure 15:
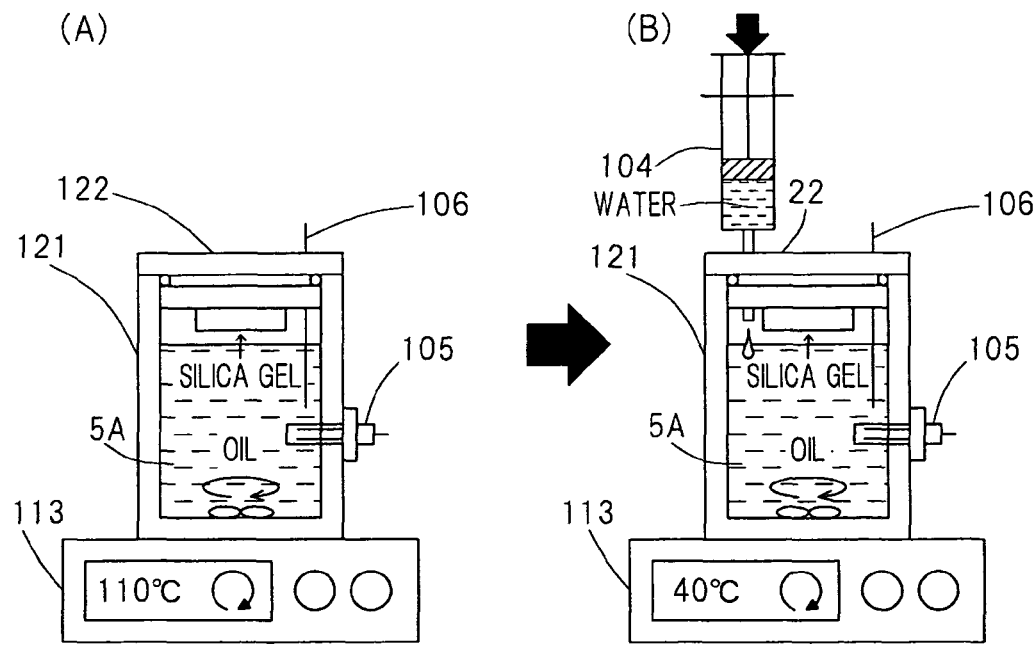
FIG. 15 shows a front elevational view (A) and a longitudinal sectional view (B) showing schematically a testing apparatus used in measuring the saturated water concentration of the lubricant oil.
Figure 16:
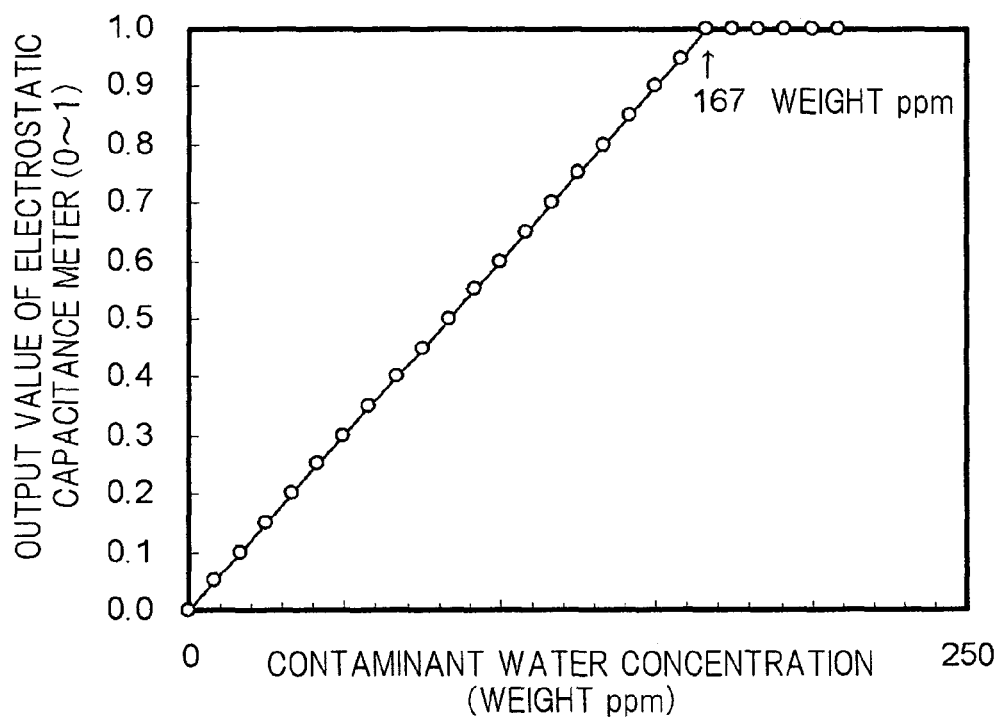
FIG. 16 is a chart showing the relation between the contaminant water concentration, measured with the use of the testing apparatus shown in FIGS. 15A and 15B, and the electrostatic capacitance.

In the first place, using the electrostatic capacitance meter 105 capable of measuring a value below the saturated water concentration, the saturated water concentration of the lubricant oil was measured. The lubricant oil was an additive free turbine oil of VG100 which was used in the previously described specific example of the rolling slide fatigue life test. As shown in a front elevational view in diagram (A) of FIG. 15, the lubricant oil was charged into a vessel 121 (resembling to, for example, the test oil bath 101 used in the testing device shown in and described with reference to FIG. 8) fitted with the electrostatic capacitance meter 105, a top lid provided with a silica gel receptacle was then placed and was allowed to stand for 1 hour while having been stirred by a magnetic stirrer 113, which is capable of adjusting the temperature, and heated to 110° C., a small amount of water mixed in the oil was thereafter allowed to evaporate and be absorbed by silica gel during that time. Thereafter, as shown in a longitudinal sectional view in diagram (B) of FIG. 15, it was maintained at 40° C. and pure water was then injected at a constant rate of 0.05 mL/h with the use of the syringe pump 104. In FIG. 16, a chart showing the chronological change of the electrostatic capacitance exhibited that time is shown. This electrostatic capacitance meter 105 outputs a value of 0 to 1 as a water activity. "0" indicates that the contaminant water concentration is zero and "1" indicates the contaminant water concentration is equal to or higher than the saturated water concentration.

Since as shown in FIG. 16 the measured value at 167 wt.ppm showed 1, the value thereof represents the saturated water concentration. If the relation between the contaminant water concentration and the rolling slide fatigue life is examined, there is the possibility that the saturated water concentration, which is unique to the lubricant oil, may provide one of indications of the anti-hydrogen brittleness.

Figure 17:
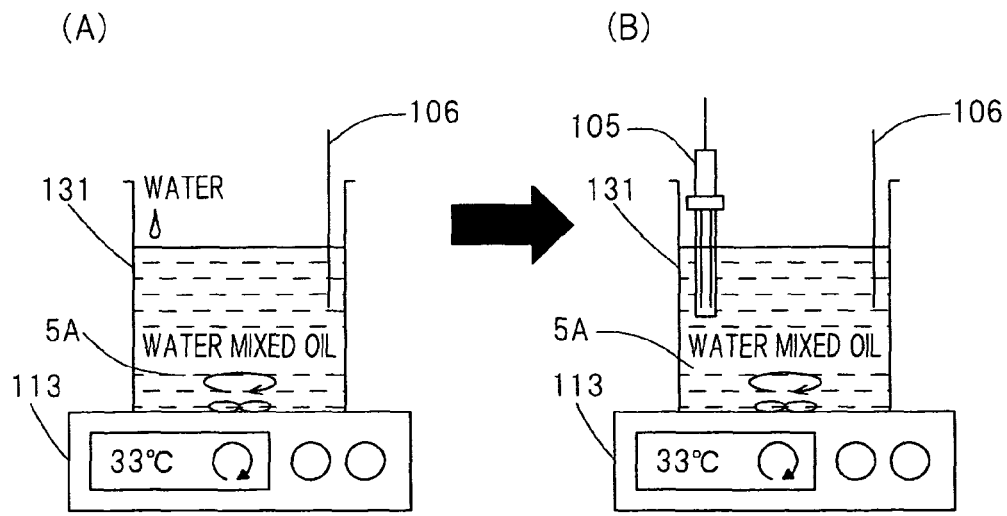
FIG. 17 shows a front elevational view (A) and a longitudinal sectional view (B) showing schematically a testing apparatus for measuring the electrostatic capacitance of the oil mixed with water.
Figure 18:
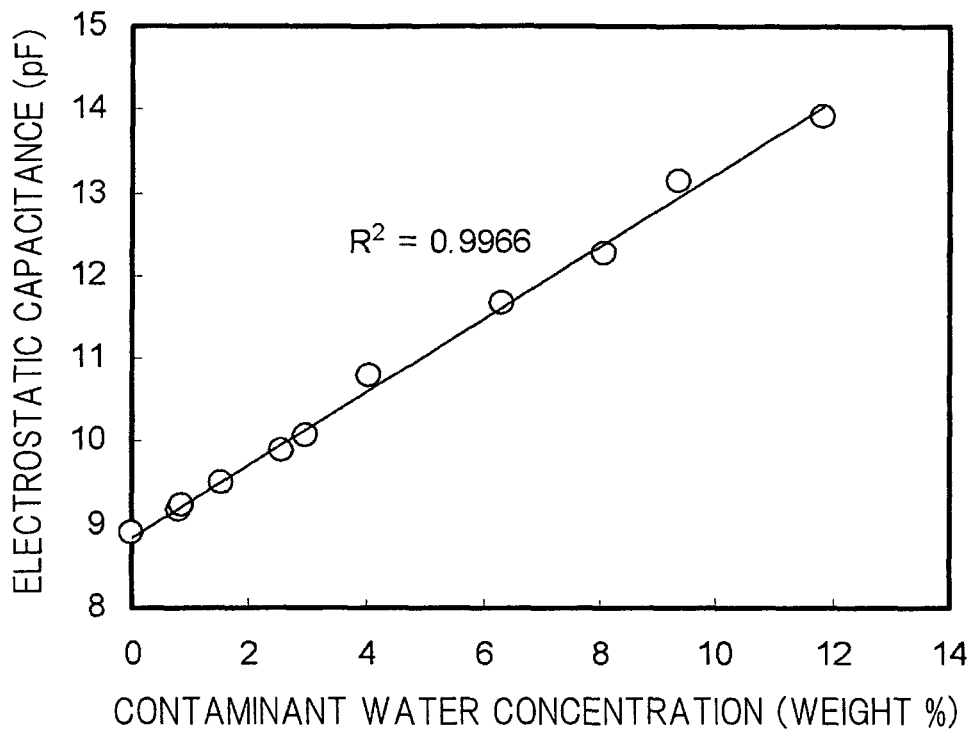
FIG. 18 is a chart showing the relationship between the contaminant water concentration and the electrostatic capacitance measured with the use of the testing apparatus shown in FIG. 17(A), (B)
Figure 19:
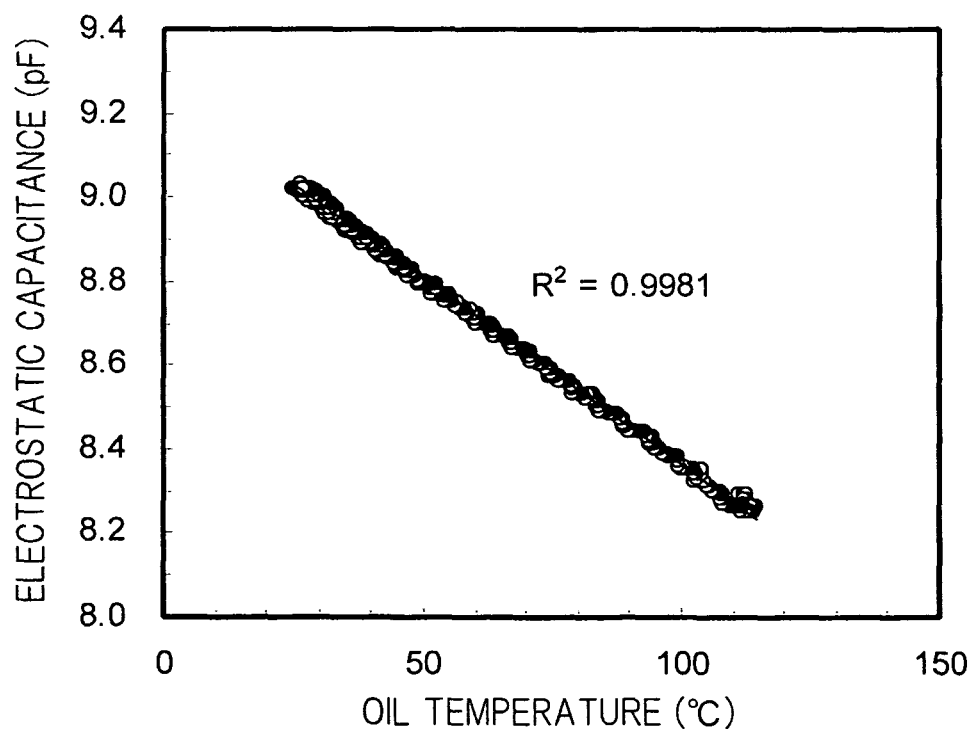
FIG. 19 is a chart showing the relationship between the oil temperature measured during the above test and the electrostatic capacitance.

In the next place, using the electrostatic capacitance meter 105 capable of measuring a value in excess of the saturated water concentration and even when water becomes clouded, the electrostatic capacitance was measured with variable water concentrations in the lubricant oil. The lubricant oil used was an additive free turbine oil of VG100 that was used in the specific example of the previously described rolling slide fatigue life test. As shown in a front elevational view in diagram (A) of FIG. 17, 70 to 80 mL of the lubricant oil 5A was charged into a beaker 131 (resembling to, for example, the test oil bath 101 used in the testing device shown in and described with reference to FIG. 8) having capacity of 100 mL, pure water was mixed and was stirred by a magnetic stirrer of a type capable of adjusting the temperature, until it was sufficiently mixed, while having been retained at a temperature of 33° C. Subsequently, as shown in a longitudinal sectional view in diagram (B) of FIG. 17, the electrostatic capacitance was measured by the electrostatic capacitance meter 105 fitted thereto. The result thereof is shown in the chart of FIG. 18. From this chart, it can readily be seen that a linear relation was obtained between the contaminant water concentration and the electrostatic capacitance that have a good linear relation. Also, with respect to the lubricant oil having no water mixed, the electrostatic capacitance was measured while the temperature was increased from about 25° C. (room temperature) to about 115° C. The result thereof is shown in the chart of FIG. 19. From this chart, it will readily be seen that a linear relation could be obtained between the contaminant water concentration and the electrostatic capacitance that have a good linear relation.

As can readily be understood from the respective charts shown in FIGS. 18 and 19, the electrostatic capacitance depends on the contaminant water concentration and the oil temperature. If within the range in which the contaminant water concentration and the temperature may vary, a plurality of such relations as shown in FIGS. 18 and 19 are determined and, with the contaminant water concentration taken as a response variable and the electrostatic capacitance as a dependent variable, a function of the oil temperature is prepared, the contaminant water concentration can be determined from the electrostatic capacitance and the oil temperature. It is, however, to be noted that in determining such an analytical curve as shown in FIGS. 18 and 19, it is desirable that not only a fresh oil, but a used oil having a different aspect of use be also measured.

As described above, according to the rolling slide fatigue life testing method, the rolling component part simulation product 3 including the object to be tested as a constituent component is immersed and operated in the lubricant oil 5A accumulated within the test oil bath 101, water is injected into the lubricant oil 5A and the electrostatic capacitance and the oil temperature in the lubricant oil 5A are measured by the electrostatic capacitance and the oil temperature, with the disturbance reduced as small as possible and while simulating the actual machine as faithfully as possible the premature damage originating from the hydrogen brittleness is efficiently caused to occur and antidote elements appropriate to conditions of use of the rolling component part simulation product 3 may be assessed.

Hereinafter, seventh to eighteenth embodiments of the present invention will be described in detail. It is to be noted that in the description that follows, components similar to those used in the practice of any one of the previously described embodiments of the present invention are shown by like reference numerals and, therefore, the details thereof are not reiterated for the sake of brevity. Where only a part of the construction is described, the remaining part of the construction is to be understood as similar to that in the preceding embodiment or embodiments. It is also to be noted that it is possible not only to combine components specifically described in connection with each of the foregoing and following embodiments of the present invention, but also to partially combine two or more of the foregoing and following embodiments of the present invention.

Figure 20:
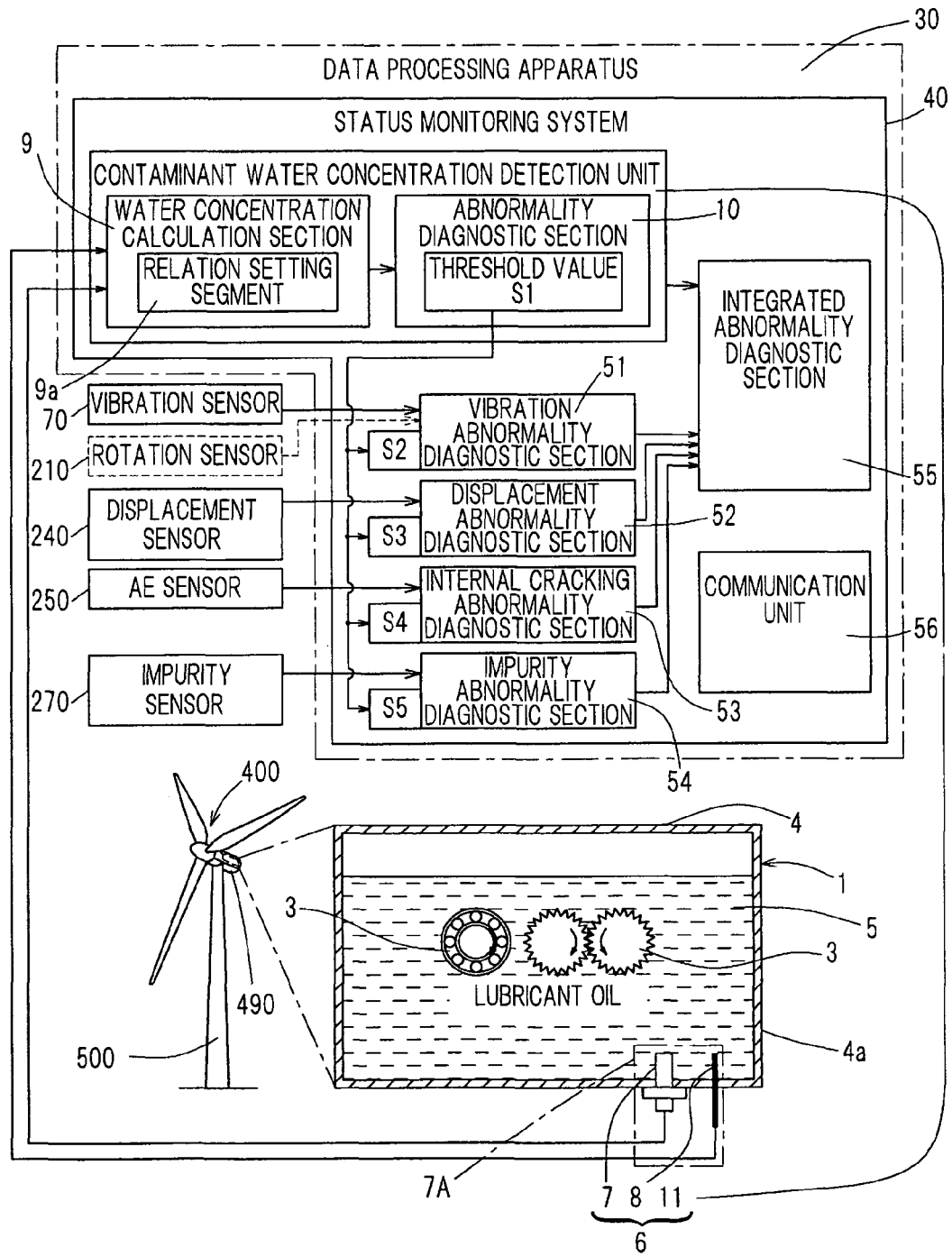
FIG. 20 is a block diagram showing a conceptual construction of the status monitoring system for the rolling device in accordance with a seventh embodiment of the present invention.

The case of application of a seventh embodiment of the present invention to a wind turbine generator will now be described with reference to FIGS. 20 and 21 by way of example. It is to be noted that any one of the previously described first to sixth embodiments is also applicable to the wind turbine generator. As shown in FIG. 20, a status monitoring system 40 used in this rolling device includes, in addition to the contaminant water concentration detection unit 11, which includes the water concentration calculation section 9, having the function of monitoring the contaminant water concentration in the lubricant oil used in the rolling device 1, and the abnormality diagnostic section 10 for the contaminant water concentration, a vibration abnormality diagnostic section 51, a displacement abnormality diagnostic section 52, an internal cracking abnormality diagnostic section 53, an impurity abnormality diagnostic section 54, an integrated abnormality diagnostic section 55 and a communication unit 56.

Figure 21:
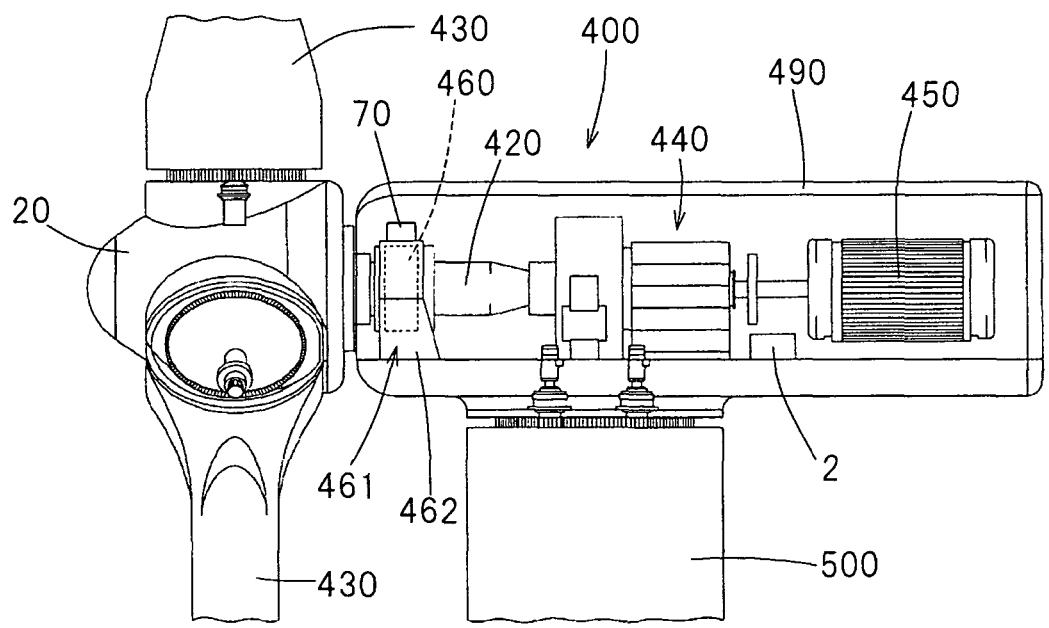
FIG. 21 is a side view, with a portion cut out, showing a wind turbine generator equipped with the rolling device that is an object to be monitored by the status monitoring system.

The rolling device 1 shown in FIG. 20 corresponds to a speed-increasing gear assembly 440 and a main shaft bearing device 461 both in a wind turbine generator 400 best shown in FIG. 21. It is to be noted that the internal structure of the speed-increasing gear assembly 440 employed in the wind turbine generator 400 is similar to that in the rolling device 1 shown in FIG. 7 that is referred to in describing the first embodiment and, therefore, the details thereof are not reiterated for the sake of brevity.

FIG. 21 illustrates a diagram schematically showing the structure of the wind turbine generator. The wind turbine generator 400 includes a main shaft 420, a blade 430, a speed-increasing gear assembly 540, an electric generator 550, a main shaft bearing device 461 having a main shaft bearing 460, and a data processing apparatus 2. The data processing apparatus 30 is comprised of a computer for performing a calculating process in the status monitoring system 40, employed in this wind turbine generator, and a program executed thereby. The speed-increasing gear assembly 440, the electric generator 450, the main shaft bearing 460 and the data processing apparatus 2 are all accommodated within a nacelle 490 which is in turn supported by a tower 500.

The main shaft 420 protrudes within the nacelle 490 and is in turn coupled with an input shaft of the speed-increasing gear assembly 440 and is rotatably supported by the main shaft bearing 460. The main shaft 420 transmits a rotational torque, generated by the blade 430 then receiving the wind, to the input shaft of the speed-increasing gear assembly 440. The blade 430 is provided at a tip end of the main shaft 420 and converts the wind force into the rotational torque which is transmitted to the main shaft 420.

The main shaft bearing 460 is fixedly installed within the nacelle 490 through a bearing housing 462 and rotatably supports the main shaft 420. The bearing housing 462, the main shaft bearing 460 and a lubricating mechanism (not shown) for lubricating the main shaft bearing 460 with oil cooperate with each other to form one of the rolling devices 1 shown in FIG. 20. The main shaft bearing 460 is comprised of a rolling bearing and is in the form of, for example, a self-aligning roller bearing, a tapered roller bearing, a cylindrical roller bearing or a ball bearing. It is to be noted that any of those bearings may be of a single row type or a double row type.

The speed-increasing gear assembly 440 is disposed between the main shaft 420 and the electric generator 450 and is configured to increase the rotational speed of the main shaft 420 and then output to the electric generator 450. The electric generator 450 is connected with an output shaft of the speed-increasing gear assembly 440 and, generates an electric power upon receipt of the rotational torque from the speed-increasing gear assembly 440. The electric generator 450 may be comprised of, for example, an induction generator. It is to be noted that even within this electric generator 450, bearings for rotatably supporting a rotor are provided.

It is to be noted that the rolling device 1 shown in FIG. 20 is a generic term given to a device for producing a rotational motion, which device is one of mechanisms forming the wind turbine generator 400 and is represented by, for example, the speed-increasing gear assembly 440. The rolling device 1 may be a device comprised of the main shaft bearing device 461 and a lubricating mechanism (not shown) therefor.

The contaminant water concentration detection unit 11 including the water concentration calculation section 9 and the abnormality diagnostic section 10 for the contaminant water concentration is provided in, for example, the data processing apparatus 30 which has been described with reference to FIG. 21.

As shown in FIG. 20, the vibration abnormality diagnostic section 51 makes use of an output of a vibration sensor 70, which is used to monitor vibrations occurring in any of the bearings forming the rolling device 1, to thereby determine the presence of an abnormality in such bearing. The bearing, vibrations of which is monitored by the vibration sensor 70, is, for example, the main shaft bearing 460 and is installed in, for example, the bearing housing. The vibration sensor 70 may be comprised of an acceleration sensor of a type utilizing a piezoelectric element. The abnormality diagnostic section 51 processes a detection signal of the vibration sensor 70, compare the result of such processing with a predetermined threshold value S2 and determines the presence of the abnormality in the event that it is higher than the threshold value S2. The abnormality diagnostic section 51 may be so designed as to acquire the rotational speed of a shaft, supported by the bearing referred to above or this bearing, from a rotation sensor 210 and the utilizes the detected rotational speed in a signal processing for the determination of the presence or absence of the abnormality.

The displacement abnormality diagnostic section 52 utilizes an output of a displacement sensor 240, which is a displacement gauge for detecting a relative displacement between the inner and outer rings, in the bearing referred to above and forming the rolling device 1, to thereby determine the presence or absence of an abnormality in the bearing. This displacement abnormality diagnostic section 52 compares the detected relative displacement or a value of this relative displacement which has been signal processed, with a predetermined threshold value S3 and then determines the presence of the abnormality in the event that it is higher than the threshold value S3.

The internal cracking abnormality diagnostic section 53 makes use of an output of an AE sensor 250 for detecting an acoustic emission wave in the above described bearing forming the rolling device 1 and then compares this output or a value of this output, which has been signal processed, with a predetermined threshold value S4 to thereby determine the presence of the abnormality in the event that it is higher than the threshold value S4.

The impurity abnormality diagnostic section 54 makes use of an output of a sensor 270 for detecting the amount of abrasion powder or other impurities contained in the lubricant oil used in the rolling device 1 and then compares this output or a value of this output which has been signal processed, with a predetermined threshold value S5 to thereby determine the presence of the abnormality in the event that it is higher than the threshold value S5.

It is to be noted that any of the vibration abnormality diagnostic section 51, the displacement abnormality diagnostic section 52, the internal cracking abnormality diagnostic section 53 and the impurity abnormality diagnostic section 54 may be so designed that, in the event that the contaminant water concentration detected by the water concentration calculation section 9 is higher than the threshold value S1, the corresponding threshold value S2 to S5, based on which the presence of the abnormality is determined in the associated abnormality diagnostic section 51 to 54, may be varied or a corresponding determining method may be altered.

The integrated abnormality diagnostic section 55 determines in a comprehensive manner in accordance with a predetermined rule the result of diagnosis given out by any of the abnormality diagnostic sections 10, 51, 52, 53 or 54. It is to be noted that a process of changing the threshold values S2 to S5, with which the respective abnormality diagnostic sections 51 to 54 determine the presence or absence of the abnormality, or a corresponding determining method, depending on the contaminant water concentration detected by the previously described water concentration calculation section 9, may be carried out by the integrated abnormality diagnostic section 55.

It is to be noted that while in describing the seventh embodiment shown in FIG. 20, no description has been made of the measurement chamber for accommodating therein the electrostatic capacitance detector 7 and the oil temperature measuring instrument 8, both used to monitor the contaminant water concentration, the measurement chamber 12 (shown in FIGS. 22, 23, 25 and 26) is preferably provided as shown in any of FIGS. 22 to 26 which will be referred to later.

In the wind turbine generator, any type of bearing is utilized within the main shaft bearing device 41 and the speed-increasing gear assembly 440 and is lubricated by an oil. The measurement chamber 12 is disposed either inside or outside of a tube or a tank, through which this lubricant oil is supplied, or the rolling device 1 as shown in any one of FIGS. 22, 23, 25 and 26 and the contaminant water concentration is measured therein.

Figure 27:
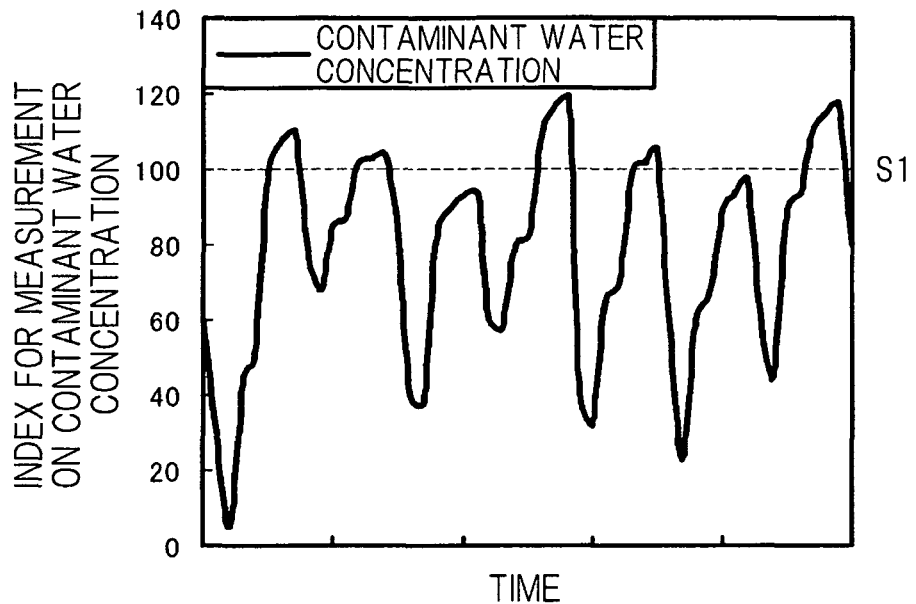
FIG. 27 is a chart showing water concentrations (predicted data) in a geographic area such as an ocean or a place susceptible to a fierce change in temperature.

The abnormality diagnosis of the contaminant water concentration during the monitoring is such that in the event that the contaminant water concentration during the monitoring is higher than the threshold value S1, which is shown later in FIGS. 27 and 28 and which represents a reference, a signal inviting a caution is outputted by the abnormality diagnostic section 10 shown in FIG. 20.

While the electrostatic capacitance detector 7 and the oil temperature measuring instrument 8 comprised of the thermocouple are used in measuring the contaminant water concentration, the use of the electrostatic capacitance oil temperature unit 7A, in which they are integrated together, makes it possible to reduce the number of works in the case sensors are individually installed. Also, a housing (not shown) for integrating two sensors (that is, the electrostatic capacitance meter 7 and the oil temperature measuring instrument 8 comprised of the thermocouple) plays a role of a covering for retaining each of those sensors and, in view of the fact that an effect of reducing breakages can be expected, it is considered that the reliability of the sensor itself can be increased.

It may be considered that on the ocean or in a region where a change of climatic temperature is large, the contaminant water concentration is high and bearing damage resulting from the hydrogen brittleness occurs frequently. Where this device is used in such a region, as shown in FIG. 27, it is suspected that the water concentration may exceed the threshold value S1 in a short period of time. It is to be noted that in the event of the excess over the threshold value S1, it can be possible to avoid the damage resulting from the hydrogen brittleness by taking a countermeasure such as, for example, replacing with a seal having an excellent occlusive property and/or activating a heating equipment such as, for example, a heater for preventing dew condensation.

Figure 28:
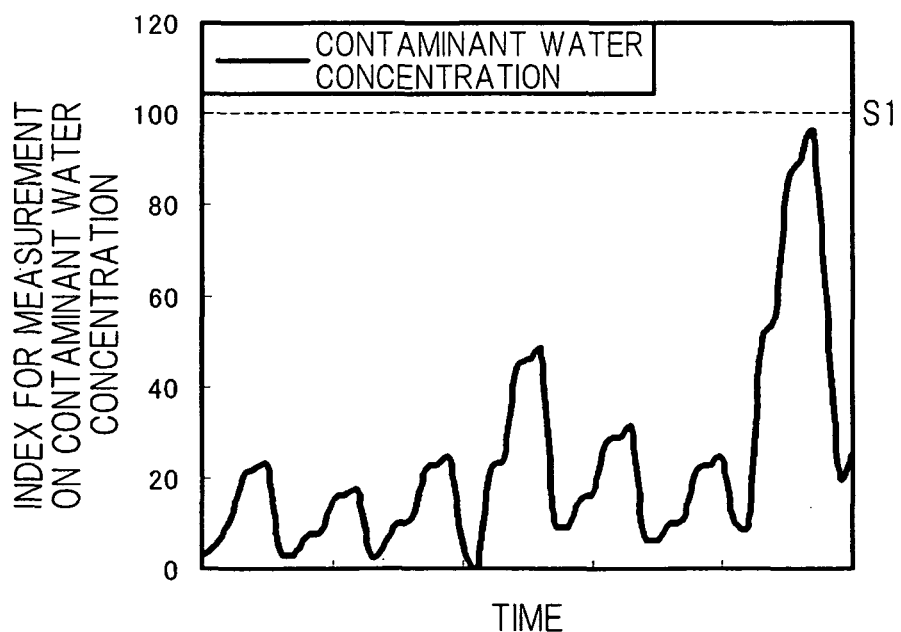
FIG. 28 is a chart showing water concentration (predicted data) in a geographic area such as a land or a plate less susceptible to a change in temperature.

Also, where this device is used on the land or in a region where the change in climatic temperature is small, it may be suspected that as shown in FIG. 28, even through the water concentration changes day by day, the threshold value S1 will barely be exceeded. With respect to the timing at which exfoliation resulting from the hydrogen brittleness, it is predicated by the operating hours or the accumulation of the amount of rotation, during which the threshold value S1 is exceeded.

It is to be noted that regarding the measurement of the contaminant water concentration, in order to perform the monitoring on a safe side, it is preferred to measure a high contaminant water concentration by providing a measurement chamber at a position lower than the tank or the oil bath and facilitating capture of water and additives to a position proximate to the sensor by the utilization of the difference in specific gravity.

Combination with other sensors will now be described. It is possible to estimate whether or not the actual life of the target bearing assembly comes to the end of the designed expected life under the influence of the hydrogen brittleness. However, it is difficult to ascertain the exfoliation that takes place actually and also to detect damages of the bearing assembly resulting from any other reasons. Accordingly, if combined with any of the following various sensors, it is possible to simultaneously monitor the damage of the bearing assembly other than the exfoliation resulting from the hydrogen brittleness. By way of example, when a vibration sensor 70 such as, for example, a vibration acceleration sensor is used concurrently, it becomes possible to detect vibrations caused by any abnormality including the exfoliation resulting from the hydrogen brittleness.

Also, where the AE sensor 250 is used concurrently in place of, or used simultaneously with, the vibration acceleration sensor, not only the exfoliation in the surface, but cracking resulting from the hydrogen brittleness, which occurs inside the metal, can be measured. At this time, the determination of the occurrence of the cracking by means of the AE sensor 250 may be difficult because of causeless AE waves found here and there, but where the AE waves are generated while the contaminant water concentration is high, it may be expected that the internal cracking is taking place with a high probability, and, therefore, it becomes possible to estimate the abnormality at an earlier stage.

Also, in the event of the occurrence of an abrasion inside the bearing assembly as a result of a metal contact of various causalities, it is difficult to detect merely with the measurement of the water concentration. In view of this, by collecting the relative displacement of the inner ring relative to the outer ring of the bearing assembly with the use of the displacement sensor 240, it is possible to detect the abrasion and the integrated status monitoring can be enabled.

In addition, since the deterioration of the lubricant oil as a result of oxidization of the lubricant oil and/or admixture of dusts caused by the long hour operation is expected, the concurrent use of an impurity sensor 270 such as, for example, a deterioration sensor or the like of the oil makes it possible to predicate the occurrence of a lubrication defect that leads to breakdown of the bearing assembly. Simultaneously by considering the contaminant water concentration and applying a correction to the impurity sensor 270 such as, for example, an oil deterioration sensor or the like, predication of the premature damage of the bearing assembly resulting from the lubricant oil can become further accurate.

In view of the foregoing, the probability of occurrence, or the timing of occurrence, of the exfoliation in the bearing assembly as a result of the hydrogen brittleness can be estimated. Thanks to it, in the wind turbine generator, it becomes possible to reduce the length of time of halt in operation subsequent to the occurrence of the abnormality.

FIGS. 22 to 26 illustrate modified forms of the contaminant water concentration monitoring device 6. In the status monitoring system of the wind turbine generator in the seventh embodiments shown in and described with reference to FIGS. 20 and 21, the contaminant water concentration monitoring device 6 shown in any one of FIGS. 22 to 26 may be employed. It is to be noted that in those FIGS. 22 to 26, other structural features than those of the status monitoring system of the wind turbine generator are not shown.

Figure 22:
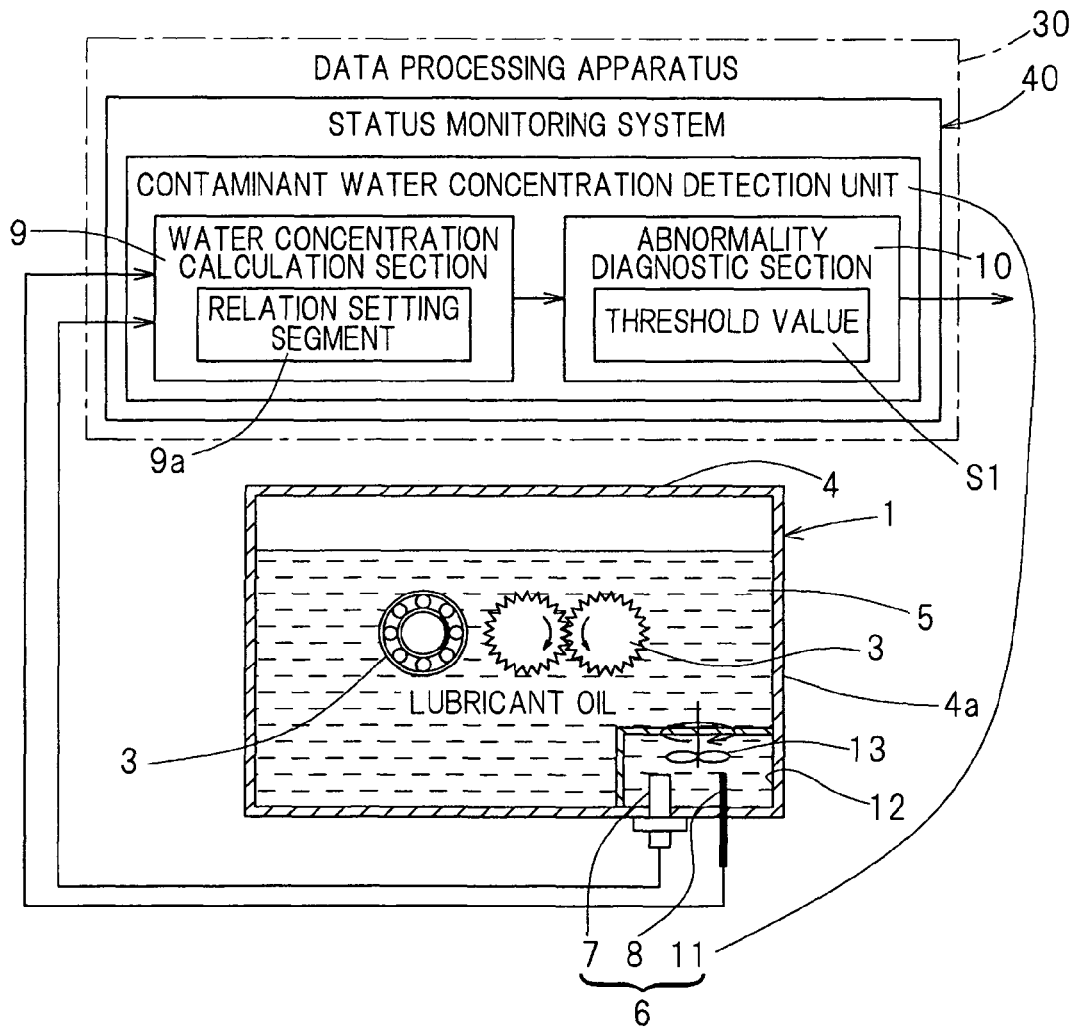
FIG. 22 is a block diagram, with a portion cut out, showing a conceptual construction of the status monitoring system for the rolling device in accordance with an eighth embodiment of the present invention.

In the seventh embodiment shown in and described with reference to FIG. 20, arrangement has been made to measure the electrostatic capacitance and the oil temperature of the lubricant oil 5 within the lubricant oil reservoir 4a in the housing 4, but in an eighth embodiment shown in and described with reference to FIG. 22, the structure of the rolling device 1 except for the data processing apparatus 30 is rendered to be similar to the previously described second embodiment shown in FIG. 2. Other functions and effects are also similar to those afforded by the second embodiment and the details thereof are not reiterated for the sake of brevity. It is to be noted that other structural features and effects afforded by the eighth embodiment shown in FIG. 22 are similar to those afforded by the seventh embodiment shown in and described with reference to FIG. 20.

Figure 23:
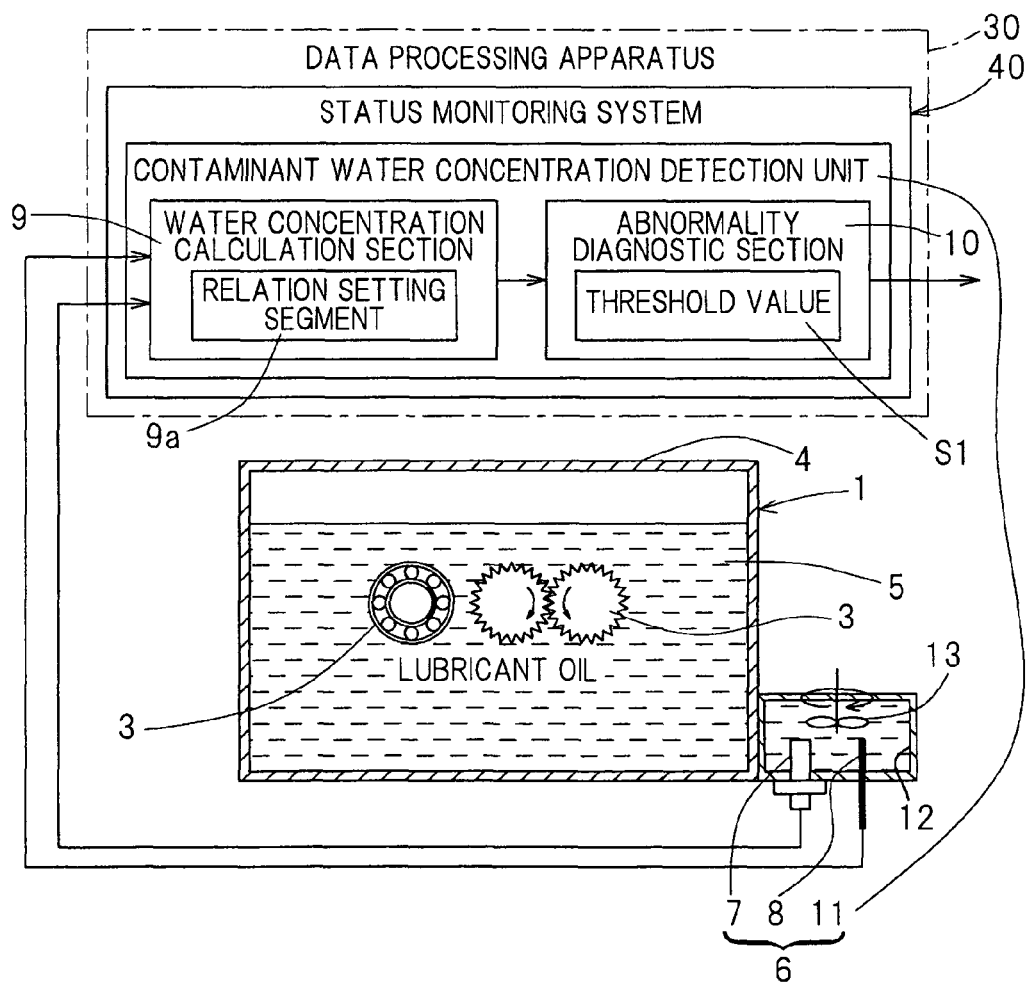
FIG. 23 is a block diagram, with a portion cut out, showing a conceptual construction of the status monitoring system for the rolling device in accordance with a ninth embodiment of the present invention.

In a ninth embodiment shown in FIG. 23, the structure of the rolling device 1 except for the data processing apparatus 30 is rendered to be similar to the previously described third embodiment shown in FIG. 3. Since other functions and effects are also similar to those afforded by the third embodiment, the details thereof are not reiterated for the sake of brevity. It is to be noted that other structural features and effects afforded by the ninth embodiment shown in FIG. 23 are similar to those afforded by the seventh embodiment shown in and described with reference to FIG. 20.

Figure 24:
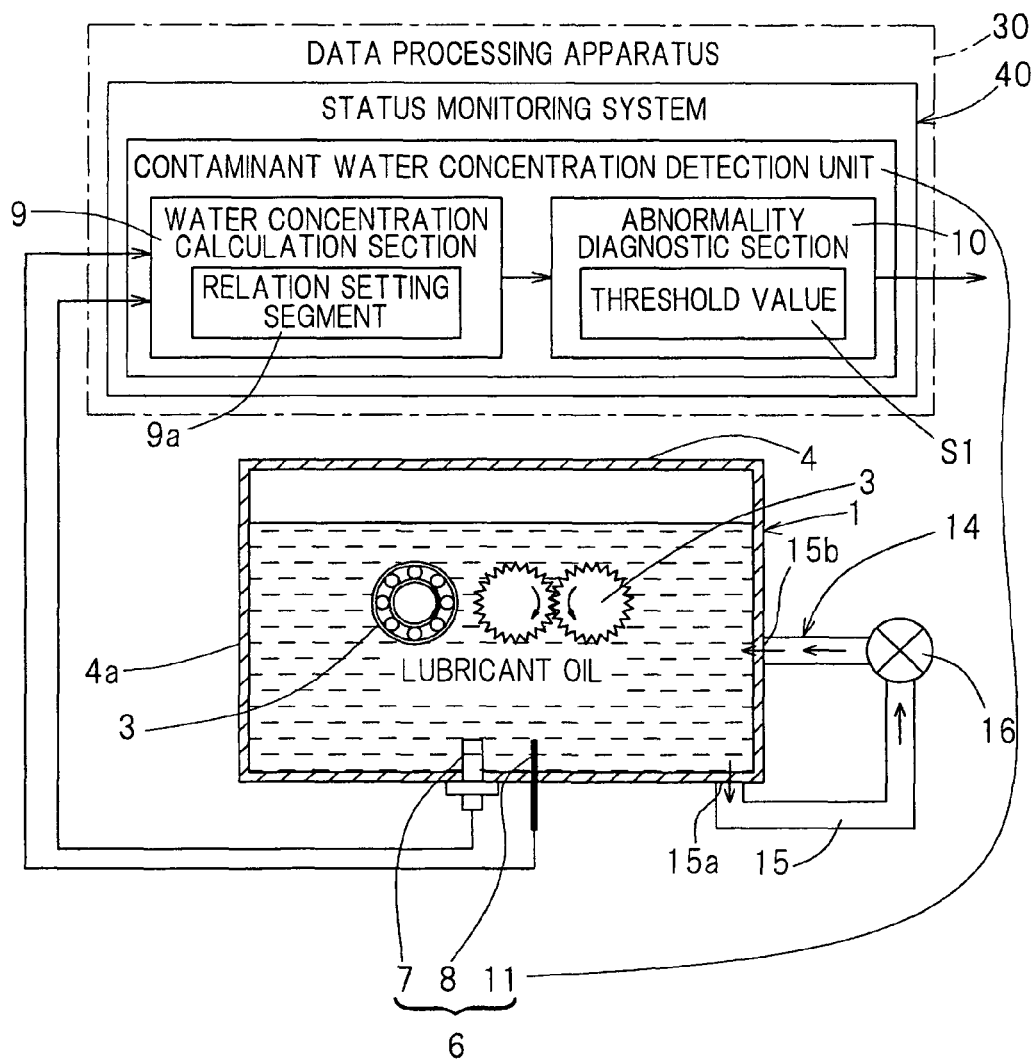
FIG. 24 is a block diagram, with a portion cut out, showing a conceptual construction of the status monitoring system for the rolling device in accordance with a tenth embodiment of the present invention.

In a tenth embodiment shown in FIG. 24, the structure of the rolling device 1 except for the data processing apparatus 30 is rendered to be similar to the previously described fourth embodiment shown in FIG. 4. Other functions and effects are also similar to those afforded by the fourth embodiment and, therefore, the details thereof are not reiterated for the sake of brevity. It is to be noted that other structural features and effects are similar to those afforded by the seventh embodiment shown in and described with reference to FIG. 20.

Figure 25:
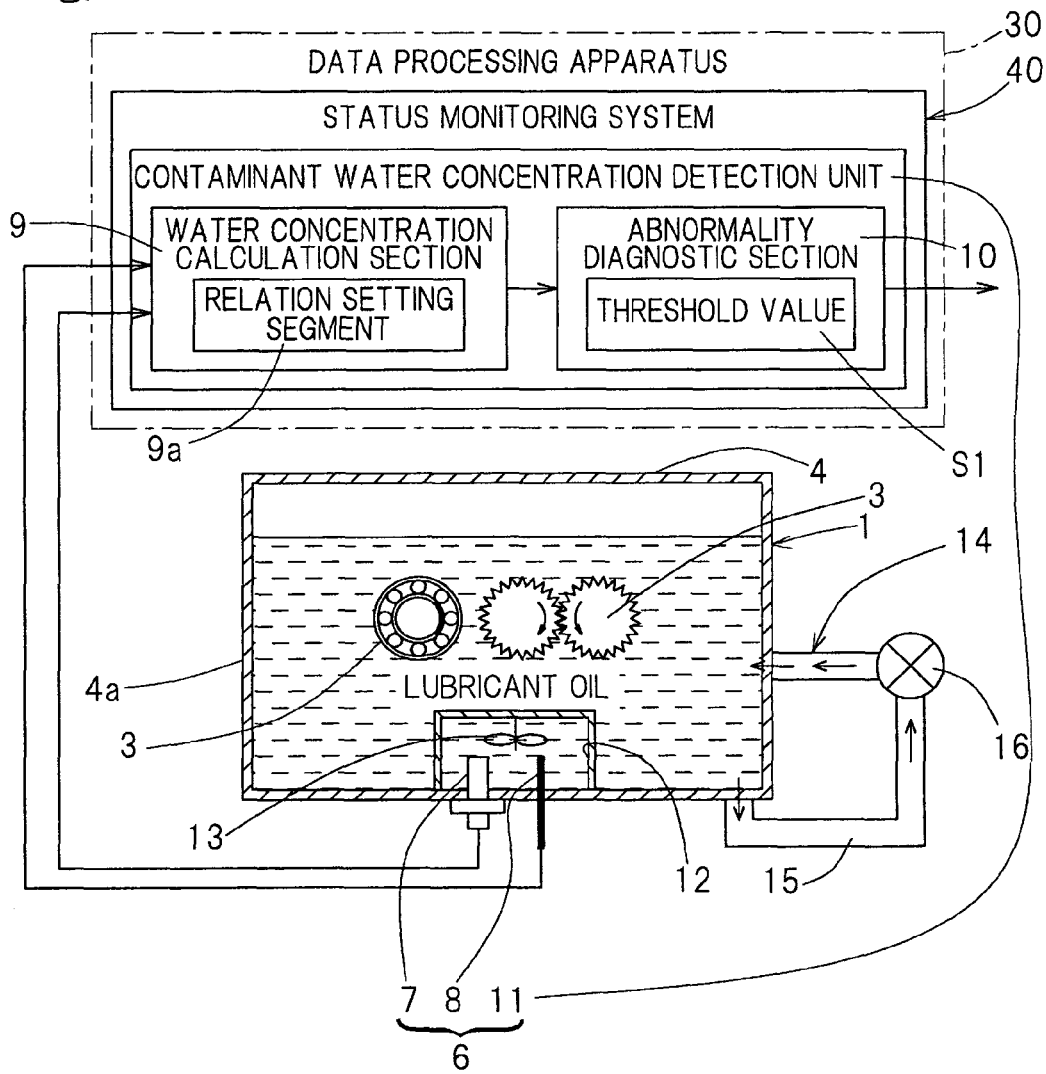
FIG. 25 is a block diagram, with a portion cut out, showing a conceptual construction of the status monitoring system for the rolling device in accordance with an eleventh embodiment of the present invention.

In an eleventh embodiment shown in FIG. 25, the structure of the rolling device 1 except for the data processing apparatus 30 is rendered to be similar to the previously described fifth embodiment shown in FIG. 5. Other functions and effects are also similar to those afforded by the fifth embodiment and, therefore, the details thereof are not reiterated for the sake of brevity. Other structural features and effects are similar to those afforded by the tenth embodiment shown in to FIG. 24.

Figure 26:
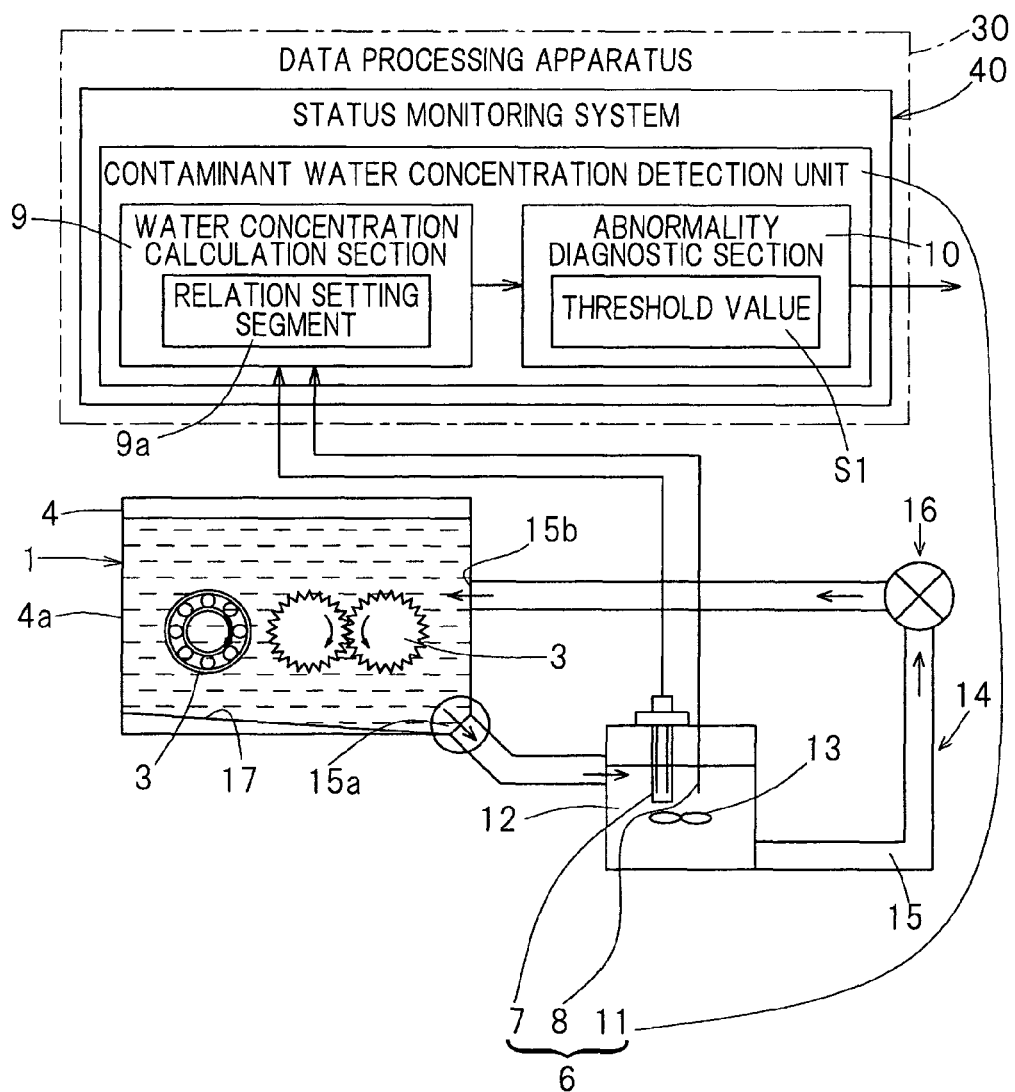
FIG. 26 is a block diagram, with a portion cut out, showing a conceptual construction of the status monitoring system for the rolling device in accordance with a twelfth embodiment of the present invention.

In a twelfth embodiment shown in FIG. 26, the structure of the rolling device 1 except for the data processing apparatus 30 is rendered to be similar to the previously described sixth embodiment shown in FIG. 6. Other functions and effects are also similar to those afforded by the sixth embodiment and, therefore, the details thereof are not reiterated for the sake of brevity. In this embodiment, unless otherwise specifically referred to, it is similar to the previously described seventh embodiment shown in FIG. 20.

In the description that follows, specific examples of the vibration abnormality diagnostic section 51 shown in FIG. 20 will be described in detail with particular reference to FIGS. 29 to 40.

Specific Example 1

Figure 29:
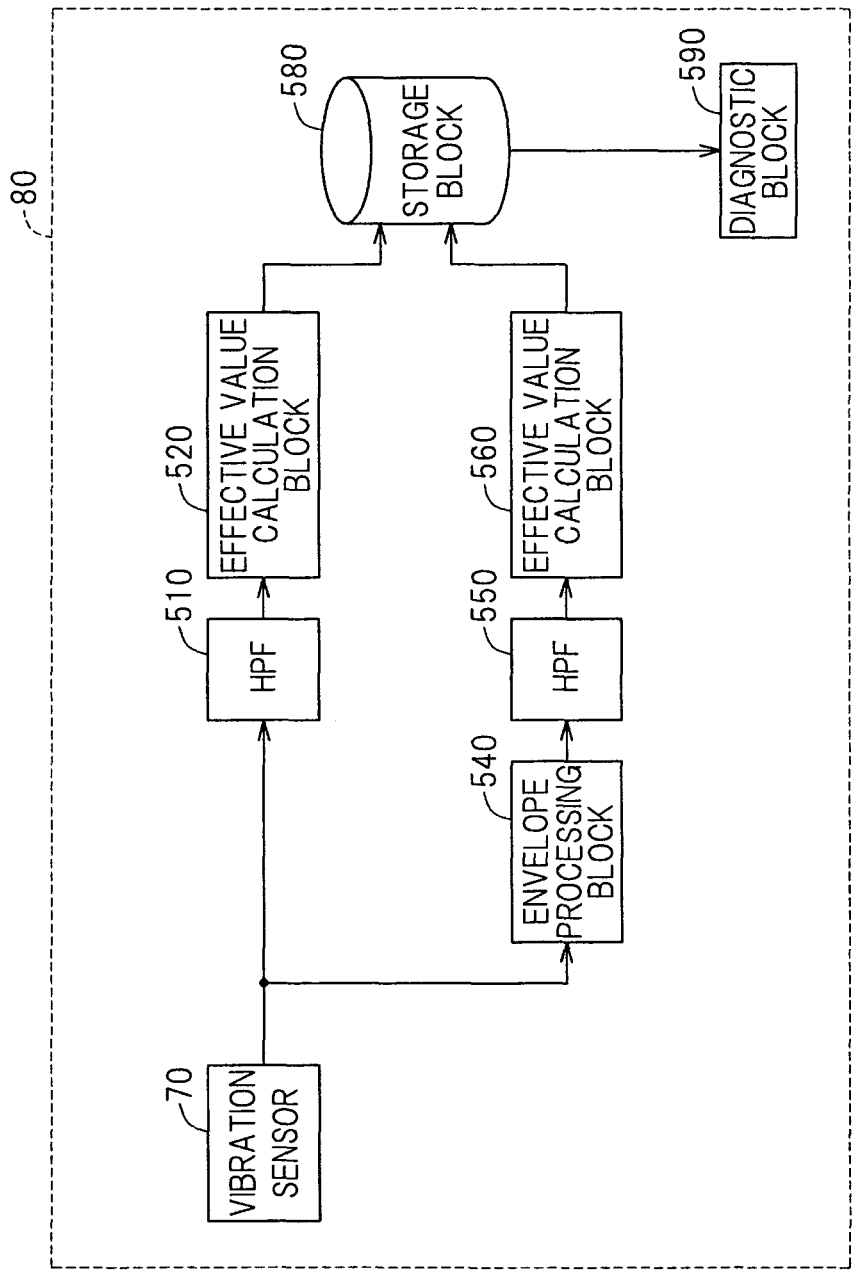
FIG. 29 is a block diagram showing a conceptual construction of a first specific example 1 of an abnormality diagnostic section for vibration abnormality which utilizes the status monitoring system in accordance with the seventh embodiment.

Referring to FIG. 29, the vibration sensor 70 is installed in a bearing forming the rolling device 1 shown in FIG. 20, for example, the main shaft bearing 460. This vibration sensor 70 detects a vibration of the bearing assembly and outputs its detection value to the vibration abnormality diagnostic section 51 in the data processing apparatus 2. The vibration sensor 70 includes an acceleration sensor or the like of a type utilizing a piezoelectric element as hereinbefore described. The vibration abnormality diagnostic section 51 includes high pass filters (HPF) 510, 550, effective value calculation blocks 520, 560, an envelope processing block 540, a storage block 580 and a diagnostic block 590. The effective value calculation block 520 is a first calculation block referred to in the claims and the effective value calculation block 560 is a second calculation block referred to in the claims.

The HPF 510 receives from the vibration sensor 70 the detection value indicative of the vibration occurring in the bearing assembly. And, this HPF 510 allows a signal component, which is higher than a predetermined frequency, to pass therethrough and cuts off a low frequency component. This HPF 510 is provided for removing a direct current component contained in a vibration waveform of the bearing. It is to be noted that if the vibration sensor 70 is of a type containing no direct current component in its output, the use of the HPF 510 may be dispensed with.

The effective value calculation block 520 receives from the HPF 510 the vibration waveform of the bearing from which the direct current component has been removed. And, the effective value calculation block 520 calculates an effective value (which is also referred to as a root means square (RMS) value) of the vibration waveform of the bearing and then outputs the calculated effective value of the vibration waveform to the storage block 580.

The envelope processing block 540 receives the detection value descriptive of the vibration occurring in the bearing. And, the envelope processing block 540 performs an enveloping process on the detection signal received thereby to generate an envelope waveform of the vibration waveform of the bearing. It is to be noted that the enveloping process calculated in the envelope processing block 540 may be of any known technique and, as one example thereof, the vibration waveform of the bearing measured by the use of the vibration sensor 70 is rectified to an absolute value and is then passed through a low pass filter (LPF) to generate the envelope waveform of the vibration waveform of the bearing 6.

The high pass filter 550 receives from the envelope processing block 540 the envelope waveform of the vibration waveform of the bearing. And, the high pass filter 550 allows, with respect to the envelope waveform received thereby, a signal component that is higher than a predetermined frequency and cuts off a low frequency component. The high pass filter 550 is provided for removing a direct current component contained in the envelope waveform and extracting an alternating current component of the envelope waveform.

The effective value calculation block 560 receives from the high pass filter 560 the envelope waveform from which the direct current component has been removed, that is the alternating current component of the envelope waveform. And, the effective value calculation block 560 calculates an effective value (RMS value) of the alternating current component of the envelope waveform received thereby and outputs the calculated effective value of the alternating current component of the envelope waveform to the storage block 580.

The storage block 580 stores the effective value of the vibration waveform of the bearing, which has been calculated by the effective value calculation block 520, and the effective value of the alternating current component of the envelope waveform, which has been calculated by the effective value calculation block 560, in synchronized fashion and from moment to moment. This storage block 580 is comprised of, for example, a readable and writable, nonvolatile memory or the like.

The diagnostic block 590 reads the effective value of the vibration waveform of the bearing and the effective value of the alternating current component of the envelope waveform, both stored in the storage block 580 from moment to moment, from the storage block 580 and diagnoses the abnormality of the bearing on the basis of two effective values readout therefrom. The threshold value S2 referred to previously is used in this abnormality diagnosis. More specifically, the diagnostic block 590 diagnoses the presence or absence of the abnormality in the bearing assembly on the basis of a chronological changeion of both of the effective value of the waveform of the bearing and the effective value of the alternating current component of the envelope waveform.

In other words, since the effective value of the vibration waveform of the bearing calculated by the effective value calculation block 520 is an actual value of a raw waveform which has not yet subjected to the enveloping process, the increase of the value is small in the case of an impulse-like vibration in which a signal increased only when the rolling elements move past the site of exfoliation that has occurred in, for example, a portion of the raceway ring, but the increase of the value is considerable in the case of the persistent vibration that is generated in the event of the occurrence of a surface roughening resulting from a contact between the raceway ring and the rolling element or an insufficient lubrication or the like.

On the other hand, the effective value of the alternating current component of the envelope waveform calculated by the effective value calculation block 560 is such that the increase of the value is small or no increase occurs in the case of the persistent vibration generated in the event of the surface roughening of the raceway ring and the insufficient lubrication, the increase of the value becomes large in the case of the impulse-like vibration. In view of the above, in this Specific Example 1, by the utilization of the effective value of the vibration waveform of the bearing and the effective value of the alternating current component of the envelope waveform, detection of the abnormality, which cannot be detected with one of those effective values, is enabled and a further accurate abnormality diagnosis is made realizable.

FIGS. 30 to 33 illustrate respective waveform charts showing the vibrations of the bearing measured with the use of the vibration sensor 70. It is to be noted in FIGS. 30 to 33, the vibration waveforms exhibited in the case that the rotational speed of the main shaft 420 (best shown in FIG. 21) is held at a constant value.

Figure 30:
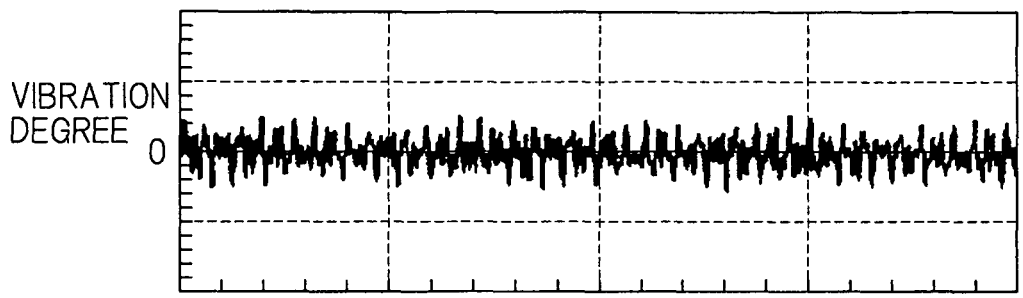
FIG. 30 is a chart illustrating waveforms of vibrations occurring in a bearing when no abnormality occurs in such bearing.
Figure 32:
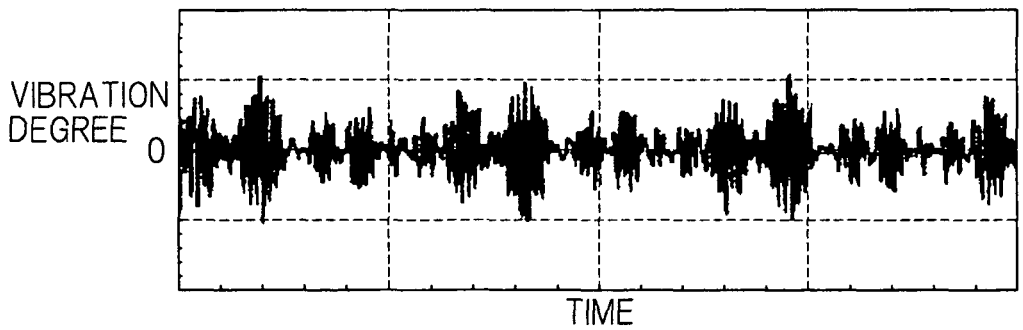
FIG. 32 is a chart illustrating waveforms of vibrations occurring in the bearing, which are observed when exfoliation occurs in the raceway ring of the bearing at an initial stage.

FIG. 30 illustrates a waveform chart showing the vibration waveform of the bearing exhibited when no abnormality occurs in the bearing. In FIG. 32, the axis of abscissas represents time and the axis of ordinates represents the degree of vibration, which represents the magnitude of the vibration.

Figure 31:
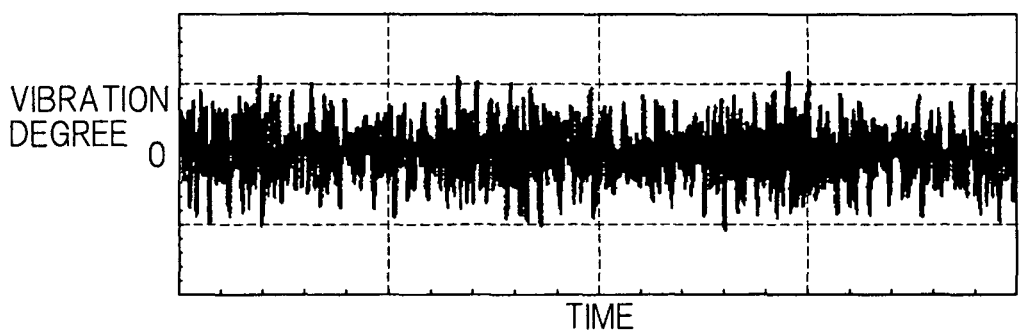
FIG. 31 is a chart illustrating waveforms of vibrations occurring in a bearing when a surface roughening or an insufficient lubrication occurs in a raceway ring of the bearing.

FIG. 31 is a waveform chart showing the vibration waveform of the bearing observed when the surface roughing of the raceway ring of the bearing and/or the insufficient lubrication occur. As shown in FIG. 31, once the surface or the insufficient lubrication occurs in the raceway ring of the bearing assembly, the degree of vibration increases and a condition in which the degree of vibration increases occurs persistently. No prominent peak appears in the vibration waveform. Accordingly, when with respect to such vibration waveform, the effective value (output of the effective value calculation block 520 shown in FIG. 29) of the vibration waveform, when no abnormality occur in the bearing, and the effective value (output of the effective value calculation block 560 shown in FIG. 29) of the alternating current component of the envelope waveform are compared, the effective value of the raw vibration waveform, which is not subjected to the enveloping process, increases, and the effective value of the alternating current component of the envelope waveform does not increase so much.

Figure 34:
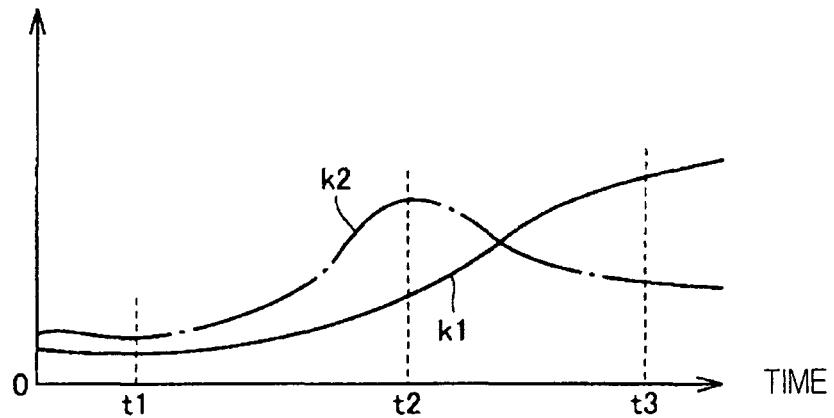
FIG. 34 is a chart showing a root mean square value of a vibratory waveform of the bearing, when the exfoliation takes place in a portion of the raceway ring of the bearing and is subsequently transferred into the entire region thereof, and a chronological change of the effective value of an alternating current component of an envelope waveform.

FIG. 32 illustrates a waveform chart showing the vibration waveform of the bearing at the initial stage at which the exfoliation occurs in the raceway ring of the bearing. As shown in FIG. 34, the initial stage of the exfoliation abnormality is represented by a condition in which the exfoliation occurs in a portion of the raceway ring and, since a considerable vibration is generated as the rolling element moves past the site of exfoliation, pulse-like vibrations occur cyclically according to the rotation of a shaft. When the rolling elements move past any other site than the site of exfoliation, the increase of the degree of vibration is small. Accordingly, when with respect to such vibration waveform the effective value of the vibration waveform, when no abnormality occur in the bearing, and the effective value of the alternating current component of the envelope waveform are compared, the effective value of the alternating current component of the envelope waveform increases and the effective value of the raw vibration waveform does not increase so much.

Figure 33:
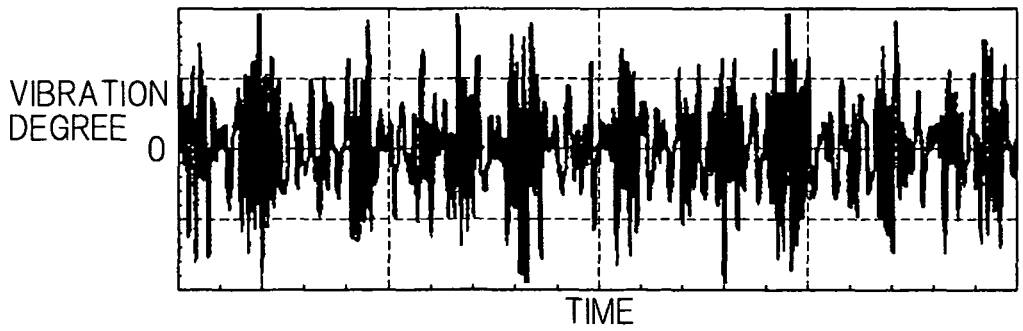
FIG. 33 is a chart illustrating waveforms of vibrations occurring in the bearing, which are observed at a final stage of the exfoliation abnormality.

FIG. 33 illustrates a waveform chart showing the vibration waveform of the bearing observed at the terminal stage of the exfoliation abnormality. As shown in FIG. 33. The terminal stage of the exfoliation abnormality is represented by a condition in which the exfoliation is transited over the entire area of the raceway ring and, as compared with the initial stage of abnormality, the degree of vibration increases wholly and the tendency of the pulse-like vibration is weakened. Accordingly, when with respect to such vibration waveform the effective value of the vibration waveform at the initial stage of the exfoliation abnormality and the effective value of the alternating current component of the envelope waveform are compared, the effective value of the raw vibration waveform increase and the effective value of the alternating current component of the envelope waveform is lowered.

FIG. 34 illustrates a chart showing respective chronological changes of the effective value of the vibration waveform of the bearing and the effective value of the alternating current component of the envelope waveform, when the exfoliation occurred in a portion of the raceway ring of the bearing and subsequently transited over the entire area of the raceway ring. It is to be noted that in FIG. 34 and also in FIG. 35 reference to which will be made later, the chronological change of each of those effective values exhibited when the rotational speed of the main shaft 420 is at a constant value.

Referring now to FIG. 34, a curve k1 represents the chronological change of the effective value of the vibration waveform exhibited when no envelope process is applied while a curve k2 represents the chronological change of the effective value of the alternating current component of the envelope waveform. At the timing t1 before the occurrence of the exfoliation, i.e., at which the exfoliation has not yet occurred, both of the effective value (k1)) of the vibration waveform and the effective value (k2) of the alternating current component of the envelope waveform are small. It is to be noted that the vibration waveform at the timing t1 represents such a waveform as shown in FIG. 32, reference to which has already been made above.

Once the exfoliation occurs in a portion of the raceway ring of the bearing, as discussed with reference to FIG. 32, the effective value (k2) of the alternating current component of the envelope waveform increases considerably and, on the other hand, the effective value (k1) of the vibration waveform with no envelope process being applied does not increase so much (in the vicinity of the timing t2).

Also, when the exfoliation is subsequently transited to the entire area of the raceway ring, the effective value (k1) of the vibration waveform with no envelope process being applied increases considerably and, on the other hand, the effective value (k2) of the alternating current component of the envelope waveform is lowered (in the vicinity of the timing t3) as discussed with reference to FIG. 33.

Figure 35:
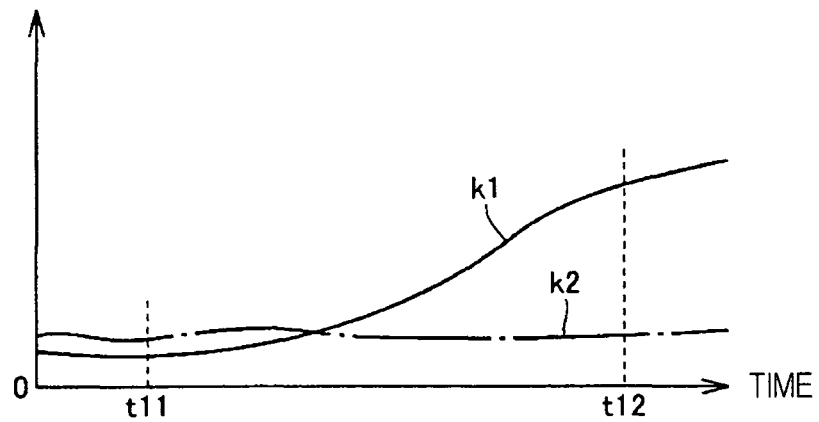
FIG. 35 is a chart showing the effective value of the vibratory waveform, which is exhibited when a surface roughening and/or an insufficient lubrication occur in the raceway ring of the bearing, and the chronological change of the root mean square value of the alternating current component of the envelope waveform.

In addition, FIG. 35 illustrates a chart showing the chronological change of the effective value of the vibration waveform of the bearing and the effective value of the alternating current component of the envelope waveform when the surface roughening of the insufficient lubrication occurs in the raceway ring of the bearing. Even in FIG. 35, as is the case with FIG. 34, a curve k1 represents the chronological change of the effective value of the vibration waveform exhibited when no envelope process is applied while a curve k2 represents the chronological change of the effective value of the alternating current component of the envelope waveform.

At the timing t11 before the occurrence of the surface roughening and/or the insufficient lubrication of the raceway ring, both of the effective value (k1) of the vibration waveform and the effective value (k2) of the alternating current component of the envelope waveform are small. It is to be noted that the vibration waveform at the timing t11 becomes that similar to the waveform shown in FIG. 30.

Once the surface roughening or the insufficient lubrication of the raceway ring of the bearing assembly occurs, the effective value (k1) of the waveform, to which no envelope process is applied, increases and, on the other hand, the increase of the effective value (k2) of the alternating current component of the envelope waveform is not observed (in the vicinity of the timing t12).

As discussed above, based on the chronological change of each of the effective value (k1) of the raw vibration waveform, in which no envelope process is applied, and the effective value (k2) of the alternating current component of the envelope waveform, the abnormality diagnosis of the bearing assembly can be further accurately performed.

Thus, according to the Specific Example 1 above, since the occurrence of an abnormality in the bearing is diagnosed on the basis of the effective value of the vibration waveform of the bearing, which has been measured by the use of the vibration sensor 70, and the effective value of the alternating current component of the envelope waveform, which is generated by applying the envelope process to the vibration waveform measured by the use of the vibration sensor 70, the accurate abnormality diagnosis as compared with the conventional technique relying on the frequency analysis can be realized. Also, the unnecessary maintenance can be reduced and the cost incurred in the maintenance can be reduced.

Specific Example 2

When the rotational speed of the main shaft 420 shown in FIG. 21 changes, the magnitude of vibration of the bearing such as, for example, the main shaft bearing 460 changes. Generally, the degree of vibration of the bearing increase with an increase of the rotational speed of the main shaft. Accordingly, in the Specific Example 2, the effective value of the vibration waveform of the bearing and the effective value of the alternating current component of the envelope waveform are normalized with the rotational speed and the abnormality diagnosis of the bearing assembly is performed with the use of the effective values so normalized.

Figure 36:
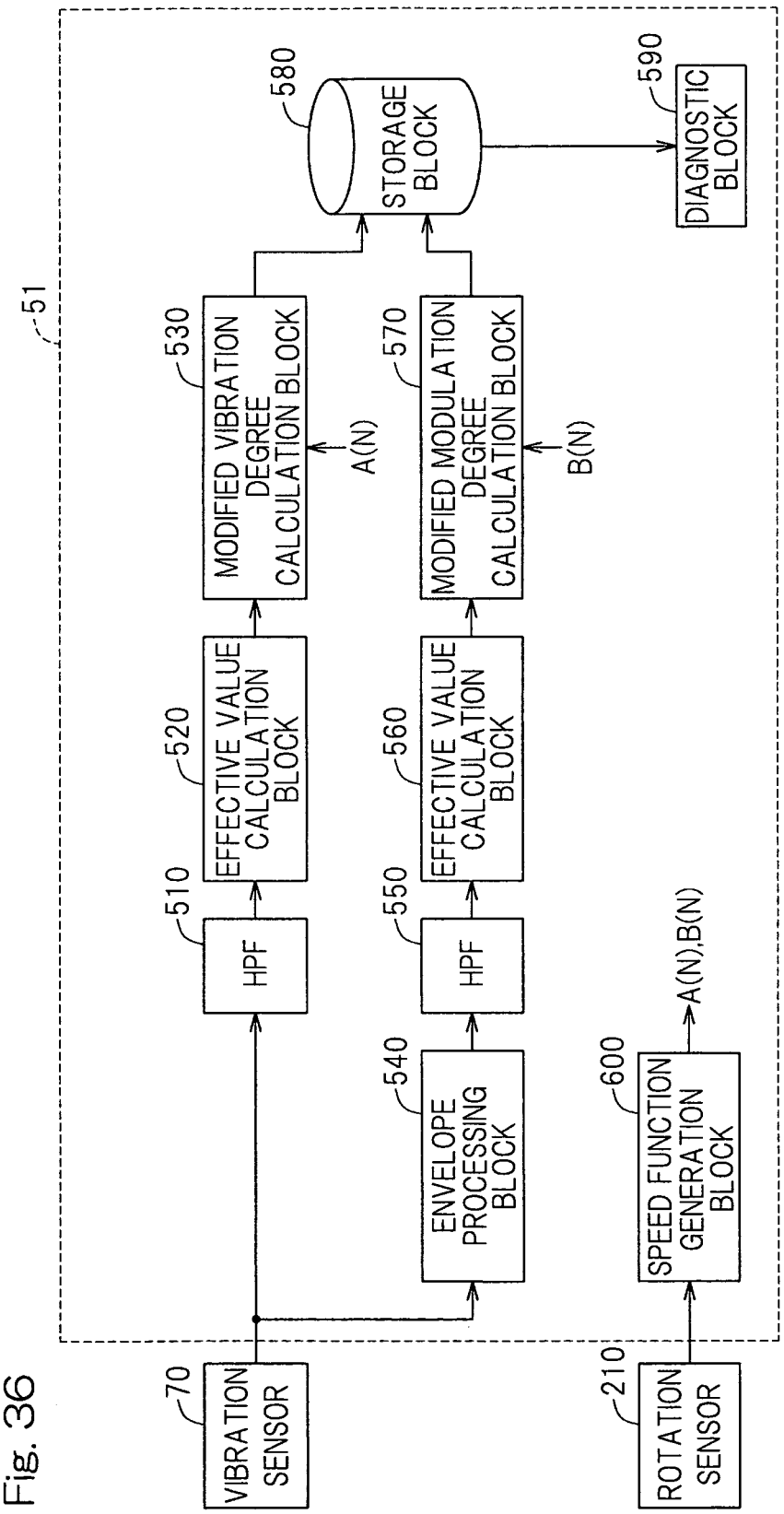
FIG. 36 is a block diagram showing a conceptual construction of a second specific example 2 of the vibration abnormality diagnostic section referred to above.

FIG. 36 illustrates a functional block diagram showing functionally the structure of the vibration abnormality diagnostic section 51 employed in this Specific Example 2. As shown in FIG. 36, the abnormality diagnostic section 51 is similar to the abnormality diagnostic section 51 employed in the previously described Specific Example 1 shown in FIG. 29, except that a modified vibration degree calculation block 530, a modified modulation degree calculation block 570 and a speed function generation block 600 are additionally employed.

The speed function generation block 600 receives a detection value descriptive of the rotational speed of the main shaft 420 from the rotation sensor 210. It is to be noted that the rotation sensor 210 may be capable of outputting a detection value descriptive of the rotational position of the main shaft 420 so that the rotational speed of the main shaft 420 can be calculated in the speed function generation block 600. The speed function generation block 600 generates a speed function A(N) for normalizing the effective value of the vibration waveform of the bearing, calculated by an effective value calculation block 520, with the rotational speed N of the main shaft 420 and a speed function B(N) for normalizing the effective value of the alternating current component of the envelope waveform, calculated by an effective value calculation block 560, with the rotational speed N of the main shaft 420. By way of example, the speed functions A(N) and B(N) are expressed by the following formulas:

$$A(N)=a \times N^{-0.5} \qquad (1)$$

$$B(N)=b \times N^{-0.5} \qquad (2)$$

where a and b represent respective constants determined by, for example, a series of experiments and may be of respective values either different from each other or equal to each other.

The modified vibration degree calculation block 530 receives the effective value of the vibration waveform of the bearing from an effective value calculation block 520 and the speed function A(N) from the speed function generation block 600. Then, the modified vibration degree calculation block 530 makes use of the speed function A(N) to calculate a value, which corresponds to the effective value of the vibration waveform, calculated by the effective value calculation block 520, that is normalized with the rotational speed of the main shaft 420 (hereinafter referred to as "modified vibration degree"). More specifically, using the effective value vr of the vibration waveform calculated by the effective value calculation block 520 and the speed function A(N), the modified vibration degree Vr* is calculated by the following formula:

$$Vr^* = A(N)\sqrt{\frac{\int_0^T \{Vr(t) - Vra\}^2 \, dt}{T}} \quad (3)$$

where Vra represents the average value of Vr during the time span 0 to T.

The modified vibration degree calculation block 530 outputs to the storage block 580 a modified vibration degree Vr* calculated by the formula (3) above.

The modified modulation degree calculation block 570 receives the effective value of the alternating current component of the envelope waveform from the effective value calculation block 560 and the speed function B(N) from the speed function generation block 600. The modified modulation degree calculation block 570 makes use of the speed function B(N) to calculate a value which corresponds to the effective value of the alternating current component of the envelope waveform, calculated by the effective value calculation block 560, that is normalized with the rotational speed of the main shaft 420 (hereinafter referred to as "modified modulation degree"). More specifically, using the effective value Ve of the alternating current component of the envelope waveform calculated by the effective value calculation block 560 and the speed function B(N), the modified vibration degree Ve* is calculated by the following formula:

$$Ve^* = B(N)\sqrt{\frac{\int_0^T \{Ve(t) - Vea\}^2 \, dt}{T}} \quad (4)$$

In this formula (4) Vea represents the average value of Ve during the time span 0 to T. The modified modulation degree calculation block 570 outputs to the storage block 580 the modified modulation degree Ve* calculated by the formula (4) above. The modified vibration degree calculation block 530 outputs to the storage block 580 the modified vibration degree Vr* calculated by the formula (3) referred to previously.

The modified vibration degree Vr* and the modified modulation degree Ve*, which have been stored in the storage block 580 from moment to moment, are read out by a diagnostic block 590 and, on the basis of the chronological change of the modified vibration degree Vr* and the modified modulation degree Ve*, which have been so read out, the abnormality diagnosis of the bearing is performed by the diagnostic block 590.

It is to be noted that in the foregoing the rotation sensor 210 may be fitted to the main shaft 420 and a rotation sensor equipped bearing assembly of a type, in which the rotation sensor 210 is incorporated in the bearing assembly, may be used in the bearing that is an object to be diagnosed.

As hereinabove described, according to the Specific Example 2, since the presence or absence of the abnormality is diagnosed on the basis of the modified vibration degree Vr*, which corresponds to the effective value of the vibration waveform of the bearing normalized with the rotational speed, and the modified modulation degree Ve*, which corresponds to the effective value of the alternating current component of the envelope waveform normalized with the rotational speed, the further accurate abnormality diagnosis can be realized with disturbances resulting from the change in rotational speed having been removed.

Specific Example 3

Figure 37:
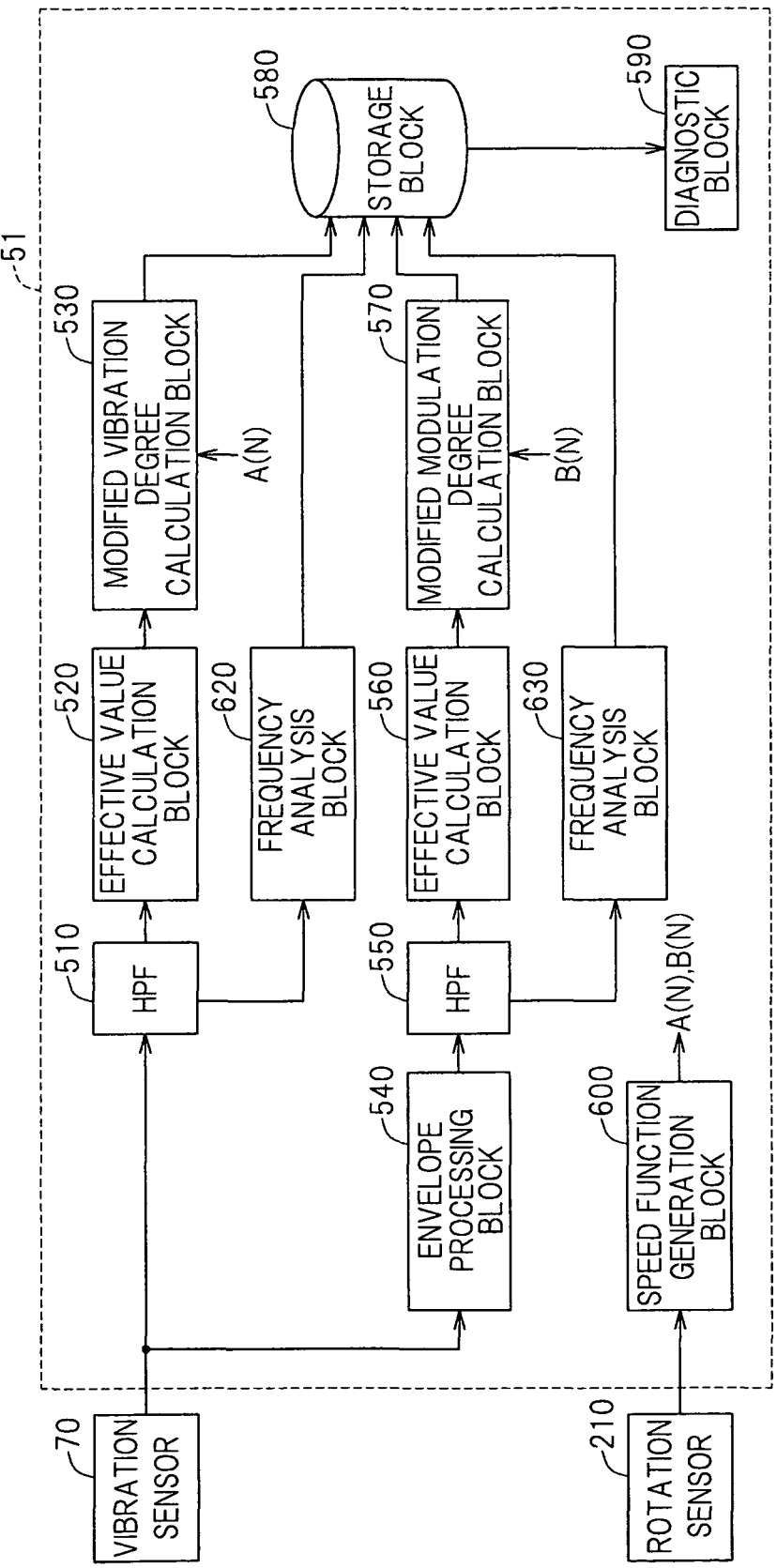
FIG. 37 is a block diagram showing a conceptual construction of a third specific example 3 of the vibration abnormality diagnostic section referred to above.

In this Specific Example 3, in order to perform further accurate abnormality diagnosis, the abnormality diagnosis relying on the frequency analysis is concurrently used in addition to the Specific Example 1 or the Specific Example 2 described hereinabove. FIG. 37 illustrates a functional block diagram functionally showing the structure of the vibration abnormality diagnostic section 51 employed in the practice of the Specific Example 3. As shown in FIG. 37, the abnormality diagnostic section 51 is similar to the abnormality diagnostic section 51, shown in and described with reference to FIG. 36, except that frequency analysis blocks 620 and 630 are additionally employed.

The frequency analysis block 620 received from the HPF 510 a vibration waveform of the bearing from which a direct current component has been removed. The frequency analysis block 620 performs a frequency analysis on the vibration waveform of the bearing so received and then outputs a result of the frequency analysis to the storage block 580. By way of example, the frequency analysis block 620 applies the fast Fourier transform (FFT) process on the vibration waveform of the bearing which it receives from the high pass filter 510, and a peak frequency exceeding a predetermined threshold value is subsequently outputted to the storage block 580.

Also, the frequency analysis block 630 receives from the high frequency filter 550 an alternating current component of the envelope waveform from which a direct current component has been removed. And, the frequency analysis block 630 performs a frequency analysis on the alternating current component of the envelope waveform so received and then outputs a result of the frequency analysis to the storage block 580. By way of example, the frequency analysis block 630 applies a FFT process on the alternating current component of the envelope waveform, which is received from the high pass filter 550, and a peak frequency exceeding a predetermined threshold value is subsequently outputted to the storage block 580.

The diagnostic block 590 referred to above reads out from the storage block 580 the results of the frequency analysis performed respectively by the frequency analysis blocks 620 and 630 together with the modified vibration degree Vr* and the modified modulation degree Ve* and performs a further reliable abnormality diagnosis by concurrently utilizing the results of the frequency analysis together with the chronological changes of the modified vibration degree Vr* and the modified modulation degree Ve*.

By way of example, the results of the frequency analysis performed respectively by the frequency analysis blocks 620 and 630 can be used in estimating the site of generation of the abnormality when the abnormality is detected by the abnormality diagnosis based on the modified vibration degree Vr* and the modified modulation degree Ve*. In other words, when a damage occurs within the bearing, a peak of a vibration of a particular frequency theoretically determined from the geometric structure within the bearing assembly and the rotational speed is generated in dependence on the damaged site (inner ring, outer ring, rolling elements). Accordingly, by concurrently utilizing the result of the frequency analysis, performed respectively by the frequency analysis blocks 620 and 630 with the abnormality diagnosis based on the modified vibration degree Vr* and the modified modulation degree Ve* both referred to above, further accurate diagnosis of the abnormality occurring site can be accomplished.

It is to be noted that although in the foregoing the frequency analysis blocks 620 and 630 have been shown and described as added to the Specific Example 2 described hereinbefore, the frequency analysis blocks 620 and 630 may be added to the abnormality diagnostic section 51 employed in the practice of the Specific Example 1 shown in and described with reference to FIG. 29.

As hereinabove described, according to the Specific Example 3, since the abnormality diagnosis relaying on the frequency analysis is concurrently used, the reliability of the abnormality diagnosis can be further increased and the abnormality occurring site can be further accurately diagnosed.

Specific Example 4

In the Specific Example 4 discussed hereinbelow, in order to further increase the reliability of the abnormality diagnosis of the bearing, detection values of various sensors are utilized concurrently. In this Specific Example 4, instead of the provision of the displacement abnormality diagnostic section 52, the internal cracking abnormality diagnostic section 53 and the impurity abnormality diagnostic section 54, which are shown in FIG. 20, or in addition to those abnormality diagnostic sections 52 to 54, abnormality detecting functions for the above described displacement abnormality, internal cracking and impurity are added to the vibration abnormality diagnostic section 51.

Figure 38:
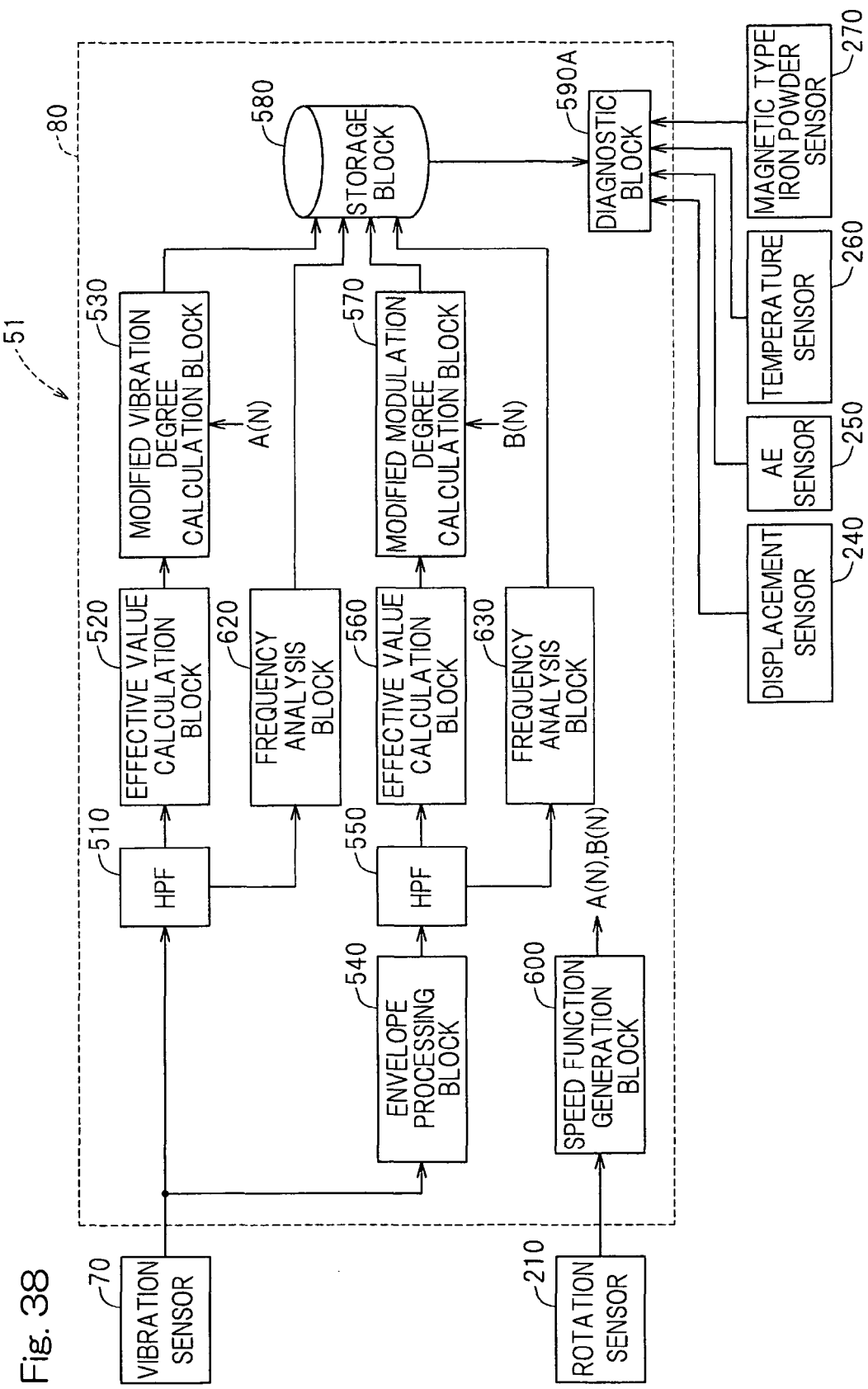
FIG. 38 is a block diagram showing a conceptual construction of a fourth specific example 4 of the vibration abnormality diagnostic section referred to above.

FIG. 38 illustrates a functional block diagram showing functionally the structure of the vibration abnormality diagnostic section 51 employed in the practice of the Specific Example 4. As shown in FIG. 38, the abnormality diagnostic section 51 is similar to the abnormality diagnostic section 51 shown in described with reference to FIG. 37, but differs therefrom in that it includes a diagnostic block 590A in place of the diagnostic block 590.

In the Specific Example 4, in addition to the vibration sensor 70 and the rotation sensor 210, at least one of a displacement sensor 240, an AE (Acoustic Emission) sensor 250, a temperature sensor 260 and a magnetic type iron powder sensor which is an impurity sensor 270 (hereinafter referred to as "magnetic type iron powder sensor 270") is further employed. The diagnostic block 590A receives a detection value from at least one of the displacement sensor 240, the AE sensor 250, the temperature sensor 260 and the magnetic type iron powder sensor 270 that are provided therein. Also, the diagnostic block 590A reads out from the storage block 580 the modified vibration degree Vr* and the modified modulation degree Ve* and respective results of the frequency analysis performed by the frequency analysis blocks 620 and 630.

The diagnostic block 590A makes concurrent use of the detection value, received from at least one of the displacement sensor 240, the AE sensor 250, the temperature sensor 260 and the magnetic type iron powder sensor 270, together with the modified vibration degree. Vr*, the modified modulation degree Ve* and the respective results of the frequency analysis performed by the frequency analysis blocks 620 and 630 to thereby perform the abnormality diagnosis of the bearing assembly.

The displacement sensor 240 is fitted to the bearing for detecting the relative displacement of the inner ring relative to the outer ring of the bearing 60, which relative displacement is subsequently outputted to the diagnostic block 590A. In the practice of the above described modified vibration degree Vr*, modified modulation degree Ve* and frequency analyzing techniques which utilize the detection value of the vibration sensor 70, it is difficult to detect the abnormality relative to the overall abrasion of the rolling surface, but the abrasion within the bearing can be detected by detecting the relative displacement of the inner ring relative to the outer ring with the displacement sensor 240. The diagnostic block 590A determines the occurrence of the abnormality in the bearing in the event that the detection value from the displacement sensor 240 is higher than a predetermined value (threshold value S3). It is to be noted that since the displacement sensor 240 detects the relative displacement between the outer ring and the inner ring, it is necessary to maintain the accuracy of a non-measuring surface at a high quality.

The AE sensor 250 is fitted to the bearing for detecting an acoustic emission wave (AE signal) generated from the bearing and then outputs it to the diagnostic block 590A. This AE sensor 250 is excellent in detecting the internal cracking occurring in a member forming the bearing and the concurrent use of this AE sensor 250 makes it possible to early detect the exfoliation abnormality which is generated because of the internal cracking of a kind difficult to detect by the vibration sensor 70. In the event that the number of time the amplitude of the AE signal detected by the AE sensor 250 exceeds a predetermined value is higher than the threshold value S4 and/or in the event that the AE signal or a signal obtained by conducting the envelope process on the AE signal is higher than a threshold value, the diagnostic block 590A determines the occurrence of the abnormality in the bearing.

The temperature sensor 260 is fitted to the bearing for detecting the temperature of the bearing and then outputs a signal indicative of the temperature so detected to the diagnostic block 590A. In general, the bearing evolves heat in the event of an insufficient lubrication and the undersize of a gap inside of the bearing and will fail to rotate when a seized condition occurs through a change in color of the rolling surface and/or a plastic welding. Accordingly, by detecting the temperature of the bearing with the temperature sensor 260, the abnormality such as, for example, the insufficient lubrication can be detected early. It is to be noted that in place of the temperature sensor 260 fitted to the bearing, the previously described oil temperature measuring instrument 8 for detecting the oil temperature may be utilized.

The diagnostic block 590A performs the abnormality diagnosis such as, for example, the insufficient lubrication by further referring to the detection value of the temperature sensor 260 when the modified vibration degree Vr* and the modified modulation degree Ve* exhibit such a behavior as shown in FIG. 37. It is to be noted that the diagnostic block 590A referred to above may determines the occurrence of the abnormality in the bearing only by reason that the detection value from the temperature sensor 260 is higher than the predetermined value.

The temperature sensor 260 is constituted by, for example, a thermister, a platinum resistance element or a thermocouple.

The magnetic type iron powder sensor 270 detects the amount of an iron powder contained in the lubricant for the bearing and then outputs its detected value to the diagnostic block 590A. This magnetic type iron powder sensor 270 is comprised of, for example, a rod shaped electrode and an electrode having a magnet built therein and is disposed in the circulating path of the lubricant for the bearing. The magnetic type iron powder sensor 270 captures the iron powder, contained in the lubricant, by means of the magnet and outputs a signal in the event that the electric resistance between the electrodes lowers below a predetermined value as a result of adhesion of the iron powder. In other words, when the bearing wears frictionally, the iron powder resulting from the abrasion admixes into the lubricant and, therefore, by detecting the amount of the iron powder contained in the lubricant for the bearing with the magnetic type iron powder sensor 270, the abrasion of the bearing 60 can be detected. The diagnostic block 590A when receiving the signal from the magnetic type iron powder sensor 270 determines the occurrence of the abnormality in the bearing 60.

It is to be noted that although not specifically shown, an optical sensor capable of detecting a turbidity of the lubricant based on a transmittance may be employed in place of the magnetic iron powder sensor 270. By way of example, the optical sensor detects the amount of the bearing abrasion powder in the lubricant oil by projecting rays of light from a light emitting element onto the lubricant oil and detecting a change in intensity of light arriving at a light receiving element. It is to be noted that the transmittance of the light is defined by the ratio between an output value of the light receiving element, when no foreign matter is admixed in the lubricant oil, and an output value of the light receiving element, when iron oxide is admixed therein, and the diagnostic block 590A determines the occurrence of the abnormality in the bearing when the transmittance thereof is higher than a predetermined value.

Figure 40:
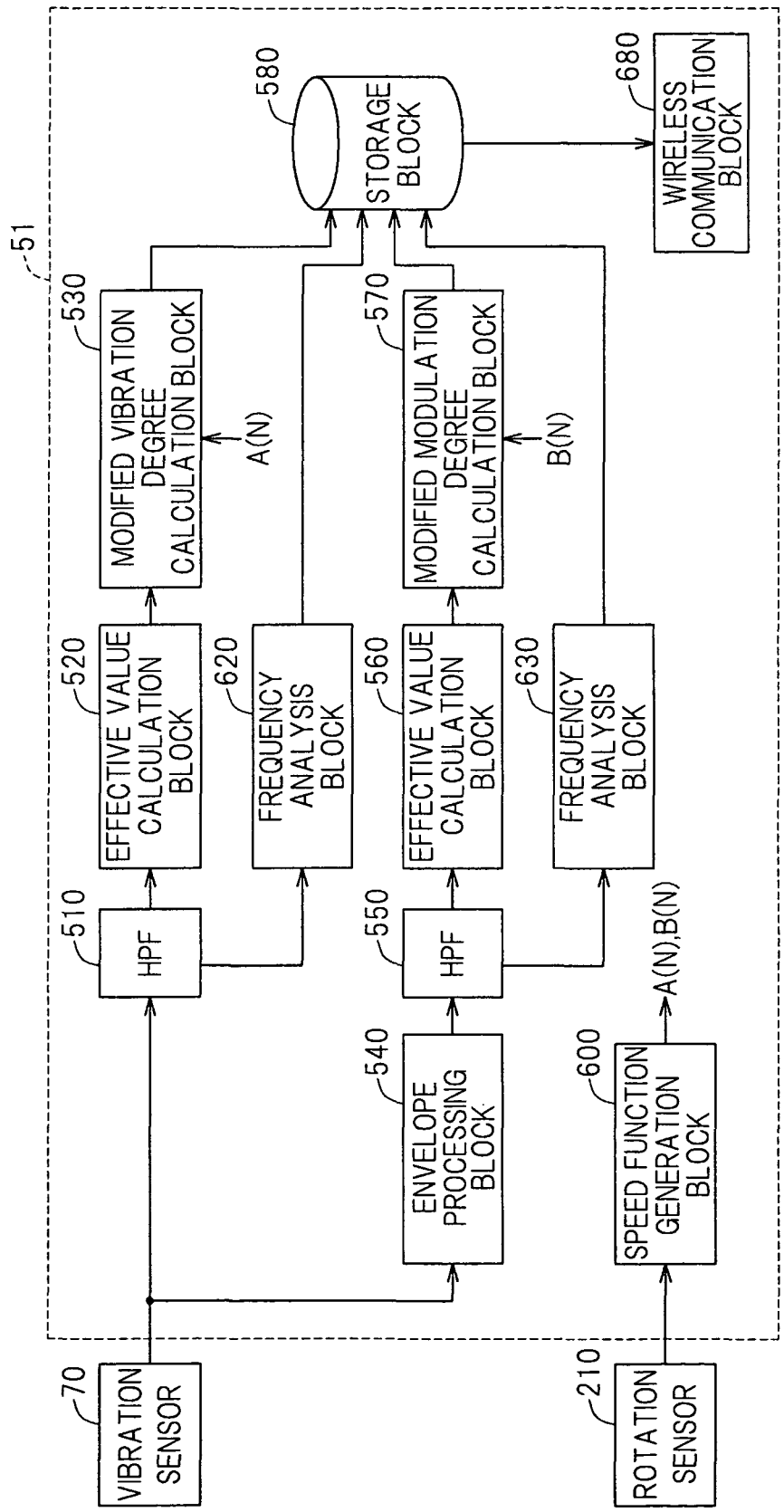
FIG. 40 is a block diagram showing a fifth specific example 5 of the vibration abnormality diagnostic section.

It is to be noted that although in FIG. 40, the displacement sensor 240, the AE sensor 250, the temperature sensor 260 and the magnetic type iron powder sensor 270 are shown, all of them may not be necessarily employed and the use of only one of them is effective to increase the reliability of the abnormality diagnosis.

According to the foregoing Specific Example 4, since the detection values of the various sensors are utilized concurrently as described hereinabove, the reliability of the abnormality diagnosis can be further increased. In particular, by the concurrent use of the displacement sensor 240 the abrasion taking place within the bearing can be diagnosed and, by the concurrent use of the AE sensor 250, the exfoliation abnormality occurring as a result of the internal cracking can be diagnosed early. Also, by the concurrent use of the temperature sensor 260, the abnormality such as, for example, the insufficient lubrication can be diagnosed early and, by the concurrent use of the magnetic type iron powder sensor 270 and the optical sensor or the like capable of detecting the turbidity of the lubricant through the transmittance of light, the abrasion of the bearing can be diagnosed.

It is to be noted that the displacement abnormality diagnostic section 52, the internal cracking abnormality diagnostic section 53 and the impurity abnormality diagnostic section 54, all shown in FIG. 20, are provided as respective instruments for performing the various functions of the abnormality diagnosis for the displacement, internal cracking and impurity of the diagnostic section 590A shown in FIG. 38, separately from the vibration abnormality diagnostic section 51.

Figure 39:
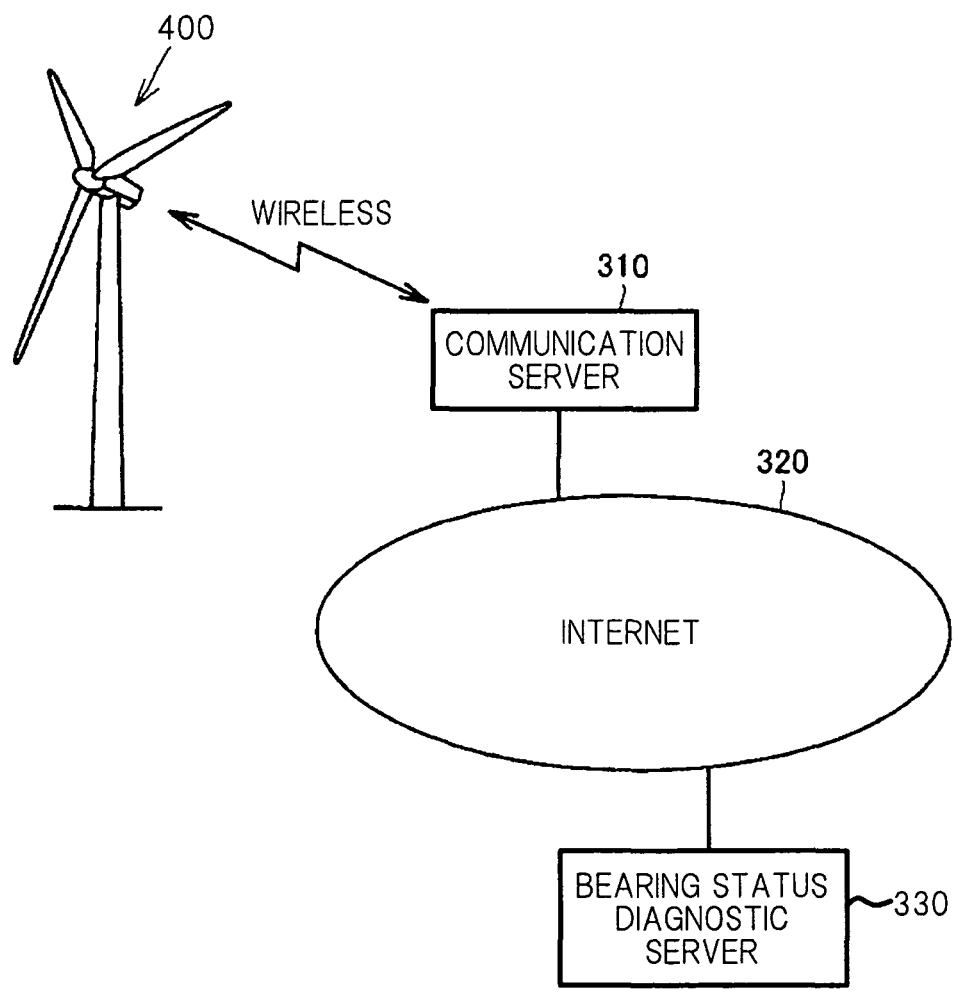
FIG. 39 is a schematic diagram showing schematically the entire construction of the status monitoring system for the rolling device, which is used in a wind turbine generator that utilizes a communication unit for a remote place.

FIG. 39 illustrates an expanded example of the status monitoring system for the rolling device of a kind employed in this wind turbine generator. The nacelle 490 best shown in FIG. 21 is installed at a high location and, therefore, considering the capability of conducting the maintenance, the status monitoring system for the wind turbine generator is desirably installed at a location distant from the nacelle 490. However, to transmit the vibration waveform itself, which is measured with the use of the vibration sensor 70, to a remote place require a transmitting device having a high transmitting speed and this may result in an increase of the cost. Also, considering that the nacelle 490 is installed at the high location as discussed above, the use of a wireless communication is desirable for a communication device from the nacelle 490 to the outside.

Figure 41:
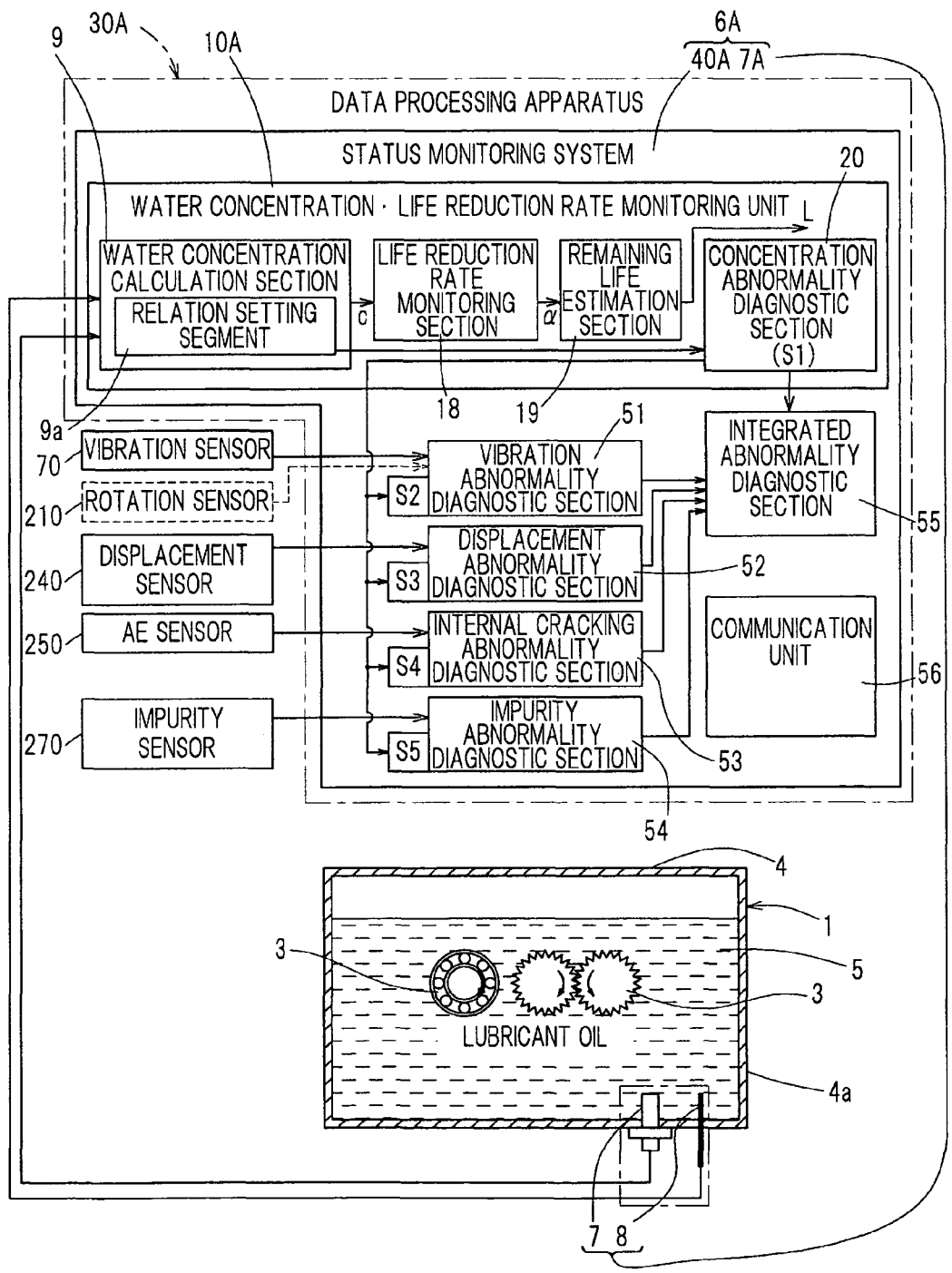
FIG. 41 is a block diagram showing a conceptual construction of the status monitoring system for the rolling device in accordance with a thirteenth embodiment of the present invention.

In view of the above, in the example shown in FIG. 41, the calculation of the water concentration, the calculation of the modified vibration degree Vr* and the modified modulation degree Ve* and the frequency analyzing process (where the frequency analysis is concurrently used) are executed in the data processing apparatus provided in the nacelle 490, and the calculated water concentration, the calculated modified vibration degree Vr* and modified modulation degree Ve* and the calculated result of the frequency analysis (the peak frequency) are transmitted wirelessly from the nacelle 490 to the outside. The data transmitted warlessly from the nacelle 490 are received by a communication server connected with the Internet and the abnormality diagnosis of the bearing is performed after the data have been transmitted to a diagnostic server through the Internet.

FIG. 39 illustrates a schematic diagram schematically showing the entire structure of the status monitoring system for the rolling device used in the wind turbine generator utilizing the communication device to the remote place. As shown in FIG. 39, the status monitoring system for the wind turbine generator includes a wind turbine generator 400, a communication server 310, an Internet 320 and a bearing status diagnostic server 330.

The structure of the wind turbine generator 400 is such as hereinbefore described and, therefore, it will not be reiterated for the sake of brevity. It is however to be noted that as will be described later, in the data processing apparatus of the wind turbine generator 400 in this example, a wireless communication block is provided in place of a diagnostic block. And, the wind turbine generator 400 makes use of the detection value of the vibration sensor 70, as best shown in FIG. 20, to calculate the previously described modified vibration degree Vr* and modified amplitude degree Ve* and the result of the frequency analysis (where the frequency analysis is concurrently used) and outputs the results of those calculations wirelessly to the communication server 310.

The communication server 310 is connected with the Internet 320. And, the communication server 310 receives the communicated data wirelessly from the wind turbine generator 400 and outputs the received data to the bearing status diagnostic server 330 through the Internet 320. The bearing status diagnostic server 330 is connected with the Internet 320. And, the bearing status diagnostic server 330 receives data from the communication server 310 through the Internet 320 and performs the abnormality diagnosis occurring in the bearing, which is provided in the wind turbine generator 400, on the basis of the modified vibration degree Vr* and modified modulation degree Ve* and the result of the frequency analysis (where the frequency analysis is concurrently used) all calculated in the wind turbine generator 400.

Specific Example 5

FIG. 40 illustrates a functional block diagram showing functionally the structure of the vibration abnormality diagnostic section 51 in the data processing apparatus included in the wind turbine generator 400 shown in and described with reference to FIG. 39. As shown in FIG. 40, the abnormality diagnostic section 51 is similar to the abnormality diagnostic section 51 shown in and described with reference to FIG. 37, but differs therefrom in that in place of the diagnostic block 590 a wireless communication block 280 is included. The wireless communication block 280 reads out from the storage block 580 the modified vibration degree Vr*, the modified modulation degree Ve* and the frequency analyzing results by the frequency analysis blocks 620 and 630 and transmits the read-out data wirelessly to the communication server 310 best shown in FIG. 39.

Other structural features of the abnormality diagnostic section 51 shown in that figure are similar to those of the abnormality diagnostic section 51 shown in and described with reference to FIG. 39.

Although in the foregoing it has been described that the warless communication takes place between the nacelle 490 and the communication server 310, the nacelle 490 and the communication server 310 may be connected wired. In such case, a wiring is required, but the wireless communication device is no longer employed and the wired system generally makes it possible to transmit more information and, therefore, processing can be integrated on a main substrate in the nacelle 490.

Also, the status monitoring device used in the above described wind power generating device is preferably constructed independent from the existing power generation monitoring system. By so constructing, the cost of introducing the status monitoring device for the wind power generating device can be suppressed with no need to altering any existing system.

As hereinabove described, according to the Specific Example 5, the abnormality diagnosis of the bearing assembly provided in the wind turbine generator 400 can be performed in the bearing status diagnosis server 330 installed at the remote place, the maintenance load and the cost can be reduced advantageously.

Also, while since the nacelle 490 is installed at a high location the work environment is very bad, the provision of the wireless communication block 280 and the communication server 310 enables a signal output from the nacelle 490 to be transmitted wirelessly and, therefore, a wiring work in the nacelle 490 can be suppressed to a minimal and the no wiring work is needed inside the tower 500 used to support the nacelle 490.

The water concentration calculation section 9 best shown in FIG. 20 may be provided in the data processing apparatus installed in the nacelle 490 or in the bearing status diagnostic server 330 best shown in and described with reference to FIG. 39.

It is to be noted that although the foregoing embodiment has been shown and described as applied to the rolling device 1 forming the wind power generating device, the present invention can be equally applied to the status monitoring of the rolling device that form any various machines such as, for example, the rolling device forming an industrial machine, machine tool or construction machine.

The status monitoring system and the monitoring method according for the rolling device according to a thirteenth embodiment will now be described with particular reference to FIGS. 41 to 43. This status monitoring system 6 for the rolling device includes a status monitoring system 40A, provided in the data processing apparatus 30A, and various sensors (7, 8, 70, 210, 240, 250, 270). The data processing apparatus 30A is similar to that employed in the practice of the previously described first embodiment and is comprised of a computer such as, for example, a microcomputer or a personal computer, and a program executed thereby, or dedicated electronic circuits.

Although in the example shown in FIG. 41, reference has been made to the wind power generating device, the rolling device 1 shown therein may be that employed in, for example, a speed reducing mechanism or a machine tool, or in any other machine and equipment.

The status monitoring system 40A includes a water concentration life reduction rate monitoring section 10 which includes, other than the contaminant water concentration calculation section 9 for monitoring the contaminant water concentration in the lubricant oil used to lubricate the rolling component part 3 of the rolling device 1, a life reduction rate monitoring section 18, a remaining life estimation section 19 and a diagnostic unit 20 for a concentration abnormality, and, in addition thereto, various abnormality diagnostic sections 51 to 55 are provided.

The life reduction rate monitoring section 18 determines the life reduction rate $\alpha$ of the rolling component part 3 from the contaminant water concentration c, detected by the water concentration calculation section 9, with the use of a predetermined relation between the contaminant water concentration c and the life reduction rate $\alpha$ of the rolling element.

Figure 42:
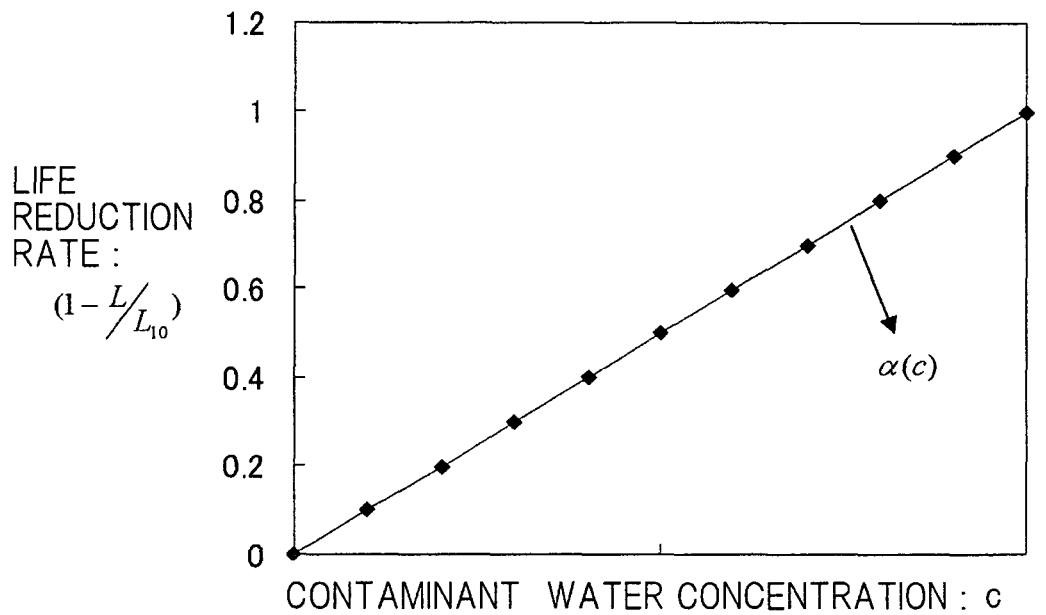
FIG. 42 is a chart showing the relation between the contaminant water concentration in an oil during a preparatory test and the life reduction rate, which is exhibited during a preparatory test.

By way of example, as shown in the graph of FIG. 42, the relation of a function $\alpha(c)$ descriptive of the life reduction rate $\alpha(=[1-\text{Actual Life L/Life L10 under Expected Load}])$ relative to the contaminant water concentration c is determined beforehand from a series of experiments. In this case, assuming that the rolling component part 3, which is the object to be monitored, is a bearing, the contaminant water concentration in the bearing assembly, which is the object to be monitored and which is applied to an actual machine, is measured and the life reduction rate $\pi$ is estimated from the chart of FIG. 42. The experiment to determine the life reduction rate $\alpha$ utilizes a method of determining the threshold value S1 as will be discussed later. The function $\alpha(c)$ so determined in the manner described above is set in the life reduction rate monitoring section 18 as the relation between the contaminant water concentration c and the life reduction rate $\alpha$ of the rolling component part that are determined in the manner described above.

The remaining life estimation section 19 referred to above estimates the remaining life of the rolling component part 3, which is the object to be monitored, by the utilization of the life reduction rate $\alpha$ outputted by the life reduction rate monitoring section 18, and a predetermined remaining life estimation formula. Where the rolling component part 3 is the bearing, the remaining life can be predicated in the following manner. By way of example, the remaining life is estimated by utilizing the idea of Miner's rule (the idea such as disclosed in the non-patent document 11 listed previously that in the case of a material on which various reversed stress amplitudes act, where the repetition rate from the S-N diagram in "a certain breakage probability" to breakage has been made available for each stress threshold values, exfoliation or cracking occurs and the life is reached when summation of the repeat counts at the respective stresses reaches at the "certain breakage probability".) from the contaminant water concentration c and the amount of rotation (life) of the bearing assembly. Hereinafter, such method will be explained.

Figure 43:
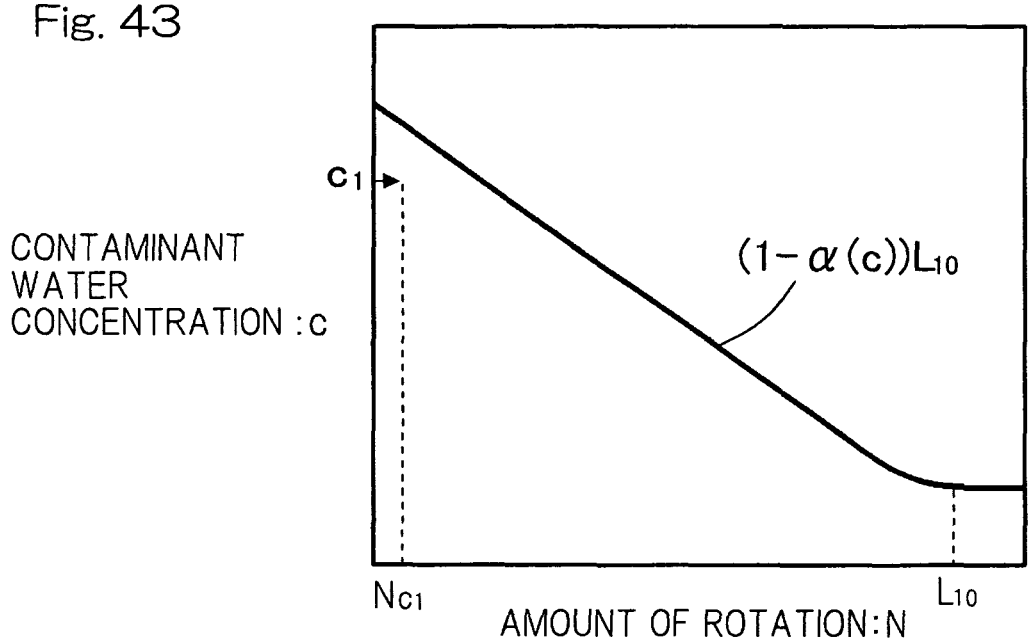
FIG. 43 is a chart showing the relation between the contaminant water concentration and the bearing life, which is expected with an actual bearing.

Based on the data on the life reduction rate given out during the preparatory experiment shown in FIG. 42, the relation between the contaminant water concentration c and the life (amount of rotation) in the actual bearing is derived as shown in FIG. 43. As procedures, the bearing life when the contaminant water concentration is zero (0) is expressed by L10 and the life of the actual bearing assembly at an arbitrarily chosen contaminant water concentration can be determined if $(1-\alpha(c))$ is multiplied by L10 of the actual bearing assembly. It is here assumed that the contaminant water concentration of the actual machine is c1. If the amount of operation Nc1 of the bearing in this condition exceeds $(1-\alpha(c1)) \cdot L10$, the bearing is expected to break down. In other words, if $Nc1/(1-\alpha(c1)) \cdot L10$ exceeds 1, it can be regarded that the life has reached.

It is, however, to be noted that in the case of the actual machine, the bearing assembly is operated under various contaminant water concentrations. In the remaining life estimating method in such case the idea of the Miner's rule which is frequently used in predicating the life of the rolling bearing under various loaded conditions is derived. More specifically, under a certain contaminant water concentration c1, $Nc1/(1-\alpha(c1)) \cdot L10$ when the bearing is operated the amount of rotation Nc1 is determined (hereinafter, this ratio is referred to as the rotational amount life ratio). In other words, when operated under the various contaminant water concentrations, the rotational life ratio is added and, at the time this sum exceeds 1, it is regarded that the life of the bearing assembly has reached. Assuming the remaining life is L, it can be expressed by the following formula:

$$L = \left(1 - \sum_i \frac{N_{ci}}{(1-\alpha(c_i))L_{10}}\right) \times (1 - \alpha(c_{ave}))L_{10}$$

where $c_{ave}$ represents the expected contaminant water concentration in future's operation, Nci represents the accumulated amount of rotation at the contaminant water concentration rank ci (where i represents the rank number), and $c_0$ to $c_R$ represents ranks of the contaminant water concentration (where R represents the number of the ranks).

$c_{ave}$ may be the average contaminant water concentration suffices to be the average contaminant water concentration exhibited during a time zone near to the timing at which the remaining life is calculated. For example, it may be the average value calculated for the past ten days. The calculation of the $c_{ave}$ makes use of the contaminant water concentration c detected by the water concentration calculation section 9. It is to be noted that in order to monitor on a safe side, during the measurement of the contaminant water concentration, it is recommended to measure the high contaminant water concentration by providing the measurement chamber at a lower position than the tank or the oil bath to facilitate capture of water and/or additives.

The remaining life estimation section 19 has the above formula set therein as a predetermined remaining life estimation formula and makes use of the life reduction rate α determined by the life reduction rate monitoring section 18. $L_{10}$ is the $L_{10}$ of a condition with no hydrogen admixed and can be determined by means of a breakdown test. That determined value is used. It is to be noted that by conducting the breakdown test under a constant contaminant water concentration, reduction in life because of the hydrogen brittleness may be suspected. By conducting the breakdown test under this constant contaminant water concentration at various concentrations, the life relative to the contaminant water concentration such as shown in the chart of FIG. 14 comes to be readily available. Accordingly, the function of that life reduction rate is set to be α. If the relation between the contaminant water concentration and the amount of rotation as shown in FIG. 43 is expressed, the exfoliation will occur when the amount of rotation accumulated when the bearing assembly is rotated at the contaminant water concentration c1 attains (1−α(c1))·$L_{10}$. In the meantime, since in the actual machine it is not the constant contaminant water concentration, but the contaminant water concentration changes with time, classification according to the rank such as, for example, classification into $c_2$, $c_3$, $c_4$, . . . and $c_n$ is made beforehand, the idea that the exfoliation occurs and the life is reached at the time the summation of values of the accumulated amount of rotation $N_n$ in those ranks, which are divided by (1−α($c_n$))·$L_{10}$, attains 1 is employed.

Referring to FIG. 41, the diagnostic unit 20 for the concentration abnormality compares the water concentration, detected by the water concentration calculation section 9, with the predetermined threshold value S1 and then determines the occurrence of the abnormality in the event that the result of comparison indicates the excess over the predetermined threshold value S1.

Even the water concentration•life reduction rate, etc. monitoring unit 10A detects the contaminant water concentration from the electrostatic capacitance and the oil temperature that are detected thereby in a manner similar to that employed in the practice of the previously described first embodiment of the present invention, and makes it possible to accurately determine by monitoring the contaminant water concentration in the lubricant oil 5.

Also, from the contaminant water concentration c determined in the manner described above, the life reduction rate α resulting from the hydrogen brittleness in the rolling component part 3 can be determined by the life reduction rate monitoring section 18 from the predetermined relation between the contaminant water concentration and the life reduction rate of the rolling component part. Also, by the remaining life estimation section 19, the remaining life L is determined. The remaining life L makes it possible to predicate the timing of occurrence of, for example, the exfoliation in the bearing from the hydrogen brittleness. Accordingly, when preparation for the maintenance is beforehand made in anticipation of the occurrence of the abnormality, the length of time of halt in operation subsequent to the occurrence of the abnormality can be shortened. It's effect is marked particularly in the case of the wind turbine generator. Also, the abnormality diagnostic section 20 for the concentration abnormality performs the determination of the occurrence of the abnormality in the event that the contaminant water concentration is higher than the threshold value S1. In addition, in the event that the premature damage originating from the hydrogen brittleness of the rolling component part 3 becomes large enough for it to be considered abnormal, it is possible to accurately detect and call someone's attention. In the description that follows, other means than the water concentration•life reduction rate, etc., monitoring unit are similar to those shown in and described in connection with any of the foregoing embodiments of the present invention and, therefore, the details thereof are not reiterated for the sake of brevity.

It is to be noted that in the thirteenth embodiment shown in FIG. 41, the description concerning the measurement chamber installed in one of the electrostatic capacitance detector 7 and the oil temperature measuring instrument 8 for monitoring the contaminant water concentration has been omitted, but the provision of the measurement chamber 12 is preferred such as shown in any of FIGS. 44, 45, 47 and 48.

FIGS. 44 to 48 illustrates fourteenth to eighteenth embodiments of the contaminant water concentration monitoring apparatus 6A for the rolling device. In those embodiments, other than the items that will be described subsequently are similar to those shown in and described with reference to FIGS. 41 to 43 in connection with the thirteenth embodiment. Also, in those FIGS. 44 to 48, of the various means forming the status monitoring system 40A, other means than the water concentration•life reduction rate, etc., monitoring unit 10A are not shown.

Figure 44:
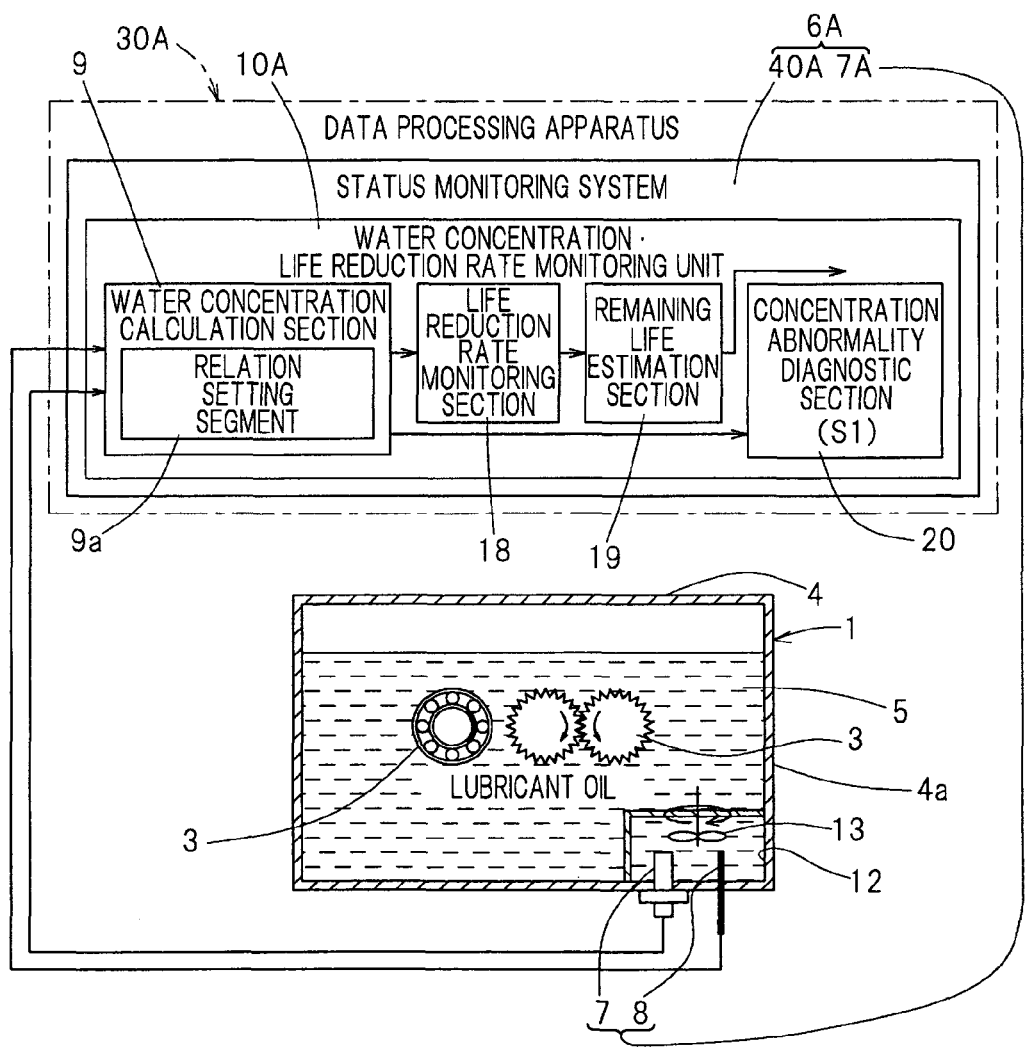
FIG. 44 is a block diagram, with a portion cut out, showing a conceptual construction of the status monitoring system for the rolling device in accordance with a fourteenth embodiment of the present invention.

Although in the thirteenth embodiment shown in FIG. 41, measurement has been made of the electrostatic capacitance and the oil temperature of the lubricant oil 5 within the lubricant oil reservoir 4a in the housing 4, the fourteenth embodiment shown in FIG. 44 is such that the structure of the rolling device 1 except for the data processing apparatus 30A is rendered to be of a structure similar to that employed in the previously described second embodiment shown in FIG. 2. Other functions and effects are similar to those afforded by the previously described second embodiment and, therefore, the details thereof are not reiterated for the sake of brevity.

Figure 45:
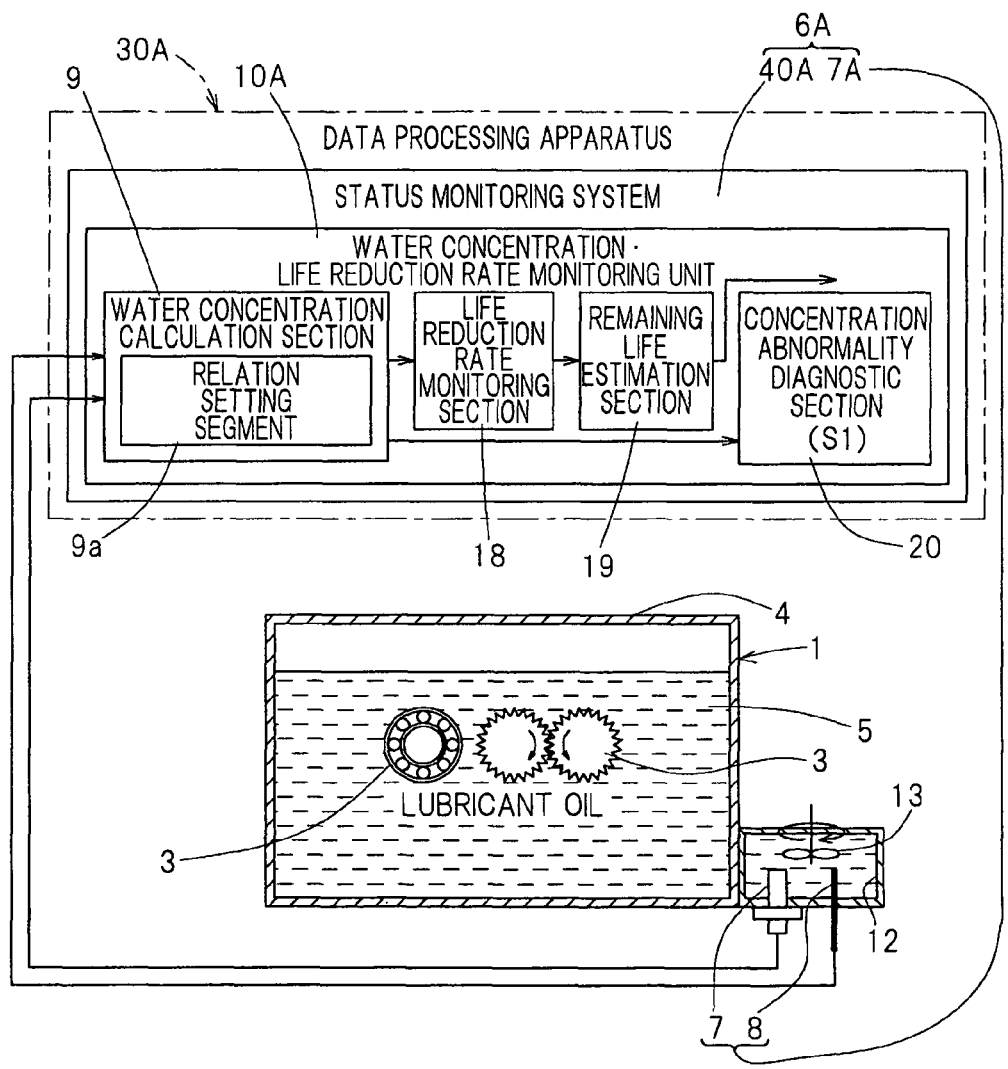
FIG. 45 is a block diagram, with a portion cut out, showing a conceptual construction of the status monitoring system for the rolling device in accordance with a fifteenth embodiment of the present invention.

In the fifteenth embodiment shown in FIG. 45, the structure of the rolling device 1 except for the data processing apparatus 30A is made to be similar to that shown in FIG. 3 in connection with the previously described third embodiment.

Other functions and effects are similar to those afforded by the previously described third embodiment and, therefore, the details thereof are not reiterated for the sake of brevity.

Figure 46:
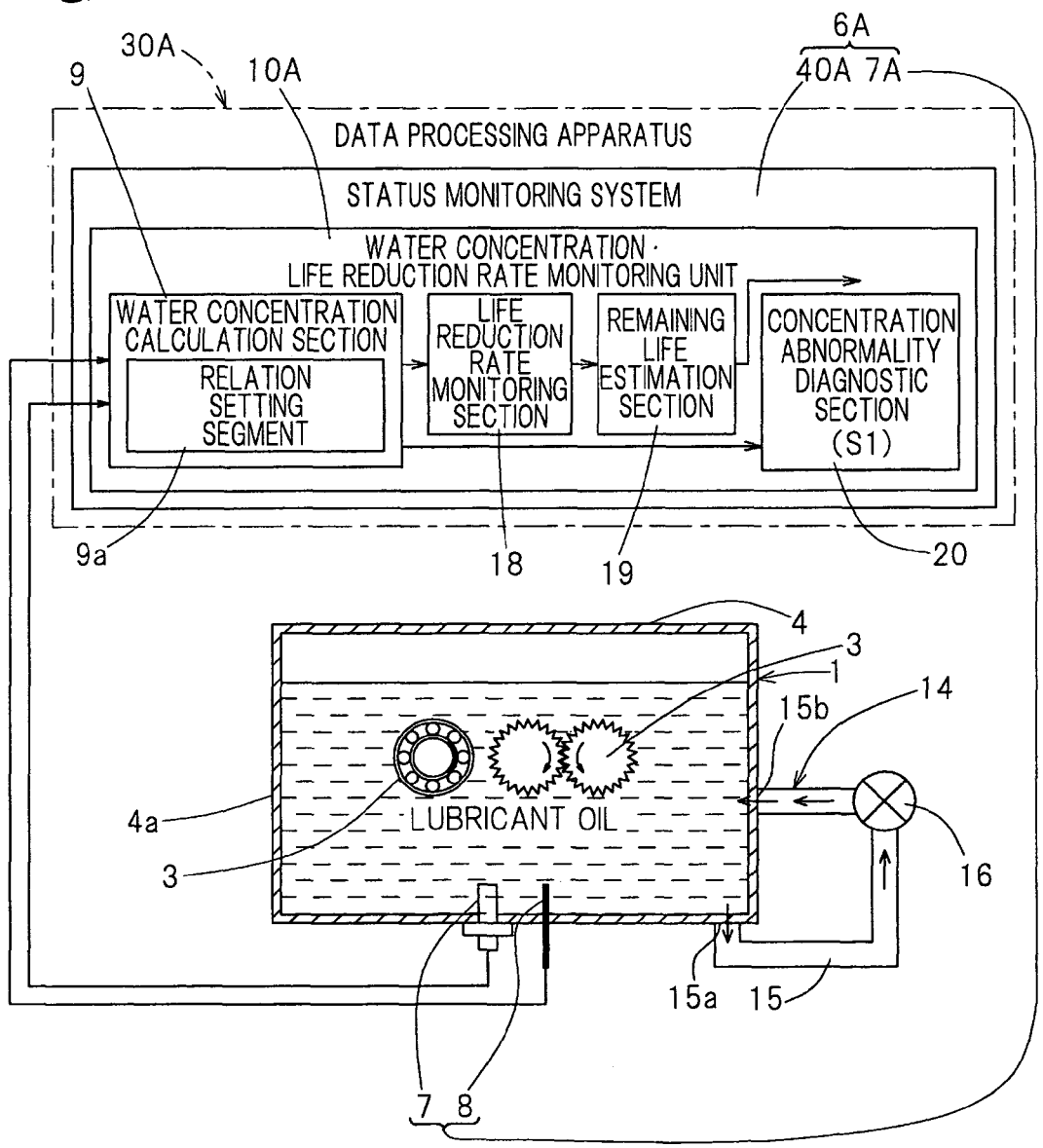
FIG. 46 is a block diagram, with a portion cut out, showing a conceptual construction of the status monitoring system for the rolling device in accordance with a sixteenth embodiment of the present invention.

In the sixteenth embodiment shown in FIG. 46, the structure of the rolling device 1 except for the data processing apparatus 30A is made to be similar to that shown in FIG. 4 in connection with the previously described fourth embodiment. Other functions and effects are similar to those afforded by the previously described fourth embodiment and, therefore, the details thereof are not reiterated for the sake of brevity.

Figure 47:
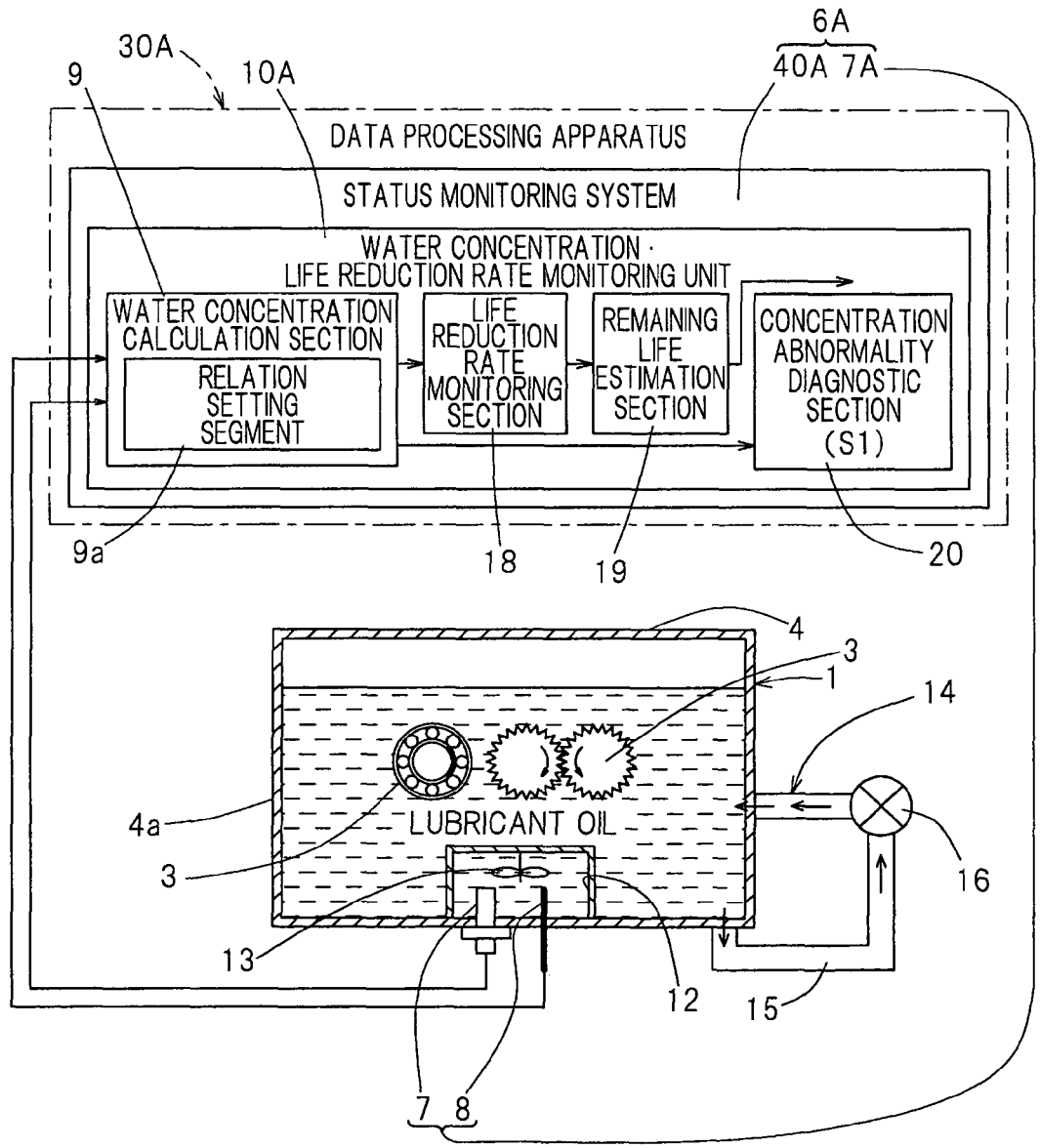
FIG. 47 is a block diagram, with a portion cut out, showing a conceptual construction of the status monitoring system for the rolling device in accordance with a seventeenth embodiment of the present invention.

In the seventeenth embodiment shown in FIG. 47, the structure of the rolling device 1 except for the data processing apparatus 30A is made to be similar to that shown in FIG. 5 in connection with the previously described fifth embodiment. Other functions and effects are similar to those afforded by the previously described fifth embodiment and, therefore, the details thereof are not reiterated for the sake of brevity.

Figure 48:
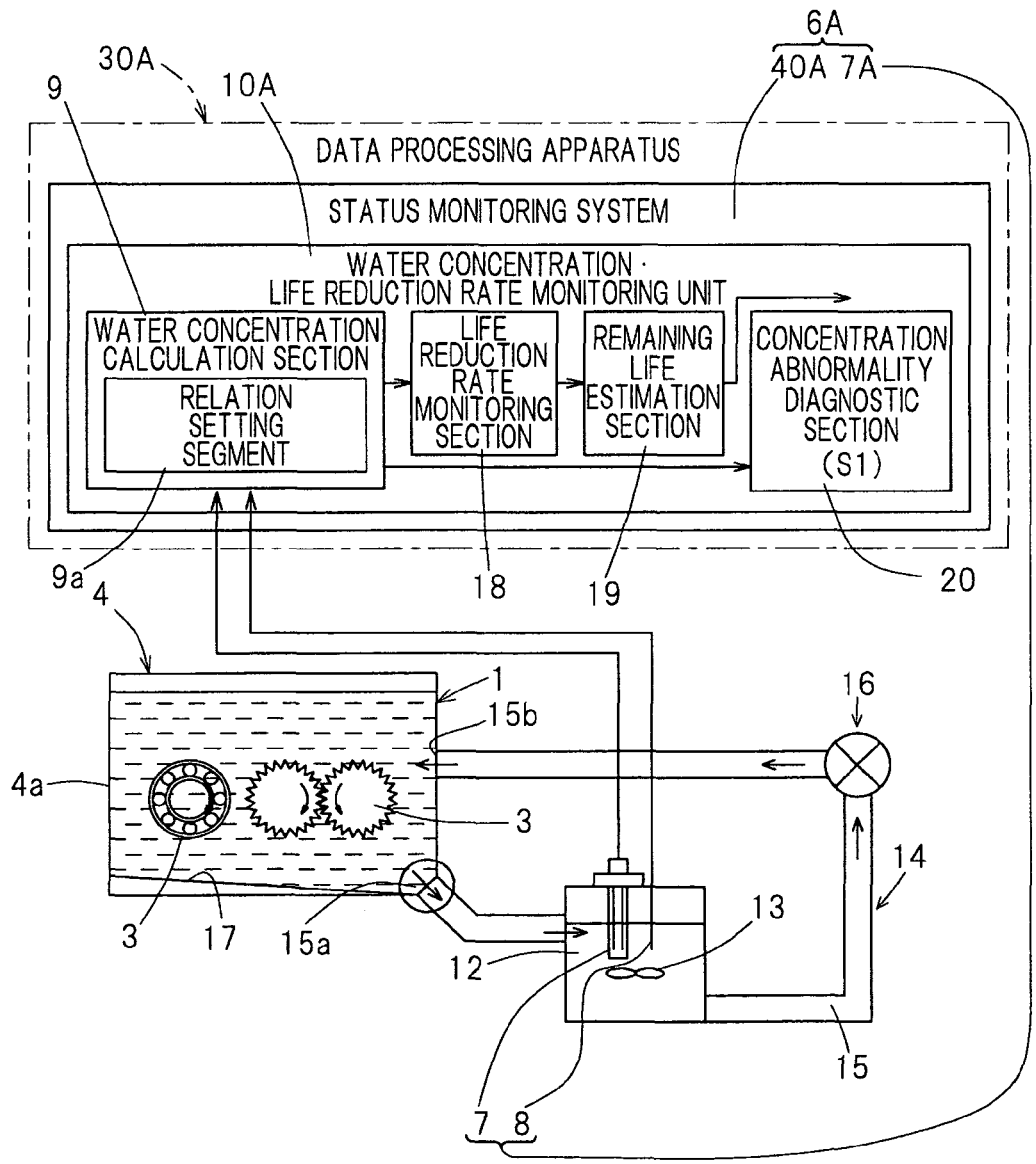
FIG. 48 is a block diagram, with a portion cut out, showing a conceptual construction of the status monitoring system for the rolling device in accordance with an eighteenth embodiment of the present invention.
Figure 49:
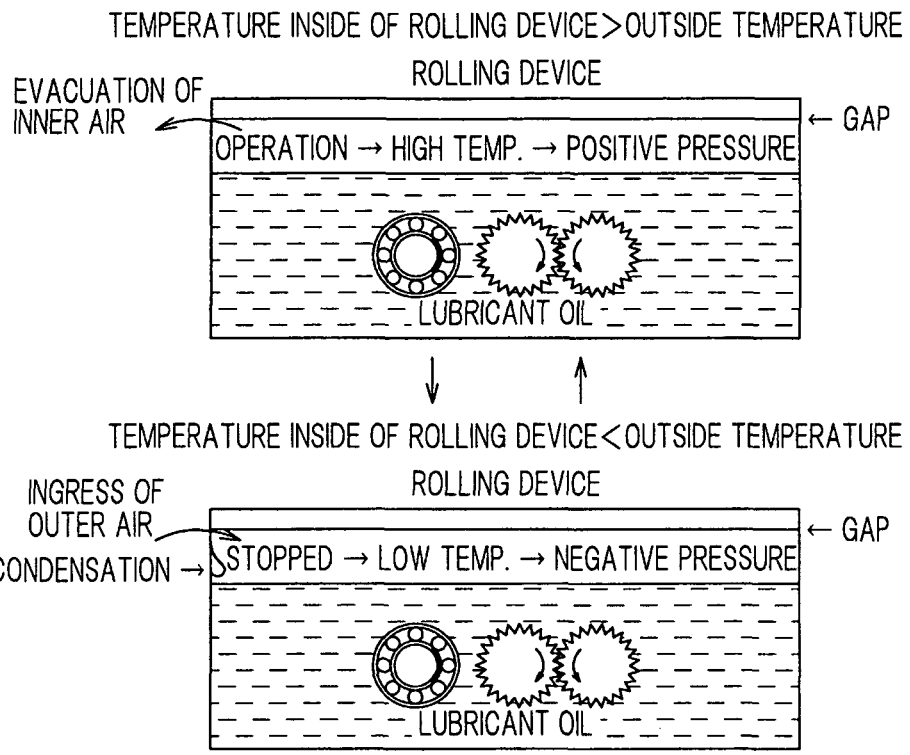
FIG. 49 is a schematic diagram showing how water admixes into the lubricant oil in the rolling device of an oil bath lubrication type.
Figure 50:
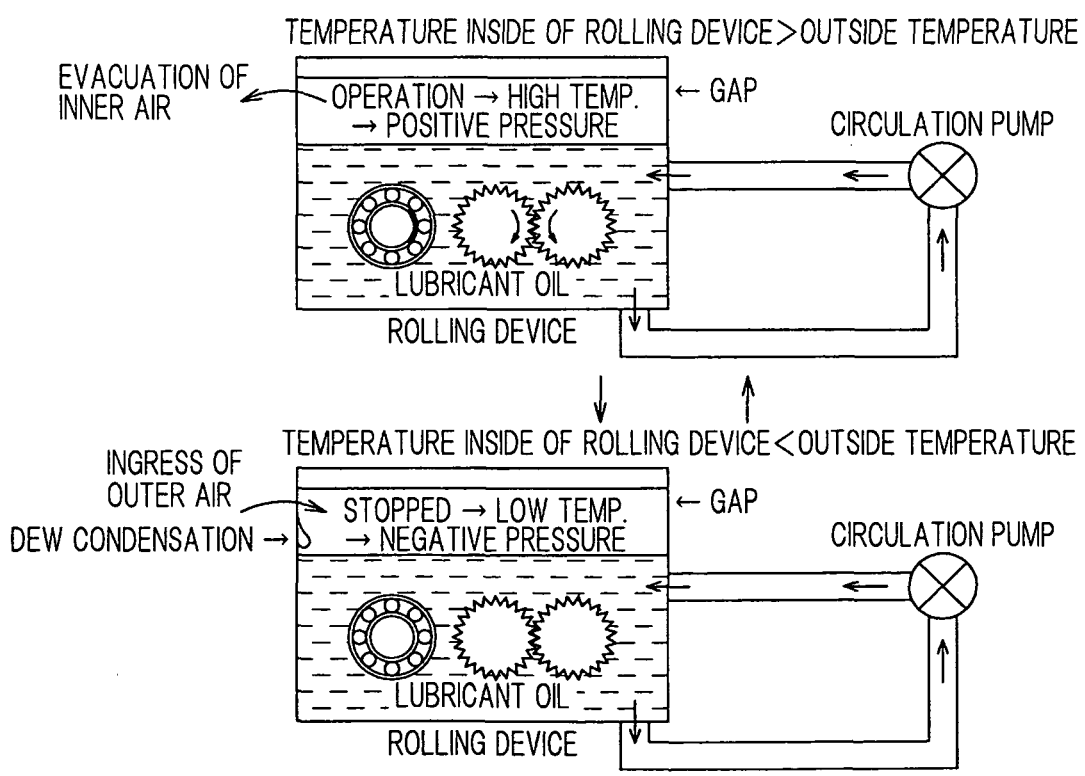
FIG. 50 is a schematic diagram showing how water admixes into the lubricant oil in the rolling device of a circulating oiling type.

In the eighteenth embodiment shown in FIG. 48, the structure of the rolling device 1 except for the data processing apparatus 30A is made to be similar to that shown in FIG. 6 in connection with the previously described sixth embodiment. Other functions and effects are similar to those afforded by the previously described sixth embodiment and, therefore, the details thereof are not reiterated for the sake of brevity.

Also, although not shown, even in the case of the oil bath lubrication type, the inclined groove and the discharge port have to be provided in the rolling device and a reserve tank has to be provided in the circulating oiling type as is the case with the circulating oiling type shown in and described with reference to FIG. 48.

The rolling slide fatigue life testing method and its testing apparatus include the following Modes 1 and 2:

[Mode 1]

The rolling slide fatigue life testing method in accordance with the Mode 1 is a rolling slide fatigue life testing method for performing a rolling slide fatigue life test on a steel material by immersing a to-be-tested element of the steel material into a lubricant oil within a test oil bath and applying a load which will result in a rolling slide contact in such to-be-tested element, in which water is injected into the lubricant oil and the contaminant water concentration in the lubricant oil is then measured by an electrostatic capacitance and an oil temperature.

[Mode 2]

The testing device in accordance with the Mode 2 includes a test oil bath in which a lubricant oil is charged while a to-be-tested element of the steel material is immersed therein; a unit for applying a load which will result in a rolling slide contact in the to-be-tested element within the test oil bath; a water injector for injecting water into the lubricant oil within the test oil bath; an electrostatic capacitance measuring instrument for measuring the electrostatic capacitance of the lubricant oil in the test oil bath; an oil temperature measuring instrument for measuring the oil temperature of the lubricant oil in the test oil bath; and a water concentration calculation section for calculating the contaminant water concentration in the lubricant in accordance with a predetermined rule from the electrostatic capacitance, measured with the electrostatic capacitance measuring instrument, and the oil temperature measured with the oil temperature measuring instrument.

Although the present invention has been fully described in connection with the embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . Rolling device
2 . . . Control apparatus
3 . . . Rolling component part simulation product
4 . . . Housing
4a . . . Lubricant oil reservoir
5 . . . Lubricant oil
6, 6A . . . Contaminant water concentration monitoring device
7 . . . Electrostatic capacitance detector
8 . . . Oil temperature measuring instrument
9 . . . Water concentration calculation section
10 . . . Abnormality diagnostic section
11 . . . Contaminant water concentration detection unit
12 . . . Measurement chamber
13 . . . Stirrer
16 . . . Circulation pump
17 . . . Inclined groove (a mechanism to facilitate the discharge of an additive having a high specific gravity)
18 . . . Life reduction rate monitoring section
19 . . . Remaining life estimation section
20 . . . Concentration abnormality diagnostic section
40, 40A . . . Status monitoring system
51 . . . Vibration abnormality diagnostic section
52 . . . Displacement abnormality diagnostic section
53 . . . Internal cracking abnormality diagnostic section
54 . . . Impurity abnormality diagnostic section
55 . . . Integrated abnormality diagnostic section
70 . . . Vibration sensor
101 . . . Test oil bath
104 . . . Syringe pump
105 . . . Electrostatic capacitance meter
106 . . . Thermocouple
111 . . . Circulation pump
112 . . . Reserve tank
113 . . . Stirrer
142 . . . Water concentration calculation section
141 . . . Testing equipment main body control apparatus
146 . . . Head portion
210 . . . Rotation sensor
240 . . . Displacement sensor
250 . . . AE sensor
270 . . . Impurity sensor
400 . . . Wind turbine generator
420 . . . Main shaft
430 . . . Blade
440 . . . Speed-increasing gear assembly
450 . . . Electric power generator
460 . . . Main shaft bearing
461 . . . Main shaft bearing device
490 . . . Nacelle
500 . . . Tower
510, 550 . . . HPF
520, 560 . . . Effective value calculation block
530 . . . Modified vibration degree calculation block
540 . . . Envelope processing block
570 . . . Modified modulation degree calculation block
580 . . . Storage block
590, 590A . . . Diagnostic block
600 . . . Speed function generation block

620, 630 ... Frequency analysis block
680 ... Wireless communication block
S, S1 ... Threshold value

What is claimed is:

1. A status monitoring system to monitor a status of a rolling device, comprising:
   a contaminant water concentration monitoring device to monitor a contaminant water concentration in a lubricant oil, the contaminant water concentration monitoring device including:
   an electrostatic capacitance detector to detect an electrostatic capacitance in the lubricant oil;
   an oil temperature measuring instrument to detect an oil temperature in the lubricant oil;
   a water concentration calculation section to calculate the contaminant water concentration in accordance with a predetermined rule from the electrostatic capacitance detected by the electrostatic capacitance detector and the oil temperature detected by the oil temperature measuring instrument;
   a lubricant oil reservoir formed as a portion of a housing of the rolling device and capable of performing an oil bath lubrication; and
   a measurement chamber for measurement of the electrostatic capacitance and the oil temperature inside or outside of the housing,
   wherein the electrostatic capacitance detector and the oil temperature measuring instrument are provided within the measurement chamber, and
   the measurement chamber is formed with partitions in the case where the measurement chamber is provided inside the housing.

2. The status monitoring system for the rolling device as claimed in claim 1, further comprising a circulating oiling mechanism capable of performing a circulating oiling.

3. The status monitoring system for the rolling device as claimed in claim 1, further comprising a stirrer to stir the lubricant oil within the measurement chamber for measurement of the electrostatic capacitance and the oil temperature.

4. The status monitoring system for the rolling device as claimed in claim 3, further comprising a mechanism to facilitate a discharge of water or an additive, having a specific gravity higher than that of the lubricant oil, from the measurement chamber for measurement of the electrostatic capacitance and the oil temperature and from the rolling device.

5. The status monitoring system for the rolling device as claimed in claim 1, further comprising an abnormality diagnostic section to compare the contaminant water concentration, calculated by the water concentration calculation section, with a threshold value and to determine an occurrence of an abnormality in the event that the contaminant water concentration is higher than the threshold value.

6. An abnormality diagnostic threshold value setting method for a status monitoring system of a rolling device as described in claim 5 for determining the threshold value for the abnormality diagnostic section, comprising:
   determining a threshold value for the contaminant water concentration through a rolling slide fatigue test in which water is injected into the lubricant oil, the contaminant water concentration is monitored by measuring the electrostatic capacitance and the oil temperature, and feeding the measured contaminant water concentration back so as to control the amount of water injected so that the contaminant water concentration is maintained within a constant range; and
   setting the threshold value so determined to the abnormality diagnostic section as a threshold value.

7. An abnormality diagnostic threshold value setting method for a status monitoring system of a rolling device as described in claim 5 for determining the threshold value for the abnormality diagnostic section, comprising:
   determining a threshold value for the contaminant water concentration through a rolling slide fatigue life test in which a slide is caused in a contact surface by a motion mechanism between elements that contact with each other; and
   setting the threshold value so determined to the abnormality diagnostic section as a threshold value.

8. An abnormality diagnostic threshold value setting method for a status monitoring system of a rolling device as described in claim 5 for determining the threshold value for the abnormality diagnostic section, comprising:
   determining a threshold value for the contaminant water concentration through a rolling slide fatigue life test in which a slide is forcibly caused in a contact surface between elements that contact with each other; and
   setting the threshold value so determined to the abnormality diagnostic section as a threshold value.

9. An abnormality diagnostic threshold value setting method for a status monitoring system of a rolling device as described in claim 5 for determining the threshold value for the abnormality diagnostic section, comprising:
   determining a threshold value for the contaminant water concentration through a rolling slide fatigue life test in which one direction rotation at a constant rotational speed is continued until occurrence of a damage; and
   setting the threshold value so determined to the abnormality diagnostic section as a threshold value.

10. An abnormality diagnostic threshold value setting method for a status monitoring system of a rolling device as described in claim 5 for determining the threshold value for the abnormality diagnostic section, comprising:
    determining a threshold value for the contaminant water concentration through a rolling slide fatigue life test in which acceleration and deceleration operation is continued until occurrence of a damage; and
    setting the threshold value so determined to the abnormality diagnostic section as a threshold value.

11. An abnormality diagnostic threshold value setting method for a status monitoring system of a rolling device as described in claim 5 for determining the threshold value for the abnormality diagnostic section, comprising:
    determining a threshold value for the contaminant water concentration through a rolling slide fatigue life test in which rocking motion is continued until occurrence of a damage; and
    setting the threshold value so determined to the abnormality diagnostic section as a threshold value.

12. An abnormality diagnostic threshold value setting method for a status monitoring system of a rolling device as described in claim 5 for determining the threshold value for the abnormality diagnostic section, comprising:
    determining a threshold value for the contaminant water concentration through a rolling slide fatigue life test in which a mechanism to directly connect a main shaft of a servo motor and a spindle of a testing portion is used in order to eliminate an overlapping vibration component so that a damage in rocking motion may be accurately detected with a vibration; and
    setting the threshold value so determined to the abnormality diagnostic section as a threshold value.

13. An abnormality diagnostic threshold value setting method for a status monitoring system of a rolling device as described in claim 5 for determining the threshold value for the abnormality diagnostic section, comprising:

determining a threshold value for the contaminant water concentration through a rolling slide fatigue life test in which a motor and a spindle of a testing portion are insulated with the use of a rolling element made of a ceramic material for a support bearing assembly for the spindle in order to facilitate an abrasion of an object to be damaged by supplying an electric current between contact elements with the to-be-damaged object being on a positive pole side, and setting the threshold value so determined to the abnormality diagnostic section as a threshold value.

14. An abnormality diagnostic threshold value setting method for a status monitoring system of a rolling device as described in claim 5 for determining the threshold value for the abnormality diagnostic section, comprising:

determining a threshold value for the contaminant water concentration by the use of a rolling slide fatigue life test device capable of performing accelerating and decelerating operation and a rocking motion in addition to the one direction rotation at the constant rotational speed, and setting the threshold value so determined to the abnormality diagnostic section as a threshold value.

* * * * *